US007780950B2

(12) United States Patent
Hazen

(10) Patent No.: US 7,780,950 B2
(45) Date of Patent: Aug. 24, 2010

(54) SYSTEMIC MARKER FOR MONITORING ANTI-INFLAMMATORY AND ANTIOXIDANT ACTIONS OF THERAPEUTIC AGENTS

(75) Inventor: Stanley L. Hazen, Pepper Pike, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 477 days.

(21) Appl. No.: 10/417,838

(22) Filed: Apr. 17, 2003

(65) Prior Publication Data

US 2003/0180218 A1 Sep. 25, 2003

Related U.S. Application Data

(63) Continuation-in-part of application No. 10/039,753, filed on Jan. 2, 2002.

(60) Provisional application No. 60/373,113, filed on Apr. 17, 2002.

(51) Int. Cl.
*C12Q 1/28* (2006.01)
*G01N 33/573* (2006.01)
*G01N 33/68* (2006.01)

(52) U.S. Cl. .......................... 424/9.2; 435/4; 435/7.24; 435/7.4; 435/28; 436/63; 436/86; 436/90

(58) Field of Classification Search .................. 424/9, 424/2; 435/4; 436/63, 86, 90
See application file for complete search history.

(56) References Cited

U.S. PATENT DOCUMENTS

| | | | |
|---|---|---|---|
| 5,122,534 A | 6/1992 | Loose et al. | |
| 5,731,208 A | 3/1998 | Heinecke | 436/86 |
| 5,747,274 A | 5/1998 | Jackowski | |
| 5,889,042 A | 3/1999 | MacLean et al. | |
| 5,985,272 A | 11/1999 | Deby et al. | 424/94.4 |
| 6,046,019 A * | 4/2000 | Goumeniouk et al. | 435/28 |
| 6,096,556 A | 8/2000 | Heinecke | 436/89 |
| 6,133,039 A | 10/2000 | Heinecke | 436/89 |
| 6,268,220 B1 | 7/2001 | Heinecke | 436/501 |
| 6,953,666 B1 | 10/2005 | Kinkade, Jr. et al. | |
| 7,223,552 B2 | 5/2007 | Hazen et al. | |
| 7,476,551 B2 | 1/2009 | Barri et al. | |
| 2002/0164662 A1 | 11/2002 | Hazen et al. | |
| 2003/0119792 A1 | 6/2003 | Roca | |
| 2003/0180218 A1* | 9/2003 | Hazen | 424/9.1 |
| 2006/0051873 A1* | 3/2006 | FitzGerald | 436/86 |

FOREIGN PATENT DOCUMENTS

| | | |
|---|---|---|
| EP | 0 418 486 | 7/1990 |
| EP | 389381 | 9/1990 |
| WO | 96/04311 | 2/1996 |
| WO | 02/50550 | 6/2002 |
| WO | WO 0248715 A2 | 6/2002 |
| WO | WO 02/062207 | 8/2002 |

OTHER PUBLICATIONS

Aviram et al, Chemical Abstracts, vol. 116, Abstr. No. 76147, 1992.*
Downs, et al., Primary Prevention of Acute Coronary Events with Lovastatin in Men and Women with Average Cholesterol Levels: Results of AFCAPS/TexCAPS. Air Force/Texas Coronary Atherosclerosis Prevention Study. *Jama.* 1998;279:1615-22.
Sacks et al., The Effect of Pravastatin on Coronary Events After Myocardial Infarction in Patients with Average Cholesterol Levels. Cholesterol and Recurrent Events Trial Investigators. *N Engl J Med.* 1996;335:1001-9.
Steinberg et al., Beyond Cholesterol. Modifications of Low-Density Lipoprotein that Increase its Atherogenicity. *N Engl J Med.* 1989;320:915-24.
Takemoto et al., Pleiotropic Effects of 3-Hydroxy-3-Methylglutaryl Coenzyme A Reductase Inhibitors. *Arterioscler Thromb Vasc Biol.* 2001;21:1712-9.
Vaughan et al., The Evolving Role of Statins in the Management of Atherosclerosis, *J Am Coll Cardiol.* 2000;35:1-10.
Locatelli et al., Reduction of Plasma 24S-Hydroxycholesterol (Cerebrosterol) Levels Using High-Dosage Simvastatin in Patients with Hypercholesterolemia: Evidence that Simvastatin Affects Cholesterol Metabolism in the Human Brain. [Journal Article] *Archives of Neurology.* 59(2):213-6, Feb. 2002.
Marx, Alzheimer's disease. Bad for the Heart, Bad for the Mind? Science. 294(5542):508-9, Oct. 19, 2001.
Yasomima et al., 3-Hydroxy-3-Methylglutaryl-Coenzyme A Reductase mRNA in Alzheimer and Control Brain. *NeuroReport.* 12(13):2935-8, Sep. 17, 2001.
Stanislaus et al., Lovastatin Treatment Decreases Mononuclear Cell Infiltration into the CNS of Lewis Rats With Experimental Allergic Encephalomyelitis. *Journal of Neuroscience Research.* 66(2):155-62, Oct. 15, 2001.
Novaro et al., Effect of Hydroxymethylglutaryl Coenzyme A Reductase Inhibitors on the Progression of Calcific Aortic Stenosis. *Circulation.* 104(18):2205-9, Oct. 30, 2001.
Ridker et al., Measurement of C-Reactive Protein for the Targeting of Statin Therapy in the Primary Prevention of Actue Coronary Events. N Engl J Med. 2001;344:1959-65.
Ridker et al., Rapid Reduction in C-Reactive Protein With Cerivastatin Among 785 Patients with Primary Hypercholesterolemia. Circulation. 2001;103:1191-3.

(Continued)

*Primary Examiner*—David A Saunders
(74) *Attorney, Agent, or Firm*—Calfee, Halter & Griswold LLP

(57) ABSTRACT

A diagnostic method of monitoring anti-inflammatory and/or antioxidant actions of therapeutic agents comprises determining the level of at least one systemic marker indicative of inflammation or oxidation in a bodily sample taken from a subject at base line or following administration of the therapeutic agent. The marker includes at least one of MPO activity, MPO mass, select MPO-generated oxidation products, and combinations thereof. The level of the systemic marker is compared with a predetermined value to monitor the anti-inflammatory and/or antioxidant actions of the therapeutic agent.

34 Claims, 9 Drawing Sheets

OTHER PUBLICATIONS

Ridker. Are Statins Anti-Inflammatory? Issues in the Design and Conduct of the Pravastatin Inflammation C-Reactive Protein Evaluation. Curr Cardiol Rep. 2000;2:269-73.

International Search Report dated Jul. 31, 2002.

"Oxidized LDL and HDL: antagonists in atherothrombosis" by Mertens, et al., *FASEB J.*, 15, 2073-2084 (2001).

"Macrophage scavenger receptor CD36 is the major receptor for LDL modified by monocyte-generated reactive nitrogen species" by Podrez, et al., *J. Clin. Invest.* 105:1095-1108 (2000).

"Inhibition of Adhesion Molecules Markedly Ameliorates Cytokine-Induced Sustained Myocardial Dysfunction in Dogs *in vivo*" by Momii, et al., *J. Mol. Cell. Cardiol*. 30, 2637-2650 (1998).

"Supplemention with Tetrahydrobiopterin Suppresses the Development of Hypertension in Spontaneously Hypertension Rats" by Hong, et al., *Hypertension*, 2001; 38:1044-1048.

Supplementary European Search Report dated Jan. 29, 2004.

"Kinetics of Oxidation of Tyrosine and Dityrosine by Myeloperoxidase Compounds I and II" by Marquez, et al., *The Journal of Biological Chemistry*, vol. 270, No. 51, Dec. 22, 1995, pp. 30434-30440.

"Leukocytes Utilize Myeloperoxidase-Generated Nitrating Intermediates as Physiological Catalysts for the Generation of Biologically Active Oxidized Lipids and Sterols in Serum" by Schmitt, et al., *Biochemistry*, 1999, 38, 16904-16915.

"Nitric Oxide Modulates the Catalytic Activity of Myeloperoxidase" by Abu-Soud, et al., *The Journal of Biological Chemistry*, vol. 275, No. 8, Feb. 25, 2000, pp. 5425-5430.

"Circulating Myeloperoxidase and Anti-Myeloperoxidase Antibody in Patients with Vasculitis" by Minota, et al., *Scand J. Rheumatol*, 1999;25:94-9.

"Myeloperoxidase Deficiency" by Nauseef, *Hematology, Oncology Clinics of North America*, vol. 2, No. 1, Mar. 1988, pp. 135-158.

"Primary Inherited Defects in Neutrophil Function: Etiology and Treatment" by Malech, et al., *Seminars in Hematology*, vol. 34, No. 4, Oct. 1997, pp. 279-290.

"Mass spectrometric quantification of amino acid oxidation products in proteins: insights into pathways that promote LDL oxidation in the human artery wall" by Heinecke, et al., *FASEB J.*, 13, 1113-1120 (1999).

"Myeloperoxidase-Generated Oxidants and Atherosclerosis" by Podrez, et al., *Free Radical Biology & Medicine*, vol. 28, No. 12, pp. 1717-1725, Jan. 2000.

"Myeloperoxidase, a Catalyst for Lipoprotein Oxidation, Is Expressed in Human Atherosclerosis Lesions" by Daugherty, et al., *J. Clin. Invest.*, vol. 94, Jul. 1994, 437-444.

"3-Chlorotyrosine, a Specific Marker of Myeloperoxidase-catalyzed Oxidation, Is Markedly Elevated in Low Density Lipoprotein Isolated from Human Atherosclerosis Intima" by Hazen, et al., *J. Clin. Invest.*, vol. 99, No. 9, May 1997, 2075-2081.

Elevated levels of protein-bound *p*-hydroxyphenylacetaldehyde, an amino acid-derived aldehyde generated by myeloperoxidase, are present in thin fatty streaks, intermediate lesions and advanced atherosclerosis lesions' by Hazen, et al., *Biochem J*. (2000) 352, 693-699.

"*p*-Hydroxypheylacetaldehyde, and Aldehyde Generated by Myeloperoxidase, Modifies Phospholipid Amino Groups of Low Density Lipoprotein in Human Atherosclerosis Intima" by Heller, et al., *The Journal of Biological Chemistry*, vol. 275, No. 14, Apr. 7, 2000, pp. 9957-9962.

"Association Between Myeloperoxidase Levels and Risk of Coronary Artery Disease" by Zhang, et al., *JAMA*, vol. 286, No. 17, Nov. 7, 2001, pp. 2136-2142.

"Is the Oxidative Modification Hypothesis Relevant to Human Atherosclerosis? Do the Antioxidant Trials Conducted to Date Refute the Hypothesis?" by Steinberg, et al., *Circulation*, 2002; 105:2107-2111.

"The Effect of Local Attachment of Cationized Antioxidant Enzymes on Experimental Colitis in the Rat" by Blau, et al., *Pharmaceutical Research*, vol. 17, No. 9, 2000, pp. 1077-1084.

"Intestinal anti-inflammatory activity of morin on chronic experimental colitis in the rat" by Galvez, et al., Aliment Pharmacol Ther. 2001; 15:2027-2039.

"Effects of Morin on an Experimental Model of Acute Colitis in Rats" by Ocete, et al., Pharmacology, 1998; 57:261-270.

"Protective effect of melatonin in a non-septic shock model induced by zymosan in the rat" by Cuzzocrea, et al., J. Pineal Res., 1998; 25:24-33.

"Antiinflammtory effects of *Cordia myxa* Fruit on Experimentally Induced Colitis in Rats" by Al-Awadi, et al., Nutrition, 17:391-396, 2001.

"Efficacy of use of colonoscopy in dextran sulfate sodium induced ulcerative colitis in rats: the evaluation of the effects of antioxidant by colonoscopy" by Ahn, et al., Int J Colorectal Dis (2001) 16:174-181.

"Taurine Can Ameliorate Inflammatory Bowel Disease in Rats" by Son, et al., Taurine 3, Edited by Stephen Schaffer, John B. Lombardini and Ryan J. Huxtable, Plenum Press, New York, 1998, pp. 291-298.

"Simvastatin ameliorates injury in an experimental model of lung ischemia-reperfusion" by Naidu, et al., The Journal of Thoracic and Cardiovascular Surgery, Aug. 2003, pp. 482-489.

"Protective Effect of Famotidine, Omeprazole, and Melatonin Against Acetylsalicylic Acid-Induced Gastric Damage in Rats" by Sener-Muratoglu, et al., Digestive Diseases and Sciences, vol. 46, No. 2, Feb. 2001, pp. 318-330.

Supplementary Partial European Search Report dated May 31, 2007.

"Association of Nitrotyrosine Levels With Cardiovascular Disease and Modulation by Statin Therapy" by Shishehbor, et al., JAMA, Apr. 2, 2003, vol. 289, No. 13, pp. 1675-1680.

"Associations between change in C-reactive protein and serum lipids during statin treatment" by Standberg, et al., The Finnish Medical Society Duodecim, Ann Med 2000; 32:579-583.

"Effects of Low Doses of Simvastatin and Atorvastatin on High-Density Lipoprotein Cholesterol Levels in Patients with Hypercholesterolernia" by Branchi, et al., Clinical Therapeutics, vol. 23, No. 6, 2001, pp. 851-857.

"Modification of Proteins and Lipids by Myeloperoxidase" by Hazen, et al., Methods in Enzymology, vol. 300, 1999, pp. 88-105.

"Mechanisms of oxidative damage by myeloperoxidase in atherosclerosis and other inflammatory disorders" by Heinecke, et al., J Lab Clin Med 1999;133:321-5.

"The oxidative modification hypothesis of atherogenesis: an overview" by Chisolrn, et al., Free Radical Biology & Medicine, vol. 28, No. 12, pp. 1815-1826, 2000.

"Myeloperoxidase binds to low-density lipoprotein: potential implications for atherosclerosis" by Carr, et al., FEBS Letters 487 (2000) 176-180.

Abstract "Elevated Levels of Plasma Myeloperoxidase, an Oxidative Enzyme Degranulated from Activated Phagocytes, in Patients with Coronary Artery Disease and Acute Coronary Syndromes" by Sugiyama, et al., Supplement to Circulation, vol. 106, No. 19, Nov. 5, 2002.

"Myeloperoxidase serum levels predict risk in patients with acute coronary syndromes" by Baldus, et al., Circulation, vol. 108, published online Sep. 2, 2003, pp. 1440-1445.

"Intracellular neutrophil myeloperoxidase is reduced in unstable angina and acute myocardial infarction, but its reduction is not related to ischemia" by Biasucci, et al., J Amer Coll Cardiol, vol. 27, No. 3, pp. 611-616.

"Defects in leukocyte-mediated initiation of lipid peroxidation in plasma as studied in myeloperoxidase-deficient subjects: systematic identification of multiple endogenous diffusible substrates for myeloperoxidase in plasma" by Zhang, et al., Blood, vol. 99, No. 5, pp. 1802-1810, 2002.

"Thrombosis and Acute Coronary-Artery Lesions in Sudden Cardiac Ischemic Death" by Davies, et al. N. Engl J Med 1984;310:1137-40.

"Increased Neutrophil Elastase Release in Unstable Angina Pectoris and Acute Myocardial Infarction" by Dinerman, et al., J Am Coll Cardiol 1990;15:1559-63.

"Neutrophil Infiltration of Culprit Lesions in Acute Coronary Syndromes" by Naruko, et al., Circulation, 2002;106:2894-2900.

"Widespread Coronary Inflammation in Unstable Angina" by Buffon, et al.; N Engl J Med 2002;347:5-12.

"Myeloperoxidase-generated reactive nitrogen species convert LDL into an atherogenic form in vitro" by Podrez, et al., J. Clin. Invest. 103:1547-1560 (1999).

"Myeloperoxidase Functions as a Major Enzymatic Catalyst for Initiation of Lipid Peroxidation at Sites of Inflammation" by Zhang, et al., The Journal of Biological Chemistry, Vol. 277, No. 48, Nov. 29, 2002, pp. 46116-46122.

U.S. Appl. No. 10/972,058, filed Oct. 22, 2004, entitled: Assessing the Risk of a Major Cardiac Event in Patients with Chest Pain.

"3-Nitrotyrosine in the proteins of human plasma determined by an ELISA method" by Khan, et al., Biochem J. (1998) 330, 795-801.

"Extensive Nitration of Protein Tyrosines in Human Atherosclerosis Detected by Immunohistochemistry" by Beckmann, et al., Biol. Chem. Hoppe-Seyler, vol. 35, pp. 81-88, Feb. 1994.

"Do Human Atherosclerotic Lesions Contain Nitrotyrosine?" by Evans, et al., Biochemical and Biophysical Research Communications, 226, 346-351 (1996).

"Formation of Nitric Oxide-Derived Oxidants by Myeloperoxidase in Monocytes: Pathways for Monocyte-Mediated Protein Nitration and Lipid Peroxidation in Vivo" by Hazen, et al., Circ. Res. 1999;85:950-958.

International Preliminary Examination Report dated Aug. 23, 2004.

International Search Report dated Jul. 2, 2004.

"Extensive tyrosine nitration in human myocardial inflammation: Evidence for the presence of peroxynitrite" by Kooy, et al., Crit Care Med, vol. 25(5) May 1997, 812-819.

"Reacitve Nitrogen Inteermediates Promote Low Density Lipoprotein Oxidation in Human Atherosclerotic Intima" by Leeuwenburgh, et al., The Journal of Biological Chemistry, vol. 272, No. 3, Jan. 17, 1997, pp. 1433-1436.

"Nitrotyrosine Bound to Beta-VLDL-Apoproteins: A Biomarker of Peroxynitrite Formation in Experimental Atherosclerosis" by Moriel, et al., Biochemical and Biophysical Research Communications, 232, 332-335 (1997).

"How urine analysis reflects oxidative stress - nitrotyrosine as a potential marker" by Schwemmer, et al.

Non-Final Office Action mailed on Sep. 21, 2007, for U.S. Appl. No. 11/313,012 filed Dec. 20, 2005.

Response/Amendment dated Mar. 19, 2008, in response to Non-Final Office Action mailed on Sep. 21, 2007, for U.S. Appl. No. 11/313,012 filed Dec. 20, 2005.

Final Office Action mailed on Aug. 19, 2008, for U.S. Appl. No. 11/313,012 filed Dec. 20, 2005.

Supplementary European Search Report dated Jan. 29, 2004 from 02718773.1.

Certified Translation of WO 02/50550.

Office Action from U.S. Appl. No. 10/039,753 dated Mar. 24, 2005.
Response from U.S. Appl. No. 10/039,753 dated Jun. 22, 2005.
Office action from U.S. Appl. No. 10/039,753 dated Sep. 8, 2005.
Response from U.S. Appl. No. 10/039,753 dated Nov. 30, 2005.
Office Action from U.S. Appl. No. 10/039,753 dated Mar. 10, 2006.
Response from U.S. Appl. No. 10/039,753 dated Apr. 7, 2006.
Interview Summary from U.S. Appl. No. 10/039,753 dated Apr. 14, 2006.
Statement of the Substance of the Interview from U.S. Appl. No. 10/039,753 dated May 3, 2006.
Final Office Action from U.S. Appl. No. 10/039,753 dated Jul. 3, 2006.
Response from U.S. Appl. No. 10/039,753 dated Jul. 26, 2006.
Office Action from U.S. Appl. No. 10/039,753 dated Aug. 17, 2006.
Response from U.S. Appl. No. 10/039,753 dated Sep. 6, 2006.
Final Office Action from U.S. Appl. No. 10/039,753 dated Nov. 22, 2006.
Response from U.S. Appl. No. 10/039,753 dated Dec. 7, 2006.
Advisory Action from U.S. Appl. No. 10/039,753 dated Dec. 28, 2006.
Response from U.S. Appl. No. 10/039,753 dated Jan. 3, 2007.
Advisory Action from U.S. Appl. No. 10/039,753 dated Feb. 21, 2007.
Response from U.S. Appl. No. 10/039,753 dated Feb. 28, 2007.
Interview Summary from U.S. Appl. No. 10/039,753 dated Mar. 2, 2007.
Notice of Allowance from U.S. Appl. No. 10/039,753 dated Mar. 19, 2007.

Non-Final Office Action mailed on Sep. 21, 2007, for U.S. Appl. No. 11/313,012.

Response/Amendment dated Mar. 19, 2008, in response to Non-Final Office Action mailed on Sep. 21, 2007, for U.S. Appl. No. 11/313,012.

Final Office Action mailed on Aug. 19, 2008, for U.S. Appl. No. 11/313,012.

Amendment/Response dated Jan. 21, 2009 in response to Final Office action mailed on Aug. 19, 2008 for U.S. Appl. No. 11/313,012.

Davies, et al., "Stable markers of oxidant damage to proteins and their application in the study of human disease", Free Radio Biol Med 27: 1151-1163 (1999).

Brennan et al. "A Tale of Two Controversies. Defining Both the Role of Peroxidases in Nitrotyrosine Formation in Vivo Using Eosinophil Peroxidase and Myeloperoxidase-Deficient Mice, and the Nature of Peroxidase-Generated Reactive Nitrogen Species", The Journal of Biological Chemistry vol. 277, No. 20, Issue of May 17, pp. 17415-17427 (2002).

Francis, et al., "Oxidative tyrosylation of high density lipoproteins by peroxidase enhances cholesterol removal from cultured fibroblasts and macrophage foam cells", Proc. Natl. Acad Sci, USA, 90: pp. 6631-6634 (1993).

Heinecke et al., "Tyrosyl radical production by myeloperoxidase: A phagocyte pathway for lipid peroxidation and dityrosine cross-linking of proteins", Toxicology 177: 11-22 (2002).

Leewenburgh et al., "Mass spectrometric quantification of markers for protein oxidation by tyrosyl radical, copper, and hydroxyl radical in low desnity lipoproteins isolated from human atherosclerotic plaques", J Biol Chem 272: 3520-3526 (1997).

Brennan et al., "Amino acid and protein oxidation in cardiovascular disease", Amino Acids, 25: pp. 365-374 (2003).

Japanese Office Action, Mailed Jan. 27, 2009, for Japanese Patent Application No. 2003-585569, entitled "Systemic Marker for Monitoring Anti-Inflammatory and Antioxidant Actions of Therapeutic Agents." (English Translation).

Japanese Office Action, Mailed Sept. 11, 2009, for Japanese Patent Application No. 2003-585569, entitled "Systemic Marker for Monitoring Anti-Inflammatory and Antioxidant Actions of Therapeutic Agents." (English Translation).

* cited by examiner

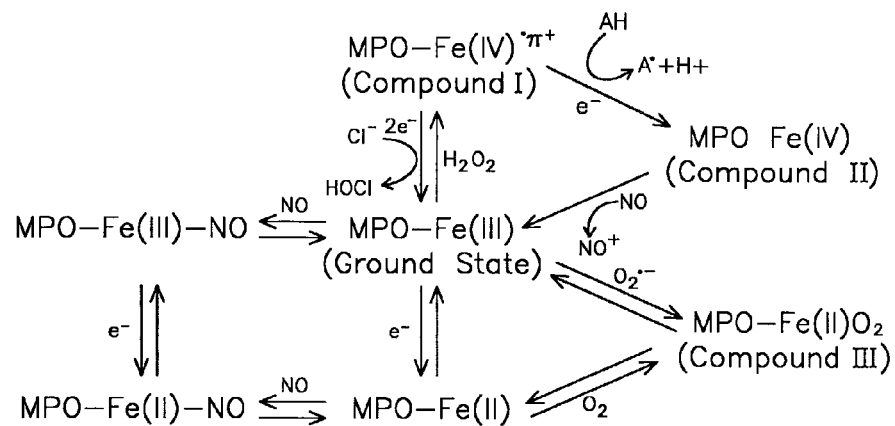
Fig.1
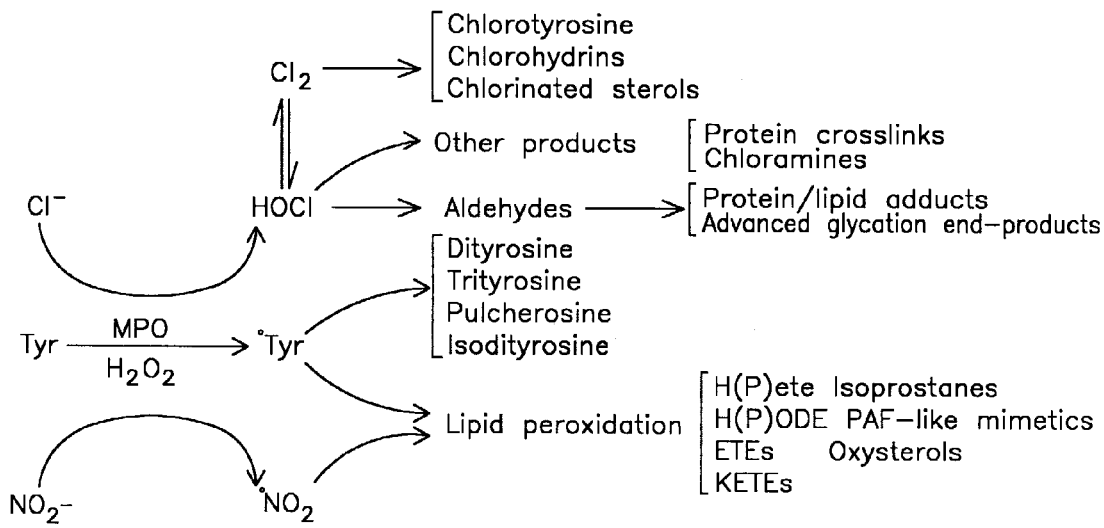
Fig.2
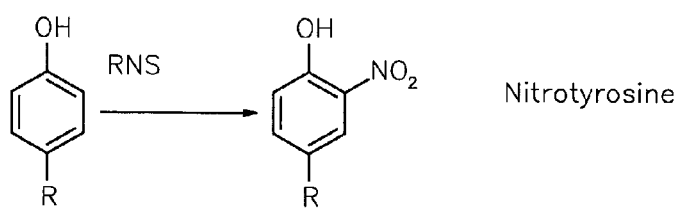
Nitrotyrosine
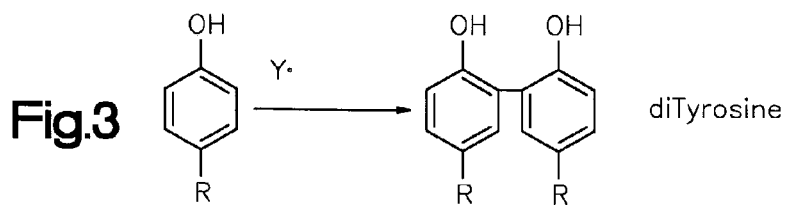
Fig.3    diTyrosine

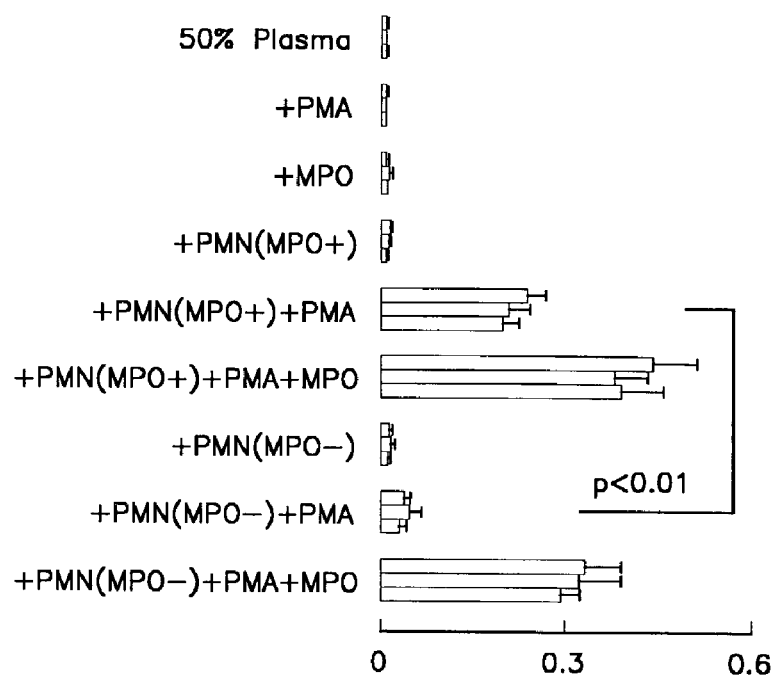
Fig.4A  9-H(P)ODE (μg/ml)
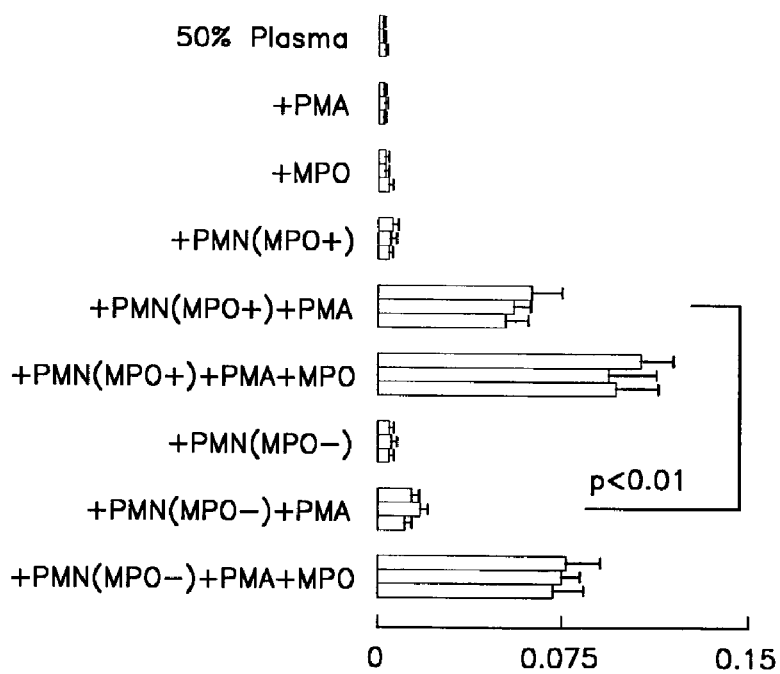
Fig.4B  9-H(P)ETE (μg/ml)

SYSTEMIC MARKER FOR MONITORING ANTI-INFLAMMATORY AND ANTIOXIDANT ACTIONS OF THERAPEUTIC AGENTS

The present application claims priority to U.S. Provisional Application No. 60/373,113 filed Apr. 17, 2002 and is a continuation-in-part of U.S. patent application Ser. No. 10/039,753, which was filed Jan. 2, 2002, now U.S. Pat. No. 7,223,552 both of which are incorporated herein by reference in their entirety.

The work described in this application was supported, at least in part, by Grant No. HL70621, HL62526, HL61878 from the National Institute of Health. The United States government has certain rights in this invention.

FIELD OF THE INVENTION

The present invention relates to a diagnostic method of monitoring anti-inflammatory and antioxidant actions. More particularly, the present invention relates to a diagnostic method that can be used to monitor the anti-inflammatory and antioxidant actions of therapeutic agents.

BACKGROUND OF THE INVENTION

Oxidative damage of biomolecules, such as proteins, lipids, and nucleic acids, has been implicated in diseases ranging from atherosclerosis to ischemia-reperfusion injury to cancer. For example, a wealth of evidence establishes that enhanced oxidant stress occurs within the artery wall of atherosclerotic vessels. Multiple distinct oxidation products are enriched within human atherosclerotic plaques, as well as low density lipoprotein (LDL) recovered from diseased v. normal human aorta.

The role of oxidation in the pathogenesis of coronary artery disease (CAD) has been questioned because of the failures of multiple prospective intervention trials with antioxidant supplements (e.g., alpha tocopherol (vitamin E)). It should be noted, however, that none of the major antioxidant trials to date concomitantly measured systemic markers of oxidant stress to ensure an effect on the process targeted for intervention (i.e., oxidation). This is particularly relevant since the oxidation pathways known to occur within the human atheroma are in large part not effectively inhibited by alpha tocopherol, the major antioxidant supplement in these trials. Moreover, under certain conditions, pro- rather than antioxidant actions for species like alpha tocopherol and ascorbate (vitamin C) have been documented.

Much of what is known about the pathways responsible for oxidative injury within the atherosclerotic vessels has been gained by the detection of stable structurally informative oxidation products that convey information regarding the oxidation pathway(s) responsible for their generation. These pathways have been shown to participate in oxidative conversion of LDL into an atherogenic particle, initiation of lipid peroxidation, consumption of nitric oxide potentially, leading to endothelial dysfunction, and activation of matrix metalloprotease and alternative protease cascades, potentially leading to vulnerable plaque. Remarkably, alpha tocopherol is relatively ineffective in blocking these oxidation pathways.

3-Hydroxymethyl-3-methylglutaryl coenzyme A reductase inhibitors (statins) are recognized as having potential utility in a wide variety of inflammatory and immunological disorders unrelated to their lipid lowering effects. These so called pleiotropic effects of statins are believed to include anti-inflammatory and antioxidant actions. The only published markers for monitoring statin anti-inflammatory action are non-specific markers of inflammation, such as C-Reactive Protein (CRP). The levels of CRP only change minimally in response to statin therapy, and it is widely appreciated that alternative markers are neededed to monitor the anti-inflammatory and antioxidant actions of statins.

SUMMARY OF THE INVENTION

The following presents a simplified summary of the invention in order to provide a basic understanding of some aspects of the invention. This summary is not an extensive overview of the invention. It is intended to neither identify key or critical elements of the invention nor delineate the scope of the invention. Its sole purpose is to present some concepts of the invention in a simplified form as a prelude to the more detailed description that is presented later.

The present invention relates generally to a diagnostic method of monitoring anti-inflammatory and/or antioxidant actions of therapeutic agents. The method comprises determining the level of at least one systemic marker indicative of inflammation or oxidation in a bodily sample taken from a subject at baseline or following administration of the therapeutic agent. The marker can include MPO activity, MPO mass, select MPO-generated oxidation products, and combinations thereof. The level of the marker in the bodily sample can be compared with a predetermined value to monitor the anti-inflammatory and/or antioxidant actions of the therapeutic agent.

In one aspect, the predetermined value can be determined from the level of marker in a bodily sample that was taken from the subject prior to administration of the therapeutic agent. A decrease in the level of the marker in the sample taken after or during administration of the therapeutic agent as compared to the level of the marker in the sample taken before administration of the therapeutic agent indicates that the therapeutic agent provides an anti-inflammatory and/or antioxidant effect in the treated subject.

The method can be especially useful for monitoring the anti-inflammatory and/or antioxidant actions of therapeutic agents administered to individuals to treat disorders where inflammation and/or oxidative damage is linked to pathogenesis of the disorder. These disorders can include but are not limited to inflammatory and autoimmune disorders, such as cardiovascular disease (CVD), Alzheimer's disease, multiple sclerosis, autoimmune diseases (e.g., rheumatoid arthritis and vasculitis), aortic stenosis, hypertension, and cancer. These disorders can also result from treatments, such as organ transplantation.

In another aspect, the method comprises determining the level of MPO activity in a bodily sample obtained from the individual or test subject at baseline or following administration of the therapeutic agent. The bodily sample is blood or a derivative thereof, including but not limited to, leukocytes, neutrophils, monocytes, serum, or plasma. The level of MPO activity in the bodily sample from the test subject can then be compared to a predetermined value that can be derived from measurements of MPO activity in a bodily sample obtained from the subject prior to or following the administration of the therapeutic agent.

In another aspect, the method comprises determining the level of MPO mass in a bodily sample obtained from the test subject at baseline or following adminstration of the therapeutic agent. The bodily sample can be blood or a derivative thereof, including but not limited to, leukocytes, neutrophils, monocytes, serum, or plasma. Levels of MPO mass in bodily samples from the test subject are then compared to a predetermined value that can be derived from measurements of MPO mass obtained from the subject prior to or following the administration of the therapeutic agent.

In another aspect, the method comprises determining the level of one or more select MPO-generated oxidation products in a bodily sample obtained from the test subject at baseline or following administration of the therapeutic agent. The select MPO-generated oxidation products are chlorotyrosine, dityrosine, nitrotyrosine, methionine sulphoxide, homocitrulline (i.e., cabamyl-lysine) and MPO-generated lipid peroxidation products. Preferred MPO lipid peroxidation products can include hydroxy-eicosatetraenoic acids (HETEs); hydroxy-octadecadienoic acids (HODEs); $F_2$Isoprostanes; the glutaric and nonanedioic monoesters of 2-lysoPC (G-PC and ND-PC, respectively); the 9-hydroxy-10-dodecenedioic acid and 5-hydroxy-8-oxo-6-octenedioic acid esters of 2-lysoPC (HDdiA-PC and HOdiA-PC, respectively); the 9-hydroxy-12-oxo-10-dodecenoic acid and 5-hydroxy-8-oxo-6-octenoic acid esters of 2-lysoPC(HODA-PC and HOOA-PC, respectively); the 9-keto-12-oxo-10-dodecenoic acid and 5-keto-8-oxo-6-octenoic acid esters of 2-lysoPC (KODA-PC and KOOA-PC, respectively); the 9-keto-10-dodecendioic acid and 5-keto-6-octendioic acid esters of-2-lysoPC (KDdiA-PC and KOdiA-PC, respectively); the 5-oxovaleric acid and 9-oxononanoic acid esters of 2-lysoPC (OV-PC and ON-PC, respectively); 5-cholesten-5α,6α-epoxy-3β-ol (cholesterol α-epoxide); 5-cholesten-5β,6β-epoxy-3β-ol (cholesterol β-epoxide); 5-cholesten-3β,7β-diol (7-OH-cholesterol); 5-cholesten-3β,25-diol (25-OH cholesterol); 5-cholesten-3β-ol-7β-hydroperoxide (7-OOH cholesterol); and cholestan-3β,5α,6β-triol (triol). The bodily sample can be blood, urine or a blood derivative, including but not limited to, leukocytes, neutrophils, monocytes, serum, or plasma. Levels of the selected MPO-generated oxidation products in bodily samples from the test subject are then compared to a predetermined value that can be derived from measurements of the selected MPO-generated oxidation products in comparable bodily samples obtained from the subject prior to or following the administration of the therapeutic agent.

In yet another aspect, the method includes selecting a therapeutic agent for treating diseases where inflammation and/or oxidative damage is linked to pathogenesis of the disorder, administering the therapeutic agent to the subject, and monitoring the level of at least one systemic marker indicative of inflammation and/or oxidation in the subject at baseline, during, or following administration of the therapeutic agent to determine a dosage of the therapeutic agent effective to provide a medically desirable result. The marker can include MPO activity, MPO mass, select MPO-generated oxidation products, and combinations thereof. The method can be especially useful where the disease is a cardiovascular disease, such as atherosclerosis, and the therapeutic agent is a lipid lower agent, such as a hydroxymethylglutaryl CoA reductase inhibitor.

BRIEF DESCRIPTION OF THE FIGURES

Further features of the present invention will become apparent to those skilled in the art to which the present invention relates from reading the following description of the invention with reference to the accompanying drawings in which:

FIG. 1 is a schematic representation of a kinetic model for myeloperoxidase.

FIG. 2 is a schematic representation of certain myeloperoxidase generated reactive intermediates and some MPO-generated oxidation products.

FIG. 3 shows the chemical structure of dityrosine and nitrotyrosine.

FIGS. 4(A-B) are graphs illustrating Lipid Peroxidation in Plasma with Neutrophils from Healthy Subjects and MPO Deficient Subjects. Neutrophils ($1 \times 10^6$/ml) isolated from normal and MPO-deficient individuals were incubated at 37° C. in HBSS supplemented with DTPA (100 μM, pH 7.0) and fresh human plasma (50% v/v). Cells were activated by addition of phorbol myristate acetate (PMA, 200 nM) and incubated for 2 h (Complete System). The content of 9-H(P)ODE and 9-H(P)ETE formed within endogenous plasma lipids were then determined by LC/ESI/MS/MS. Where indicated, human MPO (30 nM) was added to reaction mixtures. Data represent the mean±SD of triplicate determinations. Each bar within a cluster for a given condition represents results obtained from independent experiments performed with neutrophil preparations from a distinct donor. PMN(MPO+), neutrophils isolated from normal subjects; PMN(MPO), neutrophils isolated from MPO-deficient subjects.

DETAILED DESCRIPTION OF THE INVENTION

Figure 5A:
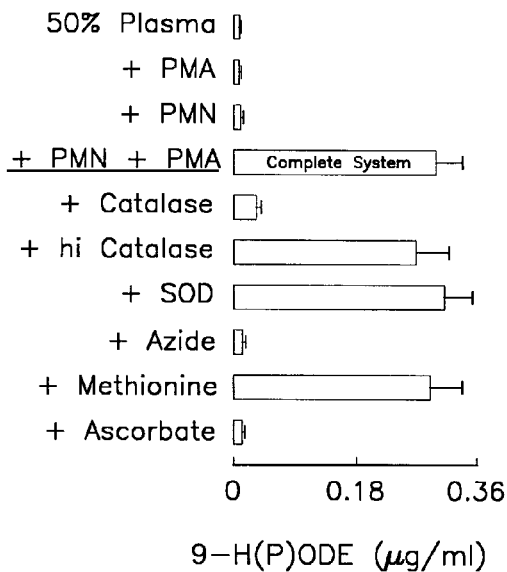
FIGS. 5(A-B) are graphs showing the characterization of neutrophil-dependent initiation of lipid peroxidation of endogenous plasma lipids. Neutrophils ($1 \times 10^6$/ml) isolated from normal subjects (PMN) were incubated at 37° C. in HBSS supplemented with DTPA (100 μM, pH 7.0) and fresh human plasma (50% v/v). Cells were activated by addition of phorbol myristate acetate (PMA, 200 nM) and then incubated for 2 h (Complete System). The content of 9-H(P)ODE and 9-H(P)ETE formed within endogenous plasma lipids were then determined by LC/ESI/MS/MS. Additions or deletions to the Complete System were as indicated. The final concentrations of additions to the Complete System were 30 nM human MPO, 1 mM $NaN_3$, 300 nM catalase (Cat), 300 nM heat inactivated-catalase (hiCat), 100 μM methionine (Met), 100 μM ascorbate and 10 μg/ml superoxide dismutase (SOD). Data represent the mean±SD of three independent experiments.

All references cited herein are specifically incorporated herein by reference.

The present invention relates generally to a diagnostic method of monitoring anti-inflammatory and/or antioxidant actions of therapeutic agents. The present diagnostic method is based on the discovery that certain therapeutic agents (e.g., statins) when administered to a subject can promote potent systemic anti-inflammation and antioxidant effects in vivo through suppression of multiple distinct oxidation pathways. The major pathways can include the formation of mycloperoxidase and/or nitric oxide derived oxidants. The levels of mycloperoxidase and myeloperoxidase catalyzed oxidation products can serve as systemic markers for monitoring the anti-inflammatory and antioxidant actions of therapeutic agents.

In one aspect, the method comprises determining the level of MPO activity in a bodily sample obtained from the individual. In another aspect, the method comprises determining the level of MPO mass in a bodily sample obtained from the individual. In another aspect, the method comprises determining the level of one or more select MPO-generated oxidation products in a bodily sample obtained from the individual or test subject. Such MPO-generated oxidation products can include at least one of chlorotyrosine, dityrosine, nitrotyrosine, methionine sulphoxide and a lipid peroxidation product. In yet another aspect, the method comprises determining the level of MPO activity, or MPO mass, or both, or the level of one or more select MPO-generated oxidation products in a bodily sample obtained from the individual.

The level of MPO activity or MPO mass or select MPO-generated oxidation product in the individual's bodily sample can then compared to a predetermined value to monitor the anti-inflammation and/or antioxidant actions of the therapeutic agent.

The present invention also relates to kits that comprise assays for MPO activity or mass, or the select MPO-generated oxidation product. Such assays have appropriate sensitivity with respect to predetermined values selected on the basis of the present diagnostic tests. The present kits differ from those presently commercially available for MPO by including, for example, different cut-offs, different sensitivities at particular cut-offs, as well as instructions or other printed material for characterizing the outcome of the assay.

Therapeutic Agents

Therapeutic agents that can be monitored in accordance with an aspect of the invention can include any pharmacodynamic agent that exhibits an anti-inflammation and/or anti-oxidant action in vivo through suppression of multiple distinct oxidation pathways used in the formation of mycloperoxidase and nitric oxide derived oxidants. These anti-inflammation and/or antioxidant actions can be systemic and can be monitored by monitoring the systemic levels of myeloperoxidase and/or myeloperoxidase generated oxidation products.

An example of a therapeutic agent for which the anti-inflammation and/or antioxidant action can be monitored in accordance with an aspect of the invention is an HMG CoA reductase inhibitor (3-hydroxymethylglutaryl coenzyme A reductase inhibitors)(i.e., statin). HMG-CoA (3-hydroxy methylglutaryl coenzyme A) reductase is the microsomal enzyme that catalyzes the rate limiting reaction in cholesterol biosynthesis (HMG-CoA Mevalonate). Statins inhibit HMG-CoA reductase, and as a result inhibit the synthesis of cholesterol. It is shown in Examples 14 and 15 of the present application that statins also exhibit anti-inflammatory and antioxidant actions. It is believed that these anti-inflammatory and antioxidant actions likely result from inhibition of isoprenylation of Rae and Rho. Rae is a key component of the NAD(P)H oxidase complex of both leukocytes and vascular cells. It is further believed that statin induced inhibition of Rae isoprenylation prevents its translocation to the plasma membrane, leading to suppression in superoxide formation from cells. Rho is a small GTPase involved in cell signaling. It is believed that inhibition of Rho isoprenylation results in enhanced nitric oxide production from endothelial cells, which is likely to produce an overall antioxidant action.

Statins that can be useful for administration, or co-administration with other agents according to the invention include, but are not limited to, simvastatin (U.S. Pat. No. 4,444,784), lovastatin (U.S. Pat. No. 4,231,938), pravastatin sodium (U.S. Pat. No. 4,346,227), fluvastatin (U.S. Pat. No. 4,739,073), atorvastatin (U.S. Pat. No. 5,273,995), cerivastatin, and numerous others described in U.S. Pat. Nos. 5,622,985, 5,135,935, 5,356,896, 4,920,109, 5,286,895, 5,262,435, 5,260,332, 5,317,031, 5,283,256, 5,256,689, 5,182,298, 5,369,125, 5,302,604, 5,166,171, 5,202,327, 5,276,021, 5,196,440, 5,091,386, 5,091,378, 4,904,646, 5,385,932, 5,250,435, 5,132,312, 5,130,306, 5,116,870, 5,112,857, 5,102,911, 5,098,931, 5,081,136, 5,025,000, 5,021,453, 5,017,716, 5,001,144, 5,001,128, 4,997,837, 4,996,234, 4,994,494, 4,992,429, 4,970,231, 4,968,693, 4,963,538, 4,957,940, 4,950,675, 4,946,864, 4,946,860, 4,940,800, 4,940,727, 4,939,143, 4,929,620, 4,923,861, 4,906,657, 4,906,624 and 4,897,402, the disclosures of which patents are incorporated herein by reference.

Another example of a therapeutic agent for which the anti-inflammation and/or antioxidant action can be monitored in accordance with an aspect of the invention is a cyclooxygenase-2 (COX-2) inhibitor. "Cyclooxygenase" is an enzyme complex present in most tissues that produces various prostaglandins and thromboxanes from arachidonic acid. Cox inhibitors exert most of their anti-inflammatory, analgesic and antipyretic activity and inhibit hormone-induced uterine contractions and certain types of cancer growth through inhibition of the cyclooxygenase (also known as prostaglandin GH-1 synthase and/or prostaglandinendoperoxide synthase).

COX-2 inhibitors that can be useful for administration, or co-administration with other agents according to the invention include, but are not limited to, COX-2 inhibitors described in U.S. Pat. No. 5,474,995 "Phenyl heterocycles as cox-2 inhibitors"; U.S. Pat. No. 5,521,213 "Diaryl bicyclic heterocycles as inhibitors of cyclooxygenase-2"; U.S. Pat. No. 5,536,752 "Phenyl heterocycles as COX-2 inhibitors"; U.S. Pat. No. 5,550,142 "Phenyl heterocycles as COX-2 inhibitors"; U.S. Pat. No. 5,552,422 "Aryl substituted 5,5 fused aromatic nitrogen compounds as anti-inflammatory agents"; U.S. Pat. No. 5,604,253 "N-benzylindolyl propanoic acid derivatives as cyclooxygenase inhibitors"; U.S. Pat. No. 5,604,260 "5-methanesulfonamido-1-indanones as an inhibitor of cyclooxygenase-2"; U.S. Pat. No. 5,639,780 N-benzyl indolyl butanoic acid derivatives as cyclooxygenase inhibitors"; U.S. Pat. No. 5,677,318 Diphenyl-1,2 thiadiazoles as anti-inflammatory agents"; U.S. Pat. No. 5,691,374 "Diaryl oxygenated (SH)-furanones as COX-2 inhibitors"; U.S. Pat. No. 5,698,584 "3,4-diaryl hydroxy-2,5dihydrofurans as prodrugs to COX-2 inhibitors"; U.S. Pat. No. 5,710,140 "Phenyl heterocycles as COX-2 inhibitors"; U.S. Pat. No. 5,733,909 "Diphenyl stilbenes as prodrugs to COX-2 inhibitors"; U.S. Pat. No. 5,789,413 "Allcylated styrenes as prodrags to COX-2 inhibitors"; U.S. Pat. No. 5,817,700 "Bisaryl cyclobutenes derivatives as cyclooxygenase inhibitors"; U.S. Pat. No. 5,849,943 "Stilbene derivatives useful as cyclooxygenase-2 inhibitors"; U.S. Pat. No. 5,861,419 "Substituted pyridines as selective cyclooxygenase-2 inhibitors"; U.S. Pat. No. 5,922, 742 "Pyridinyl cyclopenten-1-ones as selective cyclooxygenase-2 inhibitors"; U.S. Pat. No. 5,925,631 "Alkylated styrenes as prodrugs to COX-2 inhibitors"; all of which are commonly assigned to Merck, Inc. (Kirkland, Calif.).

Additional COX-2 inhibitors that can potentially used in accordance with invention are also described in U.S. Pat. No. 5,643,933, assigned to G. D. Searle & Co. (Skokie, Ill.), entitled: "Substituted sulfonylphenylheterocycles as cyclooxygenase-2 and 5-hpoxygenase inhibitors." A number of the above-identified COX-2 inhibitors are prodrugs of selective COX-2 inhibitors, and exert their action by conversion in vivo to the active and selective COX-2 inhibitors. The active and selective COX-2 inhibitors formed from the above-identified COX-2 inhibitor prodrugs are described in detail in WO 95/00501, published Jan. 5, 1995, WO 95/18799, published Jul. 13, 1995 and U.S. Pat. No. 5,474,995, issued Dec. 12, 1995. Given the teachings of U.S. Pat. No. 5,543,297, entitled: "Human cyclooxygenase2 cDNA and assays for evaluating cyclooxygenase-2 activity," a person of ordinary skill in the art would be able to determine whether an agent is a selective COX-2 inhibitor or a precursor of a COX-2 inhibitor, and therefore part of the present invention.

Yet another example of a therapeutic agent for which the anti-inflammation and/or antioxidant action can be monitored in accordance with an aspect of the invention is an angiotensin system inhibitor. "Angiotensin system inhibitor" refers to an agent that interferes with the function, synthesis or catabolism of angiotensin II. These agents include, but are not limited to, angiotensin-converting enzyme (ACE) inhibitors, angiotensin II antagonists, angiotensin receptor blocking agents, agents that activate the catabolism of angiotensin II, and agents that prevent the synthesis of angiotensin I from which angiotensin II is ultimately derived. The renin-angiotensin system is involved in the regulation of hemodynamics and water and electrolyte balance. Factors that lower blood volume, renal perfusion pressure, or the concentration of Na in plasma tend to activate the system, while factors that increase these parameters tend to suppress its function.

Angiotensin I and angiotensin II are synthesized by the enzymatic rennin-angiotensin pathway. The synthetic process is initiated when the enzyme renin acts on angiotensin, a pseudoglobulin in blood plasma, to produce the decapeptide angiotensin I. Angiotensin I is converted by angiotensin converting enzyme (ACE) to angiotensin II (angiotensin-[1-8] octapeptide). The latter is an active pressor substance, which has been implicated as a causative agent in several forms of hypertension in various mammalian species, e.g., humans.

Angiotensin (renin-angiotensin) system inhibitors are compounds that act to interfere with the production of angiotensin II from angiotensin or angiotensin I or interfere with the activity of angiotensin II. Such inhibitors are well known to those of ordinary skill in the art and include compounds that act to inhibit the enzymes involved in the ultimate production of angiotensin II, including renin and ACE. They also include compounds that interfere with the activity of angiotensin II, once produced. Examples of classes of such compounds include antibodies (e.g., to renin), amino acids and analogs thereof (including those conjugated to larger molecules), peptides (including peptide analogs of angiotensin and angiotensin I), pro-renin related analogs, etc. Among the most potent and useful renin-angiotensin system inhibitors are renin inhibitors, ACE inhibitors, and angiotensin II antagonists.

"Angiotensin receptor blocking agents" are compounds which interfere with the activity of angiotensin II by binding to angiotensin II receptors and interfering with its activity. Angiotensin receptor blocking agents are well known and include peptide compounds and non-peptide compounds. Most angiotensin receptor blocking agents are slightly modified congeners in which agonist activity is attenuated by replacement of phenylalanine in position 8 with some other amino acid; stability can be enhanced by other replacements that slow degeneration in vivo.

Examples of angiotensin I blocking receptor agents include: peptidic compounds (e.g., saralasin, [(San')(Val') (Ala')] angiotensin-(1-8) octapeptide' and related analogs); N-substituted imidazole one (U.S. Pat. No. 5,087,634); imidazole acetate derivatives including 2N-butyl chloro-1-(2-chlorobenzile) imidazole acetic acid (see Long et al., J PharmacoL Exp. Ther. 247(1), 1-7 (1988)); 4,5,6,7-tetrahydro-1H-imidazo[4,5-c] pyridine carboxylic acid and analog derivatives (U.S. Pat. No. 4,816,463); N2-tetrazole betaglucuronide analogs (U.S. Pat. No. 5,085,992); substituted pyrroles, pyrazoles, and tryazoles (U.S. Pat. No. 5,081,127); phenol and heterocyclic derivatives such as 1,3imidazoles (U.S. Pat. No. 5,073,566); imidazo-fased 7-member ring heterocycles (U.S. Pat. No. 5,064,825); peptides (e.g., U.S. Pat. No. 4,772,684); antibodies to angiotensin 11 (e.g., U.S. Pat. No. 4,302,386); and arallcylimidazole compounds such as biphenyl-methyl substituted imidazoles (e.g., EP Number 253,310, Jan. 20, 1988); ES8891 (N-morpholinoacetyl-(-1-naphthyl)-L-alanyl-(4, thiazolyl)-L-alanyl (35, 45) ainino hydroxy cyclo-hexapentanoyl-N-hexylamide, Sanlcyb Company, Ltd., Tokyo, Japan); SKF1085 66 (E-alpha [2-butyl-1-(carboxy phenyl) methyl] 1H-imidazolyl[methylane] thiophenepropanoic acid, Smith Kline Beecham Pharmaceuticals, PA); Losartan (DUP753/MK954, DuPont Merck Pharmaceutical Company); Remildrin (RO425 8 92, F. Hoffman LaRoche AG); A2 agonists (Marion Merrill Dow) and certain non-peptide heterocycles (G. D. Searle and Company). "Angiotensin converting enzyme" (ACE), is an enzyme which catalyzes the conversion of angiotensin I to angiotensin II. ACE inhibitors include amino acids and derivatives thereof, peptides, including di- and tri-peptides and antibodies to ACE which intervene in the renin-angiotensin system by inhibiting the activity of ACE thereby reducing or eliminating the formation of pressor substance angiotensin II. ACE inhibitors have been used medically to treat hypertension, congestive heart failure, myocardial infarction and renal disease. Classes of compounds known to be useful as ACE inhibitors include acylmercapto and mercaptoalkanoyl prolines such as captopril (U.S. Pat. No. 4,105,776) and zofenopril (U.S. Pat. No. 4,316,906), carboxyalkyl. dipeptides such as enalapril (U.S. Pat. No. 4,374,829), lisinopril (U.S. Pat. No. 4,374,829), quinapril (U.S. Pat. No. 4,344,949), ramipril (U.S. Pat. No. 4,587,258), and perindopril (U.S. Pat. No. 4,508,729), carboxyallcyl dipeptide mimics such as cilazapril (U.S. Pat. No. 4,512,924) and benazapril (U.S. Pat. No. 4,410, 520), phosphinylalkanoyl prolines such as fosinopril (U.S. Pat. No. 4,337,201) and trandolopril.

Yet other examples of a therapeutic agents for which the anti-inflammation and/or antioxidant actions can be monitored in accordance with an aspect of the invention can include but are not limited to anti-inflammatory agents, such as cytokine inhibitors (e.g., IL-6 receptor antagonists), tumor necrosis factor-u, (TNF-α) inhibitors, (e.g., Etanercept (ENBREL, Immunex, Seattle) and Infliximab (REMICADEO, Centocor, Malvern, Pa.)), antihyperlipoproteinemics, inhibitors of cholesterol biosynthesis (besides statins), insulin sensitizing agents, antihypertensive agents, such as Beta-adrenergic receptor blocking agents, anti-thrombotic agents, anti-platelet agents, fibrinolytic agents, direct thrombin inhibitors, ACAT inhibitors, CETP inhibitors, V-CAM inhibitors (e.g., V-PROTECTANTS, Atherogenics, Inc., Alpharetta, Ga., U.S. Pat. No. 6,147,250), immunomodulating agents (e.g., agents that reduce organ transplantation rejection), thiazolidinediones (i.e., PPAR agonists), such as rosiglitazone (Avandia) and pioglitazone (Actos), and glycoprotein IIb/IIIa receptor inhibitors.

When administered, the therapeutic agents of the invention can be applied in pharmaceutically-acceptable amounts and in pharmaceutically-acceptable compositions. Such preparations may routinely contain salt, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from the following acids: hydrochloric, hydrobromic, sulfuric, nitric, phosphoric, maleic, acetic, salicylic, salts can be prepared as alkaline metal or alkaline earth salts, such as sodium, potassium or calcium salts.

The therapeutic agents of the invention may be combined, optionally, with a pharmaceutically acceptable carrier. The term "pharmaceutically-acceptable carrier" as used herein means one or more compatible solid or liquid filler, diluents or encapsulating substances, which are suitable for administration into a human. The term "carrier" denotes an organic or inorganic ingredient, natural or synthetic, with which the active ingredient is combined to facilitate the application. The components of the pharmaceutical compositions also are capable of being co-mingled with the molecules of the present invention, and with each other, in a manner such that there is no interaction which would substantially impair the desired pharmaceutical efficacy.

The pharmaceutical compositions may contain suitable buffering agents, including acetic acid in a salt, citric acid in a salt, boric acid in a salt, and phosphoric acid in a salt. The pharmaceutical compositions also may contain, optionally, suitable preservatives, such as chlorobutanol, parabens, and thimerosal.

Compositions suitable for parenteral administration conveniently comprise a sterile aqueous preparation of the agent of choice, which is preferably isotonic with the blood of the recipient. This aqueous preparation may be formulated according to known methods using suitable dispersing or wetting agents and suspending agents. The sterile injectable preparation also may be a sterile injectable solution or suspension in a non-toxic parenterally-acceptable diluent or solvent, for example, as a solution in 1,3-butane diol.

Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or di-glycerides. In addition, fatty acids such as oleic acid may be used in the preparation of injectables. Carrier formulation suitable for oral, subcutaneous, intravenous, intramuscular, etc. administrations can be found in Remington's Pharmaceutical Sciences, Mack Publishing Co., Easton, Pa.

A variety of administration routes are available. The particular mode selected will depend, of course, upon the particular therapeutic agent selected, the severity of the condition being treated and the dosage required for therapeutic efficacy. The methods of the invention, generally speaking, may be practiced using any mode of administration that is medically acceptable, meaning any mode that produces effective levels of the active compounds without causing clinically unacceptable adverse effects. Such modes of administration include oral, rectal, topical, nasal, intradermal, or parenteral routes. The term "parenteral" includes subcutaneous, intravenous, intramuscular, or infusion. Intravenous or intramuscular routes are not particularly suitable for long-term therapy and prophylaxis.

The pharmaceutical compositions may conveniently be presented in unit dosage form and may be prepared by any of the methods well-known in the art of pharmacy. All methods include the step of bringing the agent into association with a carrier which constitutes one or more accessory ingredients. In general, the compositions are prepared by uniformly and intimately bringing the therapeutic agent into association with a liquid carrier, a finely divided solid carrier, or both, and then, if necessary, shaping the product.

Compositions suitable for oral administration may be presented as discrete units, such as capsules, tablets, lozenges, each containing a predetermined amount of the anti-inflammatory agent. Other compositions include suspensions in aqueous liquids or nonaqueous liquids such as a syrup, elixir or an emulsion.

Other delivery systems can include time-release, delayed release or sustained release delivery systems. Such systems can avoid repeated administrations of an agent of the present invention, increasing convenience to the subject and the physician. Many types of release delivery systems are available and known to those of ordinary skill in the art. They include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono- di- and tri-glycerides; hydrogel release systems; sylastic systems; peptide based systems; wax coatings; compressed tablets using conventional binders and excipients; partially fused implants; and the like. Specific examples include, but are not limited to: (a) erosional systems in which an agent of the invention is contained in a form within a matrix such as those described in U.S. Pat. Nos. 4,452,775, 4,675,189, and 5,736,152, and (b) diffusional systems in which an active component permeates at a controlled rate from a polymer such as described in U.S. Pat. Nos. 3,854,480, 5,133,974 and 5,407,686. In addition, pump-based hardware delivery systems can be used, some of which are adapted for implantation.

Use of a long-term sustained release implant may be desirable. Long-term release as used herein, means that the implant is constructed and arranged to deliver therapeutic levels of the active ingredient for at least 30 days, and preferably 60 days. Long-term sustained release implants are well-known to those of ordinary skill in the art and include some of the release systems described above. Specific examples include, but are not limited to, long-term sustained release implants described in U.S. Pat. No. 4,748,024, and Canadian Patent No. 1330939.

The therapeutic agent of the invention can be administered by itself, or co-administered in combination with other agents of the invention. "Co-administering," as used herein, refers to administering simultaneously two or more compounds of the invention, as an admixture in a single composition, or sequentially, close enough in time so that the compounds may exert an additive or even synergistic effect, i.e., on reducing the risk of developing diabetes or diabetic complications.

Preparation of Bodily Sample

The bodily sample in the diagnostic method can include, for example, whole blood, blood plasma, blood serum, urine, or body tissue or cells. The whole blood can be obtained from the individual or test subject using standard clinical procedures. Plasma can be obtained from whole blood samples by centrifugation of anti-coagulated blood. Such process provides a buffy coat of white cell components and a supernatant of the plasma.

Serum can be collected by centrifugation of whole blood samples that have been collected in tubes that are free of anti-coagulant. The blood is permitted to clot prior to centrifugation. The yellowish-reddish fluid that is obtained by centrifugation is the serum.

Leukocytes can be isolated from whole blood samples by any of various techniques including buoyant density centrifugation as described in the examples below.

Myeloperoxidase and Myeloperoxidase-Generated Oxidation Products

MPO (donor: hydrogen peroxide, oxidoreductase, EC 1.11.1.7) is a tetrameric, heavily glycosylated, basic (PI. 10) heme protein of approximately 150 kDa. It is comprised of two identical disulfide-linked protomers, each of which possesses a protoporphyrin-containing 59-64 kDa heavy subunit and a 14 kDa light subunit (Nauseef, W. M, et al., *Blood* 67:1504-1507; 1986.).

MPO is abundant in neutrophils and monocytes, accounting for 5%, and 1 to 2%, respectively, of the dry weight of these cells (Nauseef, W. M, et al., *Blood* 67:1504-1507; 1986, (Hurst, J. K. In: Everse J.; Everse K.; Grisham M. B., eds. Peroxidases in chemistry and biology 1st ed. Boca Raton: CRC Press; 1991:37-62.) The heme protein is stored in primary azurophilic granules of leukocytes and secreted into both the extracellular milieu and the phagolysosomal compartment following phagocyte activation by a variety of agonists (Klebanoff, S. J, et al. *The neutrophil: functions and clinical disorders.* Amsterdam: Elsevier Scientific Publishing Co.; 1978.) Immunohistochemical methods have demonstrated that MPO is present in human atheroscloerotic lesions. However, MPO has not yet been shown to be present at increased levels in blood samples from individuals with atherosclerosis.

A recently proposed working kinetic model for MPO is shown in FIG. 1. MPO is a complex heme protein which possesses multiple intermediate states, each of which are influenced by the availability of reduced oxygen species such as $O_2^-$ and $H_2O_2$, and nitric oxide (NO, nitrogen monoxide) (Abu-Soud, H. M., et al., *J. Biol. Chem.* 275:5425-5430; 2000). At ground state, MPO exists in the ferric (Fe(III)) form. Upon addition of $H_2O_2$, the heme group of MPO is oxidized two e⁻ equivalents forming a reactive ferryl π cation radical intermediate termed Compound I. In the presence of halides such as Cl⁻, Br⁻, and I⁻, and the psuedohalide thiocyanate (SCN⁻), Compound I is readily reduced in a single two e⁻ step, regenerating MPO-Fe(III) and the corresponding hypohalous acid (HOX). At plasma levels of halides and thiocyanate (100 mM Cl⁻, 100 mM Br⁻ 50 mM SCN⁻, 100 nM I⁻, chloride is a preferred substrate and hypochlorous acid (HOCl), a potent chlorinating oxidant, is formed (Foote, C. S., et al.; *Nature* 301:715-726; 1983, Weiss, S. J., et al. *J. Clin. Invest.* 70:598-607; 1982).

Compound I can also oxidize numerous organic substrates while the heme undergoes two sequential one e⁻ reduction steps, generating compound II and MPO-Fe(III), respectively (FIG. 1). Low molecular weight compounds primarily serve as substrates for MPO, generating diffusible oxidants and free radical species, which can then convey the oxidizing potential of the heme to distant targets. In addition to halides and SCN⁻, some of the naturally occurring substrates for MPO include nitrite ($NO_2^-$) (van der Vliet, A., et al., *J. Biol. Chem.* 272: 7617-7625; 1997), tyrosine (van der Vliet, A., et al., *J. Biol. Chem.* 272:7617-7625; 1997), ascorbate (Marquez, L. A., et al., *J. Biol. Chem.* 265:5666-5670; 1990), (Maehly, H. C. *Methods Enzymol.* 2:798-801; 1955), catecholamines (Metodiewa, D., et al., *Eur. J. Biochem.* 193:445-448; 1990), estrogens (Klebanoff, S. J. *J. Exp. Med.* 145:983-998; 1977), and serotonin (Svensson, B. E. *Chem. Biol. Interact.* 70:305-321; 1989). MPO-Fe(III) can also be reduced to an inactive ferrous form, MPO-Fe(II) (Hurst, J. K. In: Everse J.; Everse K.; Grisham M. B., eds. Peroxidases in chemistry and biology 1st ed. Boca Raton: CRC Press; 1991:37-62, (Kettle, A. J., et al., *Redox. Rep.* 3:3-15; 1997). MPO-Fe(III) and MPO-Fe(II) bind to $O_2^-$, and $O_2$, respectively, forming a ferrous dioxy intermediate, compound III (MPO-Fe(II)—$O_2$) (FIG. 1). Spectral studies demonstrate that addition of $H_2O_2$ to Compound III ultimately forms compound II. Thus, compound III may indirectly promote one e⁻ peroxidation reactions.

Recent studies identify a role for NO, a relatively long-lived free radical generated by nitric oxide synthase (NOS), in modulating MPO peroxidase activity (Abu-Soud, H. M., et al., *J. Biol. Chem.* 275:5425-5430; 2000). MPO and the inducible isoform of NOS are colocalized in the primary granule of leukocytes. During phagocyte activation, such as during ingestion of bacteria, MPO and NOS are secreted into the phagolysosome and extracellular compartments, and nitration of bacterial proteins is observed (Evans, T. J., et al., *Proc. Natl. Acad. Sci. USA* 93:9553-9558; 1996). Rapid kinetics studies demonstrate that at low levels of NO, the initial rate of MPO-catalyzed peroxidation of substrates is enhanced. The mechanism is through acceleration of the rate-limiting step in MPO catalysis, reduction of compound II to MPO-Fe(III) (FIG. 1) (Abu-Soud, H. M., et al., *J. Biol. Chem.* 275:5425-5430; 2000., Abu-Soud, H. M., et al. Nitric oxide is a physiological substrate for mammalian animal peroxidases. Submitted; 2000). At higher levels of NO, reversible inhibition of MPO occurs through formation of a spectroscopically distinguishable nitrosyl complex, MPO-Fe(III)—NO (Abu-Soud, H. M., et al., *J. Biol. Chem.* 275:5425-5430; 2000). NO also can serve as a substrate for MPO compound I, resulting in its reduction to Compound II (Abu-Soud, H. M., et al. Nitric oxide is a physiological substrate for mammalian animal peroxidases. Submitted; 2000). Furthermore, in the presence of NO, the overall turnover rate of MPO through the peroxidase cycle is enhanced nearly 1000-fold (Abu-Soud, H. M., et al. Nitric oxide is a physiological substrate for mammalian animal peroxidases. Submitted; 2000). Finally, NO also reversibly binds to MPO-Fe(II) forming the corresponding MPO-Fe(II)—NO intermediate, which is in equilibrium with MPO-Fe(II) and MPO-Fe(III)—NO (FIG. 1) (Abu-Soud, H. M., et al., *J. Biol. Chem.* 275:5425-5430; 2000., Abu-Soud, H. M., et al. Nitric oxide is a physiological substrate for mammalian animal peroxidases. Submitted; 2000).

As described above, MPO can utilize a variety of co-substrates with $H_2O_2$ to generate reactive oxidants as intermediates. Many stable end-products generated by these species have been characterized and shown to be enriched in proteins, lipids, and LDL recovered from human atherosclerotic lesions (Chisolm, G. M., et al., *Proc. Natl. Acad. Sci. USA* 91:11452-11456; 1994, Hazell, L. J., et al., *J. Clin. Invest.* 97:1535-1544; 1996, Hazen, S. L., et al., *J. Clin. Invest* 99:2075-2081; 1997, Leeuwenburgh, C., et al., *J. Biol. Chem.* 272:1433-1436; 1997, Leeuwenburgh, C., et al., *J. Biol. Chem.* 272:3520-3526; 1997). FIG. 2 summarizes some of the reactive intermediates and products formed by MPO, any of, which are known to be enriched in vascular lesions.

Methods of Determining MPO Activity

Myeloperoxidase activity may be determined by any of a variety of standard methods known in the art. One such method is a colorimetric-based assay where a chromophore that serves as a substrate for the peroxidase generates a product with a characteristic wavelength which may be followed by any of various spectroscopic methods including UV-visible or fluorescence detection. Additional details of colorimetric based assays can be found in Kettle, A. J. and Winterboum, C. C. (1994) *Methods in Enzymology.* 233: 502-512; and Klebanoff, S. J., Waltersdorph, A. N. and Rosen, H. (1984) *Methods in Enzymology.* 105: 399-403, both of which are incorporated herein by reference. An article by Gerber, Claudia, E. et al., entitled "Phagocytic Activity and Oxidative Burst of Granulocytes in Persons with Myeloperoxidase Deficiency" published in 1996 in Eur. J. Clin. Chem Clin Biochem 34:901-908, describes a method for isolation for polymorphonuclear leukocytes (i.e., neutrophils) and measurement of myeloperoxidase activity with a colorometric assay, which involves oxidation of the chromogen 4-chloro-1-naphthol.

Peroxidase activity may be determined by in situ peroxidase staining in MPO containing cells with flow cytometry-based methods. Such methods allow for high through-put screening for peroxidase activity determinations in leukocytes and subpopulations of leukocytes. An example is the cytochemical peroxidase staining used for generating white blood cell count and differentials with hematology analyzers based upon peroxidase staining methods. For example, the Advia 120 hematology system by Bayer analyzes whole blood by flow cytometry and performs peroxidase staining of white blood cells to obtain a total white blood cell count (CBC) and to differentiate amongst the various white blood cell groups.

With these methods, whole blood enters the instrument and red blood cells are lysed in a lysis chamber. The remaining white blood cells are then fixed and stained in situ for peroxidase activity. The stained cells are channeled into the flow cytometer for characterization based upon the intensity of peroxidase staining and the overall size of the cell, which is reflected in the amount of light scatter of a given cell. These two parameters are plotted on the x and y axis, respectively, by conventional flow cytometry software, and clusters of individual cell populations are readily discernible. These include, but are not limited to, neutrophils, monocytes and eosinophils, the three major leukocyte populations containing visible peroxidase staining.

During the course of these analyses, leukocytes such as monocytes, neutrophils, eosinophils and lymphocytes are identified by the intensity of peroxidase staining and their overall size. Information about the overall peroxidase activity staining within specific cell populations is thus inherent in the position of individual cell clusters (e.g., neutrophil, monocyte, eosinophil clusters) and peroxidase levels within specific cell populations may be determined. Peroxidase activity/staining in this detection method is compared to a peroxidase stain reference or calibrant. Individuals with higher levels of peroxidase activity per leukocyte are identified by having a cell population whose location on the cytogram indicates higher levels of peroxidase (i.e., average peroxidase activity per leukocyte) or by demonstrating a sub-population of cells within a cell cluster (e.g., neutrophil, monocyte, eosinophil clusters) which contain higher levels of peroxidase activity either on average or in a higher subgroup, such as the higher tertile or quartile.

Methods of Determining MPO Mass

The mass of myeloperoxidase in a given bodily sample is readily determined by an immunological method, e.g., ELISA. Commercial kits for MPO quantification by ELISA are available. MPO mass in a bodily sample can also be determined indirectly by in situ peroxidase staining of the bodily sample. Methods which analyze leukocyte peroxidase staining can be performed on whole blood, such as those with hematology analyzers which function based upon in situ peroxidase staining. Previous studies by other investigators have demonstrated that the overall intensity of staining is proportional to peroxidase mass (e.g., Claudia E. Gerber, Selim Kuci, Matthias Zipfel, Ditrich Niethammer and Gemot Bruchfelt, "Phagocytic activity and phagocytic activity and oxidative burst of granulocytes in persons with myeloperoxidase deficiency" European Journal of Clinical Chemistry and Clinic Biochemistry (1996) 34:901-908).

Flow cytometry through a hematology analyzer is a high through-put technique for quantifying the parameters used in determining MPO activity or mass levels or numbers of cells containing elevated levels of MPO activity or mass. The advantage of using such a technique is its ease of use and speed. The Advia 120 can perform 120 complete cell blood count and differentials in one hour and utilizes only a few microliters of blood at a time. All the data necessary for determination of the peroxidase activity is held within the flow cytometry cell clusters used to ultimately calculate the total white blood cell count and differential. With minor adjustments to software of this apparatus, the readout can be modified to include multiple different indices of overall peroxidase activity.

Levels of MPO Activity and MPO Mass

The level of MPO activity or MPO mass in the a bodily sample (e.g., bodily fluid) can be determined by measuring the MPO activity or MPO mass in the body fluid and normalizing this value to obtain the MPO activity or mass per ml of blood, per ml of serum, per ml of plasma, per leukocyte (e.g., neutrophil or monocyte), per weight, e.g. mg of total blood protein, per weight of leukocyte protein (e.g., per weight of neutrophil or monocyte protein). Alternatively, the level of MPO activity or MPO mass in the body fluid can be a representative value, which is based on MPO activity in the test subjects blood or blood derivatives. For example, the level of MPO activity can be the percentage or the actual number of the test subject's neutrophils or monocytes that contain elevated levels of MPO activity or MPO mass. Examples of other representative values include, but are not limited to, arbitrary units for a parameter that can be obtained from a flow cytometry based cytogram, such as the position of the neutrophil cluster on the X and Y axes, or the angle of the major axis of the neutrophil cluster relative to the X and Y axes.

Myeloperoxidase-Generated Oxidation Products

Role of MPO in the Generation of HETEs and HODEs and Oxidized Cholesterol Esters A role for MPO in the oxidation of LDL and the initiation of lipid peroxidation has recently been questioned by several investigators. Noguchi and colleagues examined the capacity of leukocytes isolated from wild-type and MPO knockout mice to promote oxidation of LDL in model systems ex vivo and observed only modest differences in the parameters of lipid oxidation monitored. (Noguchi N, et al. J. Biochem. (Tokyo) 2000;127:971-976). It has also recently been suggested that MPO-catalyzed oxidation of LDL is inhibited, rather than promoted, by the presence of $NO_2^-$, particularly when focusing upon protein oxidation products. (Carr A C, et al., J. Biol. Chem. 2001;276:1822-1828). Moreover, an antioxidant rather than a pro-oxidant function for MPO-generated tyrosine oxidation products and LDL oxidation has been proposed. (Santanam N., et al J. Clin. Invest 1995;95:2594-2600, Exner M. et al., FEBS Lett. 2001;490:28-31). It has also been suggested by some investigators that HOCl generated by MPO can promote oxidation of lipoprotein lipids and formation of hydroperoxides (Panasenko O M., Biofactors 1997;6:181-190), whereas other studies have not supported these observations. (Schmitt D, et al., Biochem. 1999;38:16904-16915, Hazen S L, et al., Circ. Res. 1999;85:950-958). Finally, recent studies have noted species differences between murine and human leukocytes with respect to MPO and generation of reactive oxidant species. (Xie Q W, et al., Biological oxidants: generation and injurious consequences. San Diego, Calif., USA, Academic Press, 1992, Rausch P G, et al., Blood 1975;46:913-919, Nauseef W M., J. Clin. Invest 2001; 107:401-403, Brennan M L, et al. J. Clin. Invest 2001;107: 419-430).

To determine the role of MPO in promoting lipid oxidation in plasma, we incubated activated neutrophils from healthy subjects and subjects with a myeloperoxidase deficiency with whole plasma (50%, v/v) and physiological levels of $Cl^-$ (100 mM final). Phagocytes were activated with PMA and the formation of specific oxidation products of linoleic and arachidonic acids, respectively, was determined by LC/ESI/MS/MS.

MPO and Lipoprotein Isolation

MPO (donor: hydrogen peroxide, oxidoreductase, EC 1.11.1.7) was isolated and characterized as described. (Heinecke J W, et al., J. Biol. Chem. 1993;268:4069-4077, Wu W, et al., Biochemistry 1999;38:3538-3548). Purity of isolated MPO was established by demonstrating a R/Z≧0.85 ($A_{430}/A_{280}$), SDS PAGE analysis with Coomassie Blue staining, and in-gel tetramethylbenzidine peroxidase staining to confirm no eosinophil peroxidase contamination. (Wu W, et al., Biochemistry 1999;38:3538-3548). Purified MPO was stored in 50% glycerol at −20° C. Enzyme concentration was determined spectrophotometrically ($\epsilon_{430}$=170,000 $M^{-1}$ $cm^{-1}$). (Odajima T, et al. Biochim. Biophys. Acta. 1970; :71-77). LDL was isolated from fresh plasma by sequential ultracentrifugation as a 1.019<D<1.063 g/ml fraction with dialysis performed in sealed jars under argon atmosphere. (Hatch F T. Adv. Lipid Res. 1968;6:1-68). Final preparations were kept in 50 mM sodium phosphate (pH 7.0), 100 µM DTPA and stored under $N_2$ until use. LDL concentrations are expressed per mg of LDL protein.

Human Neutrophil Preparations

Human neutrophils were isolated from whole blood obtained from normal and MPO-deficient subjects, as described. (Hazen S L, et al., J. Biol. Chem. 1996;271:1861-1867). Neutrophils preparations were suspended in HBSS ($Mg^{2+}$—, $Ca^{2+}$—, phenol- and bicarbonate-free, pH 7.0) and used immediately for experiments.

Lipid Peroxidation Reaction

Isolated human neutrophils ($10^6$/ml) were incubated at 37° C. with either 50% (v/v) normal human plasma or isolated human LDL (0.2 mg/ml) under air in HBSS supplemented with 100 µM DTPA. Neutrophils were activated by adding 200 nM phorbol myristate acetate (PMA) and maintained in suspension by gentle mixing every 5 min. After 2 h, reactions were stopped by immersion in ice/water bath, centrifugation at 4° C. and immediate addition of 50 µM butylated hydroxytoluene (BHT) and 300 nM catalase to the supernatant. Lipid peroxidation products in the supernatant were then rapidly assayed as described below.

Reactions with isolated MPO were typically performed at 37° C. in sodium phosphate buffer (20 mM, pH 7.0) supplemented with 100 µM DTPA using 30 nM MPO, 1 mM glucose (G), 20 ng/ml glucose oxidase (GO). Under this condition, a constant flux of $H_2O_2$ (0.18 µM/min) was generated by the glucose/glucose oxidase (G/GO) system. Unless otherwise stated, reactions were terminated by immersion in ice/water bath and addition of both 50 µM BHT and 300 nM catalase to the reaction mixture.

Lipid Extraction and Sample Preparation

Lipids were extracted and prepared for mass spectrometry analysis under argon or nitrogen atmosphere at all steps. First, hydroperoxides in the reaction mixture were reduced to their corresponding hydroxides by adding $SnCl_2$ (1 mM final). A known amount of deuterated internal standard, 12(S)-hydroxy-5,8,10,14-eicosatetraenoic-5,6,8,9,11,12,14,15-d8 acid (12-HETE-d8; Cayman Chemical Company, Ann Arbor, Mich.) was added to the sample, and then plasma lipids were extracted by adding a mixture of 1 M acetic acid/2-isopropanol/hexane (2/20/30, v/v/v) at a ratio of 5 ml organic solvent mix: 1 ml plasma. Following vortexing of the mixture and centrifugation, lipids were extracted into the hexane layer. Plasma was re-extracted by addition of an equal volume of hexane, followed by vortexing and centrifugation. Cholesteryl ester hydroperoxides (CE-H(P)ODEs) were analyzed as their stable $SnCl_2$-reduced hydroxide forms by drying of the combined hexane extracts under $N_2$, reconstituting samples with 200 µl 2-isopropanol/acetonitrile/water (44/54/2, v/v/v) and storage at −80° C. under argon until analysis. For the assay of free fatty acids and their oxidation products, total lipids (phospholipids, cholesterol esters, triglycerides) were dried under $N_2$, re-suspended in 1.5 ml 2-isopropanol and then fatty acids were released by base hydrolysis with 1.5 ml 1M NaOH at 60° C. for 30 min under argon. The hydrolyzed samples were acidified to pH 3.0 with 2M HCl and fatty acids were extracted twice with 5 ml hexane. The combined hexane layers were dried under $N_2$, resuspended in 100 µl methanol and stored under argon at −80° C. until analysis by LC/ESI/MS/MS), as described below.

HPLC Fractionation of Plasma Filtrate

In order to study the role played by low molecular weight compounds in plasma as substrates for MPO in promotion of lipid peroxidation, whole plasma from normal healthy donors was filtered through a 10 kDa MWt cut off filter (Centriprep YM-10, Millipore-Corporation Bedford, Mass. USA) by centrifugation. The filtrate of plasma was used either directly or following fractionation by HPLC. Reverse phase HPLC fractionation of was performed using a Beckman C-18 column (4.6×250 mm, 5 µm ODS; Beckman Instruments, Inc. Fullerton, Calif.). The separation of low molecular weight compounds in plasma filtrate (0.5 ml) was carried out at the flow rate 1.0 ml/min with the following gradient: 100% mobile phase A (water containing 0.1% acetic acid) over 10 min, then linear gradient to 100% mobile phase B (methanol containing 0.1% acetic acid) over 10 min, followed by 100% mobile phase B over 5 min. Effluent was collected as 1 ml fractions, dried under $N_2$, and then resuspended in buffer (0.1 ml) for analysis. Fractionation of plasma filtrate (0.5 ml) by strong anion exchange HPLC (SAX-HPLC) was performed on a SPHERIS HPLC column (4.6×250 mm, 5 µm SAX; Phase Separations Inc. Norwalk Conn.). The separation of low molecular weight compounds in plasma filtrate was carried out at the flow rate 0.9 ml/min under isocratic conditions using 45 mM ammonium acetate buffer (pH 4.0) as mobile phase. Effluent was collected as 1.0 ml fractions, dried under $N_2$, and then resuspended in buffer (0.1 ml) for analysis.

A. Mass Spectrometry

LC/ESI/MS/MS was employed to quantify free radical-dependent oxidation products of arachidonic acid (9-hydroxy-5,7,11,14-eicosatetraenoic acid and 9-hydroperoxy-5,7,11,14-eicosatetraenoic acid (9-H(P)ETE)), and linoleic acid (9-hydroxy-10,12-octadecadienoic acid and 9-hydroperoxy-10,12-octadecadienoic acid (9-H(P)ODE)). Immediately prior to analysis, one volume of $H_2O$ was added to five volumes methanol-suspended sample, which was then passed through a 0.22 µm filter (Millipore Corporation, Bedford, Mass.). Sample (20 µl) was injected onto a Prodigy C-18 column (1×250 mm, 5 µm ODS, 100A; Phenomenex, Rancho Palos Verdes, Calif.) at a flow rate of 50 µl/min. The separation was performed under isocratic conditions using 95% methanol in water as the mobile phase. In each analysis, the entirety of the HPLC column effluent was introduced onto a Quattro II triple quandrupole MS (Micromass, Inc.). Analyses were performed using electrospray ionization in negative-ion mode with multiple reaction monitoring (MRM) of parent and characteristic daughter ions specific for the isomers monitored. The transitions monitored were mass-to-charge ratio (m/z) 295 171 for 9-HODE; m/z 319 151 for 9-HETE; m/z 327 184 for 12-HETE-d8. $N_2$ was used as the curtain gas in the electrospray interface. The internal standard 12-HETE-dS was used to calculate extraction efficiencies (which were >80% for all analyses). External calibration curves constructed with authentic standards were used to quantify 9-HETE and 9-HODE.

B. RP-HPLC Quantification of CE-H(P)ODEs

Sample (100 µl) reconstituted in methanol (without base hydrolysis) were injected onto a Beckman C-18 column (4.6× 250 mm, 5 µm ODS; Beckman Instruments, Inc., Fullerton, Calif.). Lipids were separated using an isocratic solvent system comprised of 2-isopropanol/acetonitrile/water (44/54/2, v/v/v) at a flow rate of 1.5 ml/min. CE-H(P)ODEs were quantified as their stable hydroxide forms by UV detection at 234 nm using CE-9-HODE (Cayman Chemical Company, Ann Arbor, Mich.) for generation of an external calibration curve.

Results

Normal neutrophils generated significant levels of 9-H(P)ODE and 9-(H)PETE in plasma following cell activation by PMA (FIGS. 4(A-B)). In stark contrast, MPO-deficient neutrophils failed to generate significant levels of lipid peroxidation products following stimulation with PMA, despite their enhanced capacity to produce $O_2$. Addition of catalytic amounts of MPO restored the capacity of MPO-deficient neutrophils to initiate peroxidation of endogenous plasma lipids (FIGS. 4(A-B)).

Figure 5B:
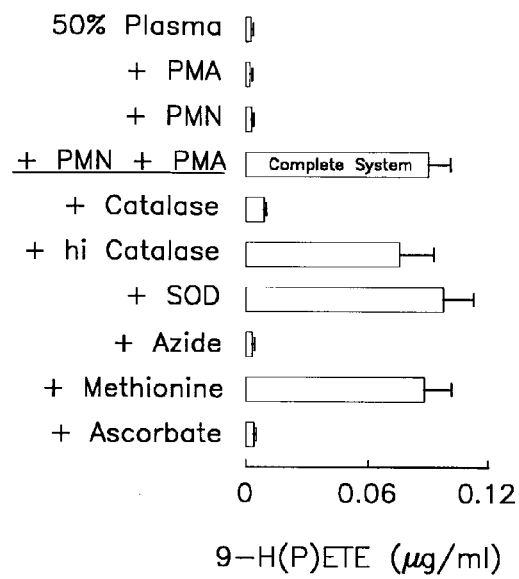

Addition of catalase, but not heat inactivated catalase, to cell mixtures resulted in the near complete ablation of lipid peroxidation in plasma, strongly suggesting a critical role for $H_2O_2$ in the cell-dependent reaction (FIGS. 5(A-B)). Incubation of reaction mixtures with superoxide dismutase (SOD) failed to attenuate oxidation of plasma lipids (FIGS. 5(A-B)). In contrast, addition of heme poisons (e.g. azide, cyanide) and the water-soluble antioxidant ascorbate resulted in complete inhibition of neutrophil-depended peroxidation of plasma lipids. Finally, addition of HOCl scavengers such as dithiothreitol and the thioether methionine, failed to attenuate neutrophil-dependent peroxidation of endogenous plasma lipids, assessed by quantification of 9-H(P)ODE and 9-H(P)ETE (FIGS. 5(A-B)).

Figure 6A:
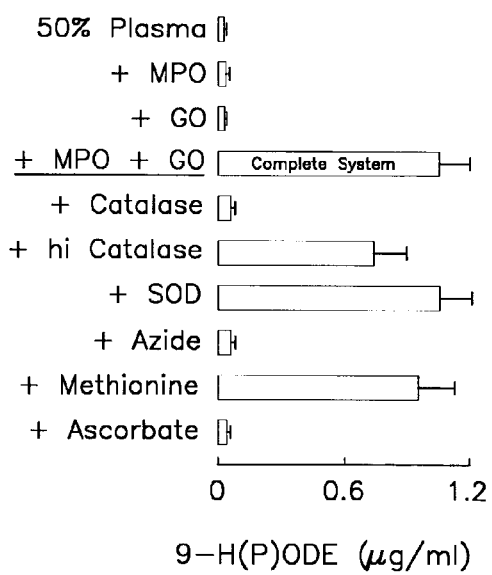
FIGS. 6(A-B) are graphs showing the characterization of MPO-dependent initiation of lipid peroxidation of endogenous plasma lipids. Fresh human plasma (50%, v/v) was incubated with isolated human MPO (30 nM) at 37° C. in HBSS supplemented with DTPA (100 μM, pH 7.0) and a $H_2O_2$-generating system comprised of glucose/glucose oxidase (G/GO) for 12 h (Complete System). Under this condition, a continuous flux of $H_2O_2$ is formed at 10 μM/hr. The content of 9-H(P)ODE and 9-H(P)ETE formed within endogenous plasma lipids were then determined by LC/ESI/MS/MS. Additions or deletions to the Complete System were as indicated. The final concentrations of additions to the Complete System were 1 mM $NaN_3$, 300 nM catalase (Cat), 300 nM heat-inactivated catalase (hiCat), 200 nM SOD, 100 μM methionine (Met), and 100 μM ascorbate. Data represent the mean±SD of three independent experiments.
Figure 6B:
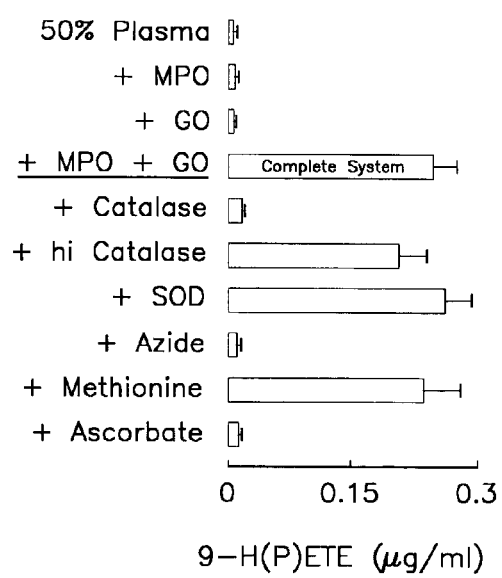

Results thus far presented strongly suggest that neutrophils employ the MPO-$H_2O_2$ system to generate reactive species distinct from chlorinating intermediates as the primary oxidants for initiation of lipid peroxidation in plasma. To confirm a physiological role for MPO, we next added purified human MPO and a $H_2O_2$-generating system (glucose/glucose oxidase, G/GO) to plasma and monitored formation of specific oxidation products by LC/ESI/MS/MS analysis. Formation of 9-H(P)ODE and 9-H(P)ETE occurred readily and had an absolute requirement for the presence of both MPO and the $H_2O_2$-generating system (FIGS. 6(A-B)). Lipid oxidation was again inhibited by catalase, azide or ascorbate, but was not affected by addition of SOD or methionine (FIGS. 6(A-B)). Collectively, these results strongly support a pivotal role for the MPO-$H_2O_2$ system of leukocytes as a primary mechanism for initiating lipid peroxidation in complex biological tissues and fluids such as plasma.

MPO Oxidation of LDL and the Presence of the Resultant Oxidation Products in Atherosclerotic Lesions General Procedures Human myeloperoxidase (donor: hydrogen peroxide, oxidoreductase, EC 1.11.1.7) and LDL were isolated and quantified as described (Podrez, E. A, et al., 1999, *J. Clin. Invest.* 103:1547). All buffers were treated with Chelex-100 resin (Bio-Rad, Hercules, Calif.) and supplemented with diethylenetriaminepentaacetic acid (DTPA) to remove trace levels of transition metal ions that might catalyze LDL oxidation during incubations. LDL was labeled with Na[$L^{125}I$] to a specific activity between 100 and 250 dpm/ng protein, as described (Hoppe, G., et al., 1994, *J. Clin. Invest.* 94, 1506-12). Extraction of cellular lipids and thin-layer chromatography separation of radio-labeled cholesterol esters and free cholesterol were performed as described (Podrez, E. A, et al., 1999, *J. Clin. Invest.* 103:1547). Incorporation of [$^{14}C$]oleate into cholesteryl esters by cells following incubation with the indicated lipoproteins (50 µg/ml), were determined as described (Podrez, E. A, et al., 1999, *J. Clin. Invest.* 103:1547). Rabbit thoracic aortae were isolated from WHHL Rabbits, rinsed in argon-sparged PBS supplemented with 100 µM butylated hydroxytoluene (BHT) and 100 µM DTPA, submerged in the same buffer, covered in argon and flash frozen in liquid nitrogen and then stored at −80° C. until analysis. Aortae relatively free of lipid lesions were obtained from WHHL rabbits age 10-12 weeks, while aortae full of lesions were recovered from WHHL rabbits greater than 6 months old.

Lipoprotein Modification

LDL modified by MPO-generated nitrating intermediates ($NO_2$-LDL) was formed by incubating LDL (0.2 mg protein/ml) at 37° C. in 50 mM sodium phosphate, pH 7.0, 100 µM DTPA, 30 nM MPO, 100 µg/ml glucose, 20 ng/ml glucose oxidase and 0.5 mM $NaNO_2$ for 8 h unless otherwise specified. Under these conditions, a constant flux of $H_2O_2$ (10 µM/hr) is generated by the glucose/glucose oxidase system, as determined by the oxidation of Fe(II) and formation of Fe(III)-thiocyanate complex (van der Vliet, A., et al., 1997, *J. Biol. Chem.*, 272:7617). Oxidation reactions were terminated by addition of 40 µM BHT and 300 nM catalase to the reaction mixture. LDL acetylation was performed as described earlier (Podrez, E. A, et al., 1999, *J. Clin. Invest.* 103:1547).

Phospholipid Separation and Mass Spectrometric Analysis

Lipids were maintained under inert atmosphere (argon or nitrogen) at all times. Lipids from either oxidized PAPC or PLPC vesicles, or from $NO_2$-LDL, were extracted three times sequentially by the method of Bligh and Dyer [Bligh, 1959] immediately after adding an equal volume of saturated NaCl solution (to enhance lipid extraction). The combined chloroform extracts were evaporated under nitrogen, and lipids were then resuspended in methanol (at approximately 200 µg/0.1 ml), filtered through an Acrodisc CR PTFE filter and applied on a reverse-phase column (Luna C18, 250×10 mm, 5 µm, Phenomenex, Torrence, Calif., USA). Lipids were resolved at a flow rate of 3 mL/min using a ternary (acetonitrile/methanol/$H_2O$) gradient generated by a Waters 600 E Multisolvent delivery system HPLC (Waters, Milford, Mass., USA), and monitored using an evaporative light scattering detector (Sedex 55, Sedere, Alfortville, France).

Further fractionation and isolation of bioactive lipids was performed on combined lipid extracts from three separations that were dried under $N_2$, resuspended in chloroform (300 µl) supplemented with BHT and maintained under argon atmosphere. An aliquot of the fraction (⅔rds) was removed, evaporated under nitrogen and resuspended in HPLC buffer (methanol/water; 85/15; v/v) immediately prior to injection on reverse phase HPLC column.

Mass spectrometric analyses were performed on a Quatro II triple-quadrupole mass spectrometer (Micromass, Inc., Altrincham, U.K.) equipped with an electrospray ionization (ESI) probe and interfaced with an HP 1100 HPLC (Hewlett-Packard, Wilmington, Del.). Lipids (both free and following derivatization) were resolved on a Luna C18 250×4.6 mm, 5 μm column (Phenomenex, Torrance, Calif.) at a flow rate of 0.8 ml/min. A discontinuous gradient (Gradient II) was used by mixing solvent A (methanol (MeOH):$H_2O$, 85:15, v:v) with solvent B (MeOH), as follows: isocratic elution with solvent A from 0-7 min; increasing to 88% solvent B from 7-10 min; increasing to 91% solvent B from 10-34 min; and then increasing to 94% solvent B from 34-52 min). The column effluent was split such that 45 μl/min was introduced to the mass spectrometer and 755 μl/min was collected and analyzed for biological activity. In some cases, biological activity was also determined using the same gradient following injection of authentic standards. Mass spectrometric analyses were performed on-line using electrospray ionization tandem mass spectrometry (ESI/MS/MS) in the positive ion mode with multiple reaction monitoring (MRM) mode (cone potential 60 eV/collision energy 20-25 eV). The MRM transitions used to detect the oxidized phospholipids present in each fraction were the mass to charge ratio (m/z) for the molecular cation $[MH]^+$ and the daughter ion m/z 184, the phosphocholine group (i.e. $[MH]^+ \rightarrow$ m/z 184). Oxime derivatives of phospholipids were monitored at m/z $[MH+29]^+ \rightarrow$ m/z 184.

Quantification of the various oxidized PC species was performed using LC/ESI/MS/MS in positive ion mode using MRM. Formic acid (0.1%) was included in the mobile phases. Distinct oxidized phospholipid species were identified by using m/z for protonated parent-daughter transitions specific for each individual phospholipid and their retention times, as illustrated in FIGS. 2 and 3. OV-PC and ND-PC were quantified similarly but by also monitoring at the m/z for the transition between the hemiacetal formed with methanol for each analyte and the loss of polar head group (m/z 184).

Figure 7A:
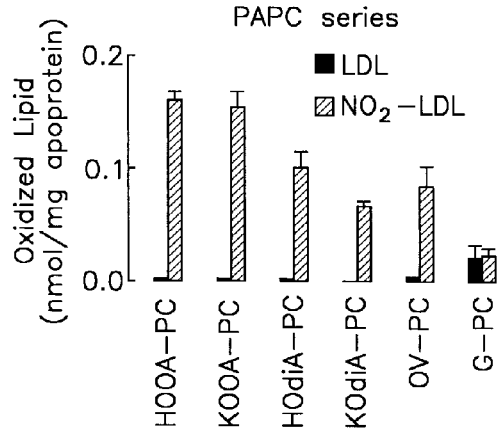
FIGS. 7(A-B) are graphs showing the oxidized phosphatidyl choline species generated by MPO oxidation of LDL are enriched in atherosclerotic lesions. The contents of the indicated oxidized PC species were determined in native LDL and LDL oxidized by the MPO-$H_2O_2$—$NO_2$ system ($NO_2$-LDL) using LC/ESI/MS/MS. Data represent the mean±S.D. of triplicate determinations of a representative experiment performed two times. The content of PAPC in LDL and $NO_2$-LDL preparations were 0.122±0.07 and 0.008±0.001 μmol/mg apoprotein, respectively. The content of PLPC in LDL and $NO_2$-LDL preparations were 0.88±0.05 and 0.35±0.05 μmol/mg apoprotein, respectively. The thoracic aorta from Watanabe Heritable Hyperlipidemic Rabbits was isolated, rinsed in Argon sparged PBS supplemented with 100 μM BHT and 100 μM DTPA, submerged in the same buffer, covered in argon, flash-frozen in liquid nitrogen and then stored at −80° C. until analysis. Aortae relatively free of lipid lesions were obtained from WHHL rabbits age 10-12 weeks, while aortae with confluent lesions were recovered from WHHL rabbits >6 months old. Individual frozen aortae were pulverized with stainless steel mortar and pestle under liquid nitrogen, the powder transferred to glass screw capped test tubes equipped with PTFE-lined caps, and then lipids were extracted by the method of Bligh and Dyer under Argon in the presence of BHT. Three aortae were analyzed in each group. Quantification of lipids was then performed by LC/ESI/MS/MS. Data are expressed as mean±S.D.

Lipids were initially extracted three times by the method of Bligh and Dyer (Bligh, E. G., et al., 1959, *Canadian Journal of Biochemical Physiology*, 37, 911-917) from lipoproteins or tissues in the presence of BHT. The combined extracts were rapidly dried under nitrogen, resuspended in methanol:$H_2O$ (98:2, v:v), and then neutral lipids in the lipid extracts were removed by passage through a 18C minicolumn (Supelclean LC-18 SPE tubes, 3 ml; Supelco Inc., Bellefonte, Pa.). A known amount of dimyristyl phosphatidyl choline (DMPC) was added to the polar lipid fraction as an internal standard, and the lipids were dried under nitrogen and stored under an argon atmosphere at −80° C. until analysis within 24 h. Calibration curves were constructed with a fixed amount of DMPC and varying mol % of each synthetic oxidized PC species and used to correct for the differences in ionization response factors observed amongst the different lipids. In additional preliminary studies the quantification methods employed were independently validated for each analyte by demonstrating identical results to those obtained by the method of standard additions Results Quantification of various specific oxidized PC species by LC/ESI/MS/MS analysis in native and oxidized forms of LDL revealed substantial increases in the content of oxidized phosphatidyl choline species (FIG. 7A, data for native LDL, $NO_2$-LDL shown). Regardless of what time point of oxidation was examined, HODA-PC and HOOA-PC were major products of LDL oxidation by MPO. The combined mol % (relative to remaining unoxidized phospholipids) and ND-PC) detected in $NO_2$-LDL (FIG. 7A) correspond to 1.2 mol %. Of these, the combined content of the 8 oxidized PC species quantified in $NO_2$LDL preparation (FIG. 7A) correspond to 0.73 mol %.

Figure 7B:
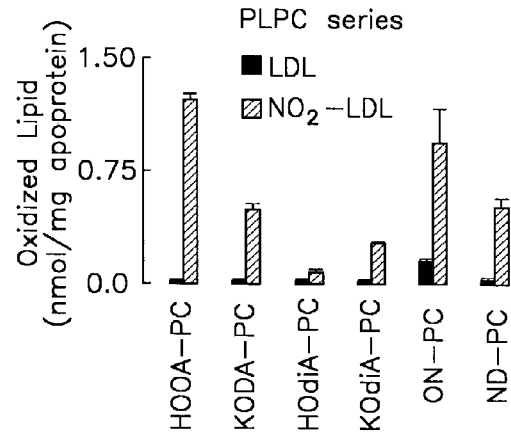

To determine if oxidated PC species are formed in vivo, thoracic aortae with and without extensive atherosclerotic lesions were isolated from Watanabe heritable hyperlipidemic (WHHL) rabbits and the levels of multiple distinct specific oxidized phospholipids were determined using LC/ESI/MS/MS analyses. Significant increases in the content of each of the oxidized PCs derived from oxPAPC(HOOA-PC, KOOA-PC, HOdiA-PC, KOdiA-PC) and oxPLPC (HODA-PC, KODA-PC, HDdiA-PC and KDdiA-PC) were noted in the diseased vessels (FIG. 7B). Interestingly, while the levels of oxidized PC species derived from PLPC were lower than that observed for the more highly oxidized ON-PC and ND-PC, levels of oxidized PC species derived from PAPC were comparable to that observed for OV-PC and G-PC (FIG. 7A).

Figure 8:
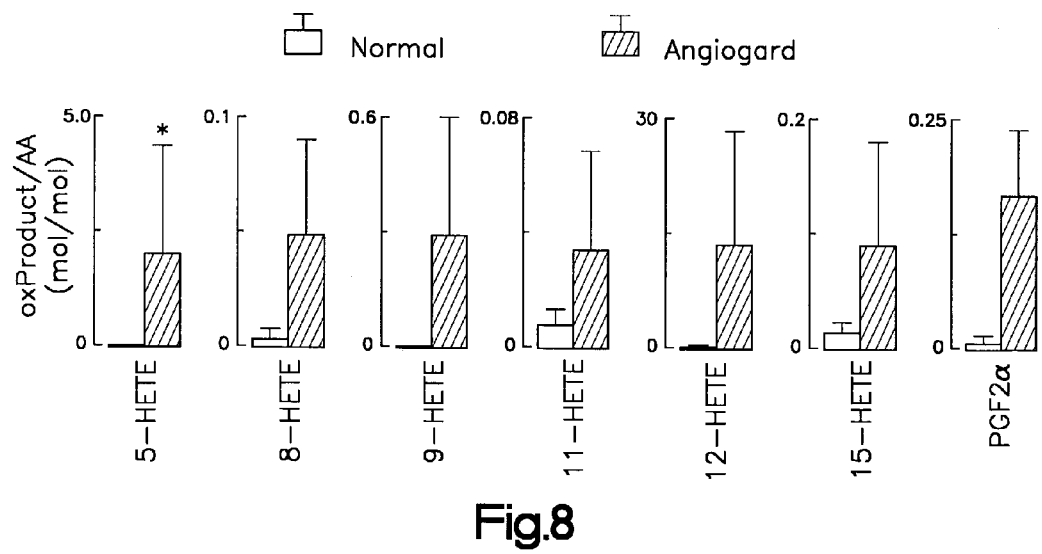
FIG. 8 is a graph showing the content of select MPO-generated oxidized lipids in atherosclerotic plaque material of human patients and normal aortic intima of heart transplant donors.

Presence of HETEs, HODEs, F2 Isoprostanes and Oxidated PC Species in Atherscloerotic Lesions of Human Subjects The Angiogard is an emboli-protection device recently invented for use during percutaneous vascular interventions. It is deployed distal to the target lesion prior to balloon inflation for angioplasty. It serves as a temporary umbrella, catching extruded lipid-rich plaque material through an inert sieve-like mesh. The pores of the mesh are large and microscopy confirms that they do not obstruct flow of blood cells or platelets, but rather capture large lipid globules. The material captured in the Angiogard at the time of intervention was analyzed to determine the lipid species in the plaque material. FIG. 8 shows the levels of multiple distinct lipid oxidation products quantified by LC/ESI/MS/MS methods in plaque material recovered from the Angiogard. For comparison, we also assessed the levels of the same oxidized lipids in normal aortic intima recovered at the time of organ harvest from heart transplant donors. Dramatic increases in $F_2$-Isoprostanes and each of the HETEs monitored were observed. Analysis of plaque material captured in the Angiogard also confirmed detection of multiple distinct oxPC species (data not shown).

Methods of Determining Levels of Select Myeloperoxidase-Generated Oxidation Products A. Dityrosine and Nitrotyrosine Dityrosine and nitrotyrosine levels in the bodily sample can be determined using monoclonal antibodies that are reactive with such tyrosine species. For example, anti-nitrotyrosine antibodies may be made and labeled using standard procedures and then employed in immunoassays to detect the presence of free or peptide-bound nitrotyrosine in the sample. Suitable immunoassays include, by way of example, radioimmunoassays, both solid and liquid phase, fluorescence-linked assays or enzyme-linked immunosorbent assays. Preferably, the immunoassays are also used to quantify the amount of the tyrosine species that is present in the sample.

Monoclonal antibodies raised against the dityrosine and nitrotyrosine species are produced according to established procedures. Generally, the dityrosine or nitrotyrosine residue, which is known as a hapten, is first conjugated to a carrier protein and used to immunize a host animal. Preferably, the dityrosine and nitrotyrosine residue is inserted into synthetic peptides with different surrounding sequence and then coupled to carrier proteins. By rotating the sequence surrounding the dityrosine and nitrotyrosine species within the peptide coupled to the carrier, antibodies to only the dityrosine and nitrotyrosine species, regardless of the surrounding sequence context, are generated. Similar strategies have been successfully employed with a variety of other low molecular weight amino acid analogues.

Suitable host animals, include, but are not limited to, rabbits, mice, rats, goats, and guinea pigs. Various adjuvants may be used to increase the immunological response in the host animal. The adjuvant used depends, at least in part, on the host species. To increase the likelihood that monoclonal antibodies specific to the dityrosine and nitrotyrosine are produced, the peptide containing the respective dityrosine and nitrotyrosine species may be conjugated to a carrier protein which is present in the animal immunized. For example, guinea pig albumin is commonly used as a carrier for immunizations in guinea pigs. Such animals produce heterogeneous populations of antibody molecules, which are referred to as polyclonal antibodies and which may be derived from the sera of the immunized animals.

Monoclonal antibodies, which are homogenous populations of an antibody that binds to a particular antigen, are obtained from continuous cells lines. Conventional techniques for producing monoclonal antibodies are the hybridoma technique of Kohler and Millstein (Nature 356:495-497 (1975)) and the human B-cell hybridoma technique of Kosbor et al. (Immunology Today 4:72 (1983)). Such antibodies may be of any immunoglobulin class including IgG, IgM, IgE, Iga, IgD and any class thereof. Procedures for preparing antibodies against modified amino acids, such as for example, 3-nitrotyrosine are described in Ye, Y. Z., M. Strong, Z. Q. Huang, and J. S. Beckman. 1996. Antibodies that recognize nitrotyrosine. *Methods Enzymol.* 269:201-209.

In general, techniques for direct measurement of protein bound dityrosine and nitrotyrosine species from bodily fluids involves removal of protein and lipids to provide a fluid extract containing free amino acid residues. The tissues and bodily fluids are stored, preferably in buffered, chelated and antioxidant-protected solutions, preferably at −80° C. as described above. The frozen tissue, and bodily fluids are then thawed, homogenized and extracted, preferably with a single phase mixture of methanol:diethylether:water as described above to remove lipids and salts. Heavy isotope labeled internal standards are added to the pellet, which, preferably, is dried under vacuum, hydrolyzed, and then the amino acid hydrolysate resuspended, preferably in a water:methanol mixture, passed over a mini solid-phase C 18 extraction column, derivatized and analyzed by stable isotope dilution gas chromatography-mass spectrometry as above. Values of free dityrosine and nitrotyrosine species in the bodily sample can be normalized to protein content, or an amino acid such as tyrosine as described above.

In a highly preferred procedure, protein is delipidated and desalted using two sequential extractions with a single phase mixture of $H_2O$/methanol/$H_2O$-saturated diethyl ether (1:3:8 v/v/v). Oxidized tyrosine standards (2 pmol each) and universal labeled tyrosine (2 nmol) are added to protein pellets. Proteins are hydrolyzed by incubating the desalted protein pellet with degassed 6N HCl supplemented with 1% phenol for 24 h under argon atmosphere. Amino acid hydrolysates are resuspended in chelex treated water and applied to mini solid-phase C18 extraction columns (Supelclean LC-C18SPE minicolumn; 3 ml; Supelco, Inc., Bellefone, Pa.) pre-equilibrated with 0.1% trifluoroacetic acid. Following sequential washes with 2 ml of 0.1% trifluoroacetic acid, oxidized tyrosines and tyrosine are eluted with 2 ml 30% methanol in 0.1% trifluoroacetic acid, dried under vacuum and then analyzed by mass spectrometry.

Tandem mass spectrometry is performed using electrospray ionization and detection with an ion trap mass spectrometer (LCQ Deca, ThermoFinigann, San Jose, Calif.) interfaced with a Thermo SP4000 high performance liquid chromatograph (HPLC). Samples are suspended in equilibration solvent ($H_2O$ with 0.1% formic acid) and injected onto a Ultrasphere C18 column (Phenominex, 5 µm, 2.0 mm×150 mm). L-Tyrosine and its oxidation products are eluted at a flow rate of 200 µl/min using a linear gradient generated against 0.1% formic acid in methanol, pH 2.5 as the second mobile phase. Analytes are monitored in positive ion mode with full scan product ion MS/MS at unit resolution. Response is optimized with a spray voltage setting of 5 KV and a spray current of 80 µA. The heated capillary voltage is set at 10 V and the temperature to 350° C. Nitrogen is used both as sheath and auxiliary gas, at a flow rate of 70 and 30 arbitrary units, respectively. The analyte abundance is evaluated by measuring the chromatographic peak areas of selected product ions extracted from the full scan total ion chromatograms, according to the corresponding ion trap product ion spectra. The ions monitored for each analyte are: 3-nitro[$^{12}C_6$]tyrosine (mass-to-charge-ratio (m/z) 227, 181 and 210), 3-nitro[$^{13}C_6$]tyrosine (m/z 233, 187 and 216), 3-nitro[$^{13}C_9^{15}N_1$]tyrosine (m/z 237, 190 and 219), [$^{12}C_6$]tyrosine (m/z 182, 136 and 165), [$^{13}C_9^{15}N_1$]tyrosine (m/z 192, 145 and 174). Tyrosine and nitrotyrosine are base-line resolved under the HPLC conditions employed, permitting programming of the LCQ Deca for analysis over 0-7 min for detection of tyrosine isotopomers, and from 7 min on for detection of 3-nitrotyrosine isotopomers.

Free nitrotyrosine and dityrosine are similarly measured in samples, but tissue or bodily fluid is first passed through a low molecular weight cut off filter and the low molecular weight components analyzed by LC/ECS/MS/MS. Values of free and protein-bound dityrosine and nitrotyrosine species in the bodily sample can be normalized to protein content, or an amino acid such as the precursor tyrosine, as described below.

Although, the method described above relates to using monoclonal antibodies for the detection of dityrosine and nitrotyrosine, the method can also be used can also be used for the detection of other myeloperoxidase generated products. For example, monoclonal antibodies can also be used for the detection of chlorotyrosine and homocitrulline.

B. Lipid Oxidation Products

Lipid oxidation products can be measured by HPLC with UV detection or HPLC with on line mass spectrometry. Other analytical methods including GC/MS and immunocytochemical methods may also be used. F2 Isoprostanes are measurable by various mass spectrometry techniques as known in the art.

Methods of extracting and quantifying the MPO-generated lipid oxidation products hydroxy-eicosatetraenoic acids (HETEs), hydroxy-octadecadienoic acids (HODEs), F2Isoprostanes; the 5-oxovaleric acid esters of 2-lysoPC (OV-PC); 5-cholesten-5α,6α-epoxy-3β-ol (cholesterol α-epoxide); 5-cholesten-5β,6β-epoxy-3β-ol (cholesterol β-epoxide); 5-cholesten-3β,7β-diol (7-OH-cholesterol); 5-cholesten-3β,25-diol (25-OH cholesterol 5-cholesten-3β-ol-7β-hydroperoxide (7-OOH cholesterol); and cholestan-3α,5α,6β-triol (triol).are described in Schmitt, et al., (1999) Biochemistry, Vol. 38, 16904-16915, which is specifically incorporated herein by reference. For determination of 9-H (P)ODE, 9-H(P)ETE and $F_2$-isoprostanes, hydroperoxides in reaction mixtures are reduced to their corresponding hydroxides during extraction utilizing a modified Dole procedure in which the reducing agent, triphenylphosphine, is present (Savenkova, M. L., et al. (1994) *J. Biol. Chem.* 269, 20394-20400). These conditions also inhibit artifactual formation of isoprostanes and oxidized lipids. Lipids are dried under $N_2$, resuspended in isopropanol (2 ml) and then fatty acids released by base hydrolysis with 1 N sodium hydroxide (2 ml) at room temperature under $N_2$ for 90 min. The samples are acidified (pH 3.0) with 2N HCl, known amounts of internal standards are added and free fatty acids are extracted twice with hexane (5 ml). The content of 9-H(P)ODEs, 9-H(P)ETEs and $F_2$-isoprostanes are then determined by LC/MS/MS analysis as outlined below.

1-palmitoyl-2 oxovaleryl-sn-glycero-3-phosphatidyl choline (POV-PC) is extracted by the same modified Dole procedure used for 9-H(P)ODE, 9-H(P)ETE and $F_2$ isoprostane analyses as above, but omitting addition of the reductant, triphenylphosphine. Lipids are dried under $N_2$, resuspended in methanol and stored under argon at $-70°$ C. until subsequent LC/MS analysis as outline below. Sterol oxidation products are extracted by adding 4 M NaCl (150 µl) and acetonitrile (500 µl). Samples are vortexed, centrifuged, and the upper organic phase removed. Extracts are dried under $N_2$, resuspended in methanol, and stored under argon at $-70°$ C. until analysis by HPLC with on-line mass spectrometric analysis.

Mass spectrometric analyses are performed on a Quatro II triple quadruple mass spectrometer interfaced with an HP 1100 HPLC. $F_2$-isoprostanes are quantified by stable isotope dilution mass spectrometry using on-line reverse phase HPLC tandem mass spectrometry (LC/MS/MS) with 8-epi-$[^2H_4]PGF_2$, as standard as described by Mallat (Mallat, Z., et al. (1999) *J. Clin. Invest.* 103, 421-427). For 9-HODE and 9-HETE analyses, lipid extracts generated following base hydrolysis of reduced lipids (above) are dried under $N_2$ and reconstituted in methanol. An aliquot of the mixture is then injected on an Ultrasphere ODS C18 column equilibrated and run under isocratic conditions employing methanol:$H_2O$, (85:15, v/v) as solvent. Column eluent is split (930 µl/min to UV detector and 70 µl/min to mass detector) and analyzed by the mass spectrometer. LC/MS/MS analysis of 9-HODE, 9-HETE and $F_2$-isoprostanes in column effluents is performed using electrospray ionization mass spectrometry (ESI-MS) in the negative-ion mode with multiple reaction monitoring (MRM) and monitoring the transitions m/z 295→171 for 9-HODE; m/z 319→151 for 9-HETE; m/z 353→309 for $F_2$-isoprostanes; and m/z 357→313 for $[^2H_4]PGF_{2\alpha}$.

Quantification of POV-PC is performed on lipid extracts utilizing HPLC with on-line ESI-MS analysis in the positive ion mode and selected ion monitoring at m/z 782 and m/z 594, respectively. An aliquot of lipid extract reconstituted in methanol (above) is mixed 0.1% formic acid in methanol (mobile phase B) and loaded onto a Columbus C18 column (1×250 mm, 5 µm, P. J. Cobert, St. Louis, Mo.) pre-equilibrated in 70% mobile phase B, 30% mobile phase A (0.1% formic acid in water) at a flow rate of 30 µl/min. Following a 3 min wash period at 70% mobile phase B, the column is developed with a linear gradient to 100% mobile phase B, followed by isocratic elution with 100% mobile phase B. External calibration curves constructed with authentic POV-PC are used for quantification. 7-OH cholesterol, 7-keto cholesterol, and 7-OOH cholesterol are resolved on an Ultrasphere ODS C18 column. The elution gradient consisted of 91:9, acetonitrile: water+0.1% formate (v:v), and the column washed between runs with acetonitrile+0.1% formate. Column effluent is split (900 µl/min to UV detector and 100 µl/min to mass detector) and ionized by atmospheric pressure chemical ionization (APCI) in the positive-ion mode with selected ion monitoring. Identification of 7-OH cholesterol is performed by demonstrating co-migration of ions with m/z 385.3 $(M-H_2O)^+$ and m/z 367.3 $(M-2H_2O)^+$ with the same retention time as authentic standard. The integrated area of the ion current for the peak monitored at m/z 367.3 is used for quantification. Identification of 7-OOH cholesterol is performed by demonstrating co-migration of ions with m/z 401.3 $(M-H_2O)^+$, m/z 383.3 $(M-2H_2O)^+$ and m/z 367.3 $(M-H_2O_2)^+$ with the same retention time as authentic standard. The integrated area of the ion current for the peak monitored at m/z 401.3 is used for quantification. Identification of 7-keto cholesterol is performed by demonstrating co-migration of ions with m/z 401.3 $(M+H)^+$ and m/z 383.3 $(M-H_2O)^+$ with the same retention time as authentic standard. The integrated area of the ion current for the peak monitored at m/z 401.3 is used for quantification. External calibration curves constructed with authentic 7-OH cholesterol, 7-OOH cholesterol and 7-keto cholesterol are used for quantification following preliminary APCI LC/MS experiments demonstrating identical results to those obtained by the method of standard additions. The retention times for 25-OH cholesterol, 5,6α- and β-epoxides, and triol are determined by LC/MS analysis of authentic standards.

Predetermined Value

The level of MPO mass, MPO activity, or select MPO-generated oxidation product in the bodily sample obtained from the test subject can be compared to a predetermined value. The predetermined value can be based upon the levels of MPO activity, MPO mass, or select MPO-generated oxidation product in comparable samples obtained from the general population or from a select population of human subjects. For example, the select population may be comprised of apparently healthy subjects. "Apparently healthy", as used herein, means individuals who have not previously had any signs or symptoms indicating the presence of disease, such as atherosclerosis, angina pectoris, history of an acute adverse cardiovascular event (e.g., a myocardial infarction or stroke), and evidence of atherosclerosis by diagnostic imaging methods including, but not limited to coronary angiography. In other words, such individuals, if examined by a medical professional, would be characterized as healthy and free of symptoms of disease.

The predetermined value can be related to the value used to characterize the level of MPO activity or MPO mass in the bodily sample obtained from the test subject. Thus, if the level of MPO activity is an absolute value such as the units of MPO activity per leukocyte or per ml of blood, the predetermined value is also based upon the units of MPO activity per leukocyte or per ml of blood in individuals in the general population or a select population of human subjects. Similarly, if the level of MPO activity or MPO mass is a representative value such as an arbitrary unit obtained from a cytogram, the predetermined value is also based on the representative value.

The predetermined value can take a variety of forms. The predetermined value can be a single cut-off value, such as a median or mean. The predetermined value can be established based upon comparative groups such as where the level of systemic marker (e.g., level of MPO) in one defined group is double the level of systemic marker in another defined group. The predetermined value can be a range, for example, where the general population is divided equally (or unequally) into groups, or into quadrants, the lowest quadrant being individuals with the lowest levels of systemic marker, the highest quadrant being individuals with the highest levels of systemic marker.

The predetermined value can be derived by determining the level of MPO activity or mass in the general population. Alternatively, the predetermined value can be derived by determining the level of MPO activity or mass in a select population, such as an apparently healthy nonsmoker population. For example, an apparently healthy, nonsmoker population may have a different normal range of MPO activity or MPO mass than will a smoking population or a population whose members have had a prior cardiovascular disorder. Accordingly, the predetermined values selected may take into account the category in which an individual falls. Appropriate ranges and categories can be selected with no more than routine experimentation by those of ordinary skill in the art.

Predetermined values of MPO activity or MPO mass, such as for example, mean levels, median levels, or "cut-off" levels, are established by assaying a large sample of individuals in the general population or the select population and using a statistical model such as the predictive value method for selecting a positivity criterion or receiver operator characteristic curve that defines optimum specificity (highest true negative rate) and sensitivity (highest true positive rate) as described in Knapp, R. G., and Miller, M. C. (1992). Clinical Epidemiology and Biostatistics. William and Wilkins, Harual Publishing Co. Malvern, Pa., which is specifically incorporated herein by reference. A "cutoff" value can be determined for each systemic marker that is assayed. The standardized method that was used in Example 1 below employs the guaiacol oxidation assay as described in Klebanoff, S. J., Waltersdorph, A. N. and Rosen, H. 1984. "Antimicrobial activity of mycloperoxidase". Methods in Enzymology. 105: 399-403).

Comparison of MPO Activity and Mass Levels and Levels of Select MPO-Generated Oxidation Products in the Bodily Sample from the Test Subject to the Predetermined Value The levels of each systemic marker, i.e., MPO activity, MPO mass and select MPO-generated oxidation product, in the individual's bodily sample may be compared to a single predetermined value or to a range of predetermined values. If the level of systemic marker in the test subject's bodily sample is lower than the predetermined value or range of predetermined values following administration of the therapeutic agent, the therapeutic agent has provided a anti-inflammatory and/or anti-oxidant effect to the test subject. The extent of the difference between the test subject's systemic marker level and the predetermined value is also useful for characterizing the extent of the anti-inflammatory and/or antioxidant actions of the therapeutic agent and thereby, can be used to determine and monitor an effective treatment strategy with the therapeutic agent.

The present diagnostic methods are useful for determining if and when therapeutic agents which are targeted at treating disorders where inflammation and/or oxidative damage is linked to pathogenesis of the disorder should and should not be prescribed for a patient. For example, individuals with values of MPO activity (U/mg PMN protein; or U/ml blood) above a certain cutoff value, or that are in the higher tertile or quartile of a "normal range," could be identified as those in need of more aggressive intervention with therapeutic agents.

The present diagnostic methods are further useful for determining an effective amount of therapeutic agent for treating disorders where inflammation and/or oxidative damage is linked to pathogenesis of the disorder. In the method, the therapeutic agent can be administered to the subject. The level of at least one systemic marker indicative of inflammation and/or oxidation in the subject during or following administration of the therapeutic agent can be monitored to determine an effective amount of the therapeutic agent. The marker can include MPO activity, MPO mass, select MPO-generated oxidation products, and combinations thereof.

An effective amount is a dosage of the therapeutic agent sufficient to provide a medically desirable result. The effective amount will vary with the particular condition being treated, the age and physical condition of the subject being treated, the severity of the condition, the duration of the treatment, the nature of the concurrent therapy (if any), the specific route of administration and the like factors within the knowledge and expertise of the health practitioner. For example, an effective amount can depend upon the degree to which an individual has abnormally elevated levels of markers of systemic information. It should be understood that the agents of the invention can be used to decrease inflammation and/or oxidative damage. Thus, an effective amount can be that amount which decreases inflammation and/or oxidative damage. It will be recognized when the agent is used in acute circumstances, it can be used to prevent one or more medically undesirable results that typically flow from such adverse events. It is expected that doses will range depending on the method of administration. In the event that a response in a subject is insufficient at the initial doses applied, higher doses (or effectively higher doses by a different, more localized delivery route) may be employed to the extent that patient tolerance permits. Multiple doses per day are contemplated to achieve appropriate systemic levels of compounds.

EXAMPLES

The following examples are for purposes of illustration only and are not intended to limit the scope of the claims which are appended hereto.

Example 1

Levels of MPO Activity and MPO Mass in Blood Samples of Patients with and without Coronary Artery Disease Methods Study Population Based on logistic regression power calculations (assuming equal size groups), 326 patients were needed to provide 80% power (=0.05) to detect a statistically significant odds ratio of at least 2.0 for high MPO (upper quartile). Subjects (n=333) were identified from two practices within the Cardiology Department of the Cleveland Clinic Foundation. First, a series of 85 consecutive patients were enrolled from the Preventive Cardiology Clinic. Simultaneously, 125 consecutive patients were enrolled from the catheterization laboratory. Based upon CAD prevalence in this series, a need for 116 additional control subjects was determined. All patients who did not have significant CAD upon catheterization over the preceding 6 months were identified from the catheterization database, and then 140 were randomly selected (based upon area code/telephone number) and invited to participate for MPO measurement. CAD was defined by a history of documented myocardial infarction, prior coronary revascularization intervention (CABG or percutaneous coronary intervention), or as the presence of ≧50% stenosis in one or more coronary arteries identified during cardiac catheterization.

Exclusion criteria for the CAD group were an acute coronary event within 3 months preceding enrolment, end stage renal disease and bone marrow transplantation. The control group consisted of subjects who had undergone diagnostic coronary angiography that revealed no evidence of significant CAD. Exclusion criteria for control subjects were one or more coronary vessels with stenosis ≧50%, vascular heart disease, left ventricle dysfunction, end-stage renal disease, bone marrow transplantation, or evidence of infection or active inflammatory diseases as revealed by history and exam. All patients were older than 45 years of age and afibrile. Clinical history was assessed for diabetes mellitus, smoking history past and present, hypertension and whether any first-degree relatives had CAD (men by the age of 50 years and females by the age of 60). Study protocol and consent forms were approved by the Cleveland Clinic Foundation Institutional Review Board and informed, written consent was obtained from all subjects. Samples were coded to ensure anonymity and all analyses were performed in a blinded fashion.

Measurements

Blood was drawn following an overnight fast into EDTA-containing tubes and used to quantify WBC, low density lipoprotein cholesterol (LDLc), high density lipoprotein cholesterol (HDLc), total cholesterol (TC) and fasting triglycerides (TG). Neutrophils were isolated by buoyant density centrifugation (Hazen, S. L., et al., *J. Biol. Chem.* 271:1861-1867). Cell preparations were at least 98% homogeneous by visual inspection. Leukocyte preparations were supplemented to 0.2% cetyltrimethylammonium bromide for cellular lysis, incubated at room temperature for 10 min, snap frozen in liquid nitrogen and stored at −80° C. until analysis.

Functional MPO was quantified by peroxidase activity assay of neutrophil lysates. Briefly, detergent-lysed cells ($10^4$/ml; triplicate samples) were added to 20 mM phosphate buffer (pH 7.0) containing 14.4 mM guaiacol, 0.34 mM $H_2O_2$, and 200 μM DTPA and the formation of guaiacol oxidation product monitored at $A_{470}$ at 25° C. (Klebanoff, S. J., et al., *Methods Enzymol.* 105:399-403, Capeillere-Blandin, C., *Biochem. J* 36(Pt2):395-404). A millimolar absorbance coefficient of 26.6 $mM^{-1}$ $cm^{-1}$ for the diguaiacol oxidation product was used to calculate peroxidase activity where one unit of MPO activity is defined as the amount that consumes 1 μmol of $H_2O_2$ per minute at 25° C. MPO activity reported is normalized either per mg of neutrophil protein (Leukocyte-MPO) or per ml of blood (Blood-MPO). Blood-MPO (Units MPO per ml of blood) was estimated by multiplying the units of MPO activity per neutrophil times the absolute neutrophil count (per microliter blood) times 1000. Protein concentration was determined as described (Markwell, M. A., et al., *Anal Biochem.* 87:206-210).

Levels of Leukocyte-MPO in an individual were found to be extremely reproducible, demonstrating less than ±7% variations in subjects over time (n=6 males evaluated once per 1-3 months for >2 year period). The coefficient of variance for determination of Leukocyte-MPO, as determined by analysis of samples multiple times consecutively, was 4.2%. Leukocyte-MPO determination for 10 samples run on 3 separate days yielded a coefficient of variance of 4.6%. The coefficient of variance for determination of Blood-MPO as determined by analysis of samples multiple times consecutively, was 4.2%. Blood-MPO determination for 10 samples run on 3 separate days yielded a coefficient of variance of 4.8%. MPO mass per neutrophil was determined using an enzyme linked immunosorbent assay (ELISA). Capture plates were made by incubating 96-well plates overnight with polyclonal antibody (Dako, Glostrup, Denmark.) raised against the heavy chain of human MPO (10 μg/ml in 10 mM PBS, pH 7.2). Plates were washed and sandwich ELISA performed on leukocyte lysates using alkaline phosphatase-labeled antibody to human MPO. MPO mass was calculated based on standard curves generated with known amounts of human MPO purified from leukocytes as described (Hazen, S. L., et al., *J. Biol. Chem.* 271:1861-1867). Purity of isolated MPO was established by demonstrating a RZ of 0.87 ($A_{430}/A_{280}$), SDS PAGE analysis, and in-gel tetramethylbenzidine peroxidase staining (Podrez, E. A., et al., *J. Clin. Invest* 103:1547-1560). Enzyme concentration was determined spectrophotometrically utilizing an extinction coefficient of 89,000 $M^{-1}$ $cm^{-1}$/heme.

Statistical Analysis

Presentation characteristics are depicted as either mean±standard deviation or median (interquartile range) for continuous measures and number and percent for categorical measures. Differences between CAD and control subjects were evaluated with Wilcoxon rank sum or chi-square tests. MPO levels were divided into quartiles for analyses because neither Leukocyte-MPO nor Blood-MPO activity follows a Gaussian distribution. Unadjusted trends for increasing CAD rates with increasing MPO activity were evaluated with the Cochran-Armitage trend test. A modified Framingham Global Risk score was determined utilizing a documented history of hypertension rather than the recorded blood pressure at time of catheterization (Taylor, A. J., et al., *Circulation* 101: 1243-1248).

Logistic regression models (SAS System, SAS Institute, Cary N.C.) were developed to calculate odds ratios (OR) estimating the relative risk associated with the combined $2^{nd}$ and $3^{rd}$ quartiles of MPO activity and the highest quartile of MPO activity compared to the lowest quartile. Adjustments were made for individual traditional CAD risk factors (age, gender, diabetes, hypertension, smoking (ever or current), family history, TC, LDLc, HDLc, TG, WBC). Hosmer-Lemeshow goodness of fit tests were employed to evaluate appropriate model fit. Associations among continuous variables were assessed with use of Spearman's rank-correlation coefficient. Associations among categorical variables were assessed using Wilcoxon rank sum tests.

Results

Patient Demographics

The clinical and biochemical characteristics of subjects that participated in this study are shown in Table 1. Subjects with CAD were older, more likely to be male, and more likely to have a history of diabetes, hypertension and smoking. CAD subjects also exhibited increased fasting triglyceride levels, increased use of lipid lowering medications (predominantly statins), aspirin and other cardiovascular medications. Consistent with other studies, Framingham Global Risk Score, absolute neutrophil count and WBC were significantly increased in subjects with CAD (p<0.001 for each; Table 1).

TABLE 1

| Characteristics | c) Control (n = 175) | i) CAD (n = 158) |
|---|---|---|
| Age, y | 55 ± 10 | 64 ± 13*** |
| Gender (female), % | 42 | 20*** |
| Clinical and Biochemical Characteristics of Subjects | | |
| Diabetes, % | 5 | 23*** |
| Hypertension, % | 31 | 58*** |
| Family history of CAD, % | 53 | 54 |

TABLE 1-continued

| Characteristics | c) Control (n = 175) | i) CAD (n = 158) |
|---|---|---|
| History of smoking, % | 49 | 78*** |
| Current smoking, % | 10 | 9 |
| Any lipid lowering medications, % | 27 | 70*** |
| Statin, % | 25 | 65*** |
| ASA, % | 71 | 84** |
| ACE Inhibitors, % | 18 | 44*** |
| Beta Blockers, % | 27 | 59*** |
| Calcium Channel Blockers, % | 15 | 24* |
| Total cholesterol, mg/dL | 203 (166–234) | 203 (174–234) |
| LDL cholesterol, mg/dL | 132 (89–144) | 122 (90–146) |
| HDL cholesterol, mg/dL | 49 (40–56) | 43 (36–49) |
| Fasting triglycerides mg/dL | 121 (91–198) | 159 (117–240)*** |
| WBC ($\times 10^3/\mu l$) | 7.4 ± 3.0 | 8.4 ± 3.2*** |
| ANC ($\times 10^3/\mu l$) | 3.8 ± 1.9 | 5.2 ± 2.6*** |
| Framingham Global Risk | 5.5 ± 3.8 | 8.0 ± 3.0*** |

Stratification of Leukocyte-MPO, Blood-MPO and White Blood Cell Count v. Prevalence of Coronary Artery Disease To test the hypothesis that individuals with higher levels of MPO have a higher prevalence of CAD, we isolated neutrophils and measured their MPO content. MPO activity per mg of neutrophil protein (Leukocyte-MPO) differed significantly by CAD status with a median of 13.4 U/mg for control subjects v. 18.1 U/mg for CAD patients (p<0.001 for trend, and for difference; FIG. 1). Stratification of Leukocyte-MPO levels by quartiles for the entire cohort revealed a positive correlation with CAD status (p<0.001 for trend) with individuals in the highest quartile having the highest risk (OR(CI), 8.8 (4.4-17.5); Table 2). In addition to quantifying leukocyte MPO content by its catalytic activity (i.e. a functional assay), we independently quantified MPO mass per neutrophil in a random subset of subjects (n=111) using an enzyme linked immunosorbent assay. Results observed from this assay significantly correlated (r=0.95) with the activity measurements (data not shown). Since rates for CAD in the second and third quartiles of Leukocyte-MPO appeared comparable (Table 2), they were combined for all further analyses and are referred to as the mid range levels in univariate and multivariate models. As has been seen in other studies, Framingham Global Risk Score and WBC were likewise positively correlated with rates of CAD (Table 2).

TABLE 2

Odds Ratio of Coronary Artery Disease Prevalence According to Myeloperoxidase Levels, White Blood Cell Count and Framingham Global Risk Score

| | Quartile | | | | |
|---|---|---|---|---|---|
| | 1 | 2 | 3 | 4 | P Value |
| Leukocyte-MPO | | | | | |
| U/mg PMN protein | ≤11.8 | 11.9–15.3 | 15.4–19.8 | ≥19.9 | |
| CAD Rate | 24/91 (26%) | 35/76 (46%) | 36/83 (43%) | 63/83 (76%) | <0.001* |
| Unadjusted OR (CI) | 1.0 | 2.4 (1.2–4.6) | 2.1 (1.1–4.0) | 8.8 (4.4–17.5) | <0.05 |
| Model 1[a] OR (CI) | | 8.5 (3.7–19.7) | | 20.3 (7.9–52.1) | <0.001 |
| Model 2[b] OR (CI) | | 4.2 (2.1–8.1) | | 11.9 (5.5–25.5) | <0.001 |
| Blood-MPO‡ | | | | | |
| U/mg PMN × ANC | ≤2.9 | 3.0–4.1 | 4.2–5.7 | ≥5.8 | |
| CAD Rate | 16/91 (18%) | 35/83 (42%) | 41/79 (52%) | 66/80 (83%) | <0.001* |
| Unadjusted OR (CI) | 1.0 | 3.4 (1.7–6.8) | 5.1 (2.5–10.2) | 22.1 (10.0–48.7) | <0.001 |
| Model 1[a] OR | | 3.6 (1.8–7.5) | | 15.1 (6.2–36.7) | <0.001 |
| Model 2[b] OR | | 5.3 (2.7–10.5) | | 20.4 (8.9–47.2) | <0.001 |
| WB count | | | | | |
| ×10⁹/L | ≤5.78 | 5.79–7.32 | 7.33–9.02 | ≥9.03 | |
| CAD Rate | 24/85 (28%) | 46/82 (56%) | 38/83 (46%) | 50/83 (60%) | <0.001* |
| Unadjusted OR (CI) | 1.0 | 3.2 (1.7–6.2) | 2.1 (1.1–4.1) | 3.9 (2.0–7.3) | <0.05 |
| Adjusted[c] OR (CI) | | 3.0 (1.6–5.7) | | 4.3 (2.1–8.9) | <0.001 |
| Framingham | | | | | |
| Global Risk Score | ≤4 | 5–7 | 8–9 | ≥10 | |
| CAD Rate | 25/86 (29%) | 41/114 (36%) | 41/63 (65%) | 51/70 (73) | <0.001* |
| Unadjusted[d] OR (CI) | 1.0 | 1.4 (0.8–2.5) | 4.5 (2.3–9.1) | 6.5 (3.2–13.2) | |
| Adjusted[ce] OR (CI) | | 1.8 (1.0–3.3) | | 7.8 (3.5–17.5) | |

*P for trend across quartiles.
[a]Model 1 consisted of covariates significant after single-factor adjustments (age, sex, diabetes, hypertension, smoking history, HDl-C, WBC count) and MPO quartiles and tested for independence of each relative to others in predicting CAD status.
[b]Model 2 consisted of Framingham Global risk assessment, WBC count and MPO quartiles.
[c]Adjusted ORs for WBC cound and Framingham were calculated with simultaneous adjustment for levels of leukocyte-MPO, WBC count, and Framingham scores
[d]Quartile 2: P = 0.31; quartiles 3 and 4: P < 0.001
[e]Midrange v. low: P = 0.06; high v. low: P < 0.001

Figure 9A:
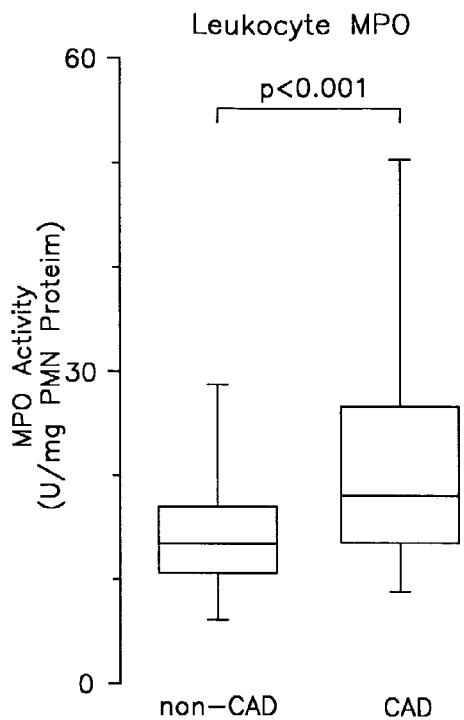
FIGS. 9(A-B) are graphs showing the content of MPO in isolated leukocytes (Leukocyte-MPO) and per ml of blood (Blood-MPO) were determined in 333 subjects (158 with known coronary artery disease and 175 without angiographically significant CAD) as described under "Methods." Box-whisker plots of MPO levels v. CAD status are shown. Boxes encompass the $25^{th}$ to $75^{th}$ percentiles. Lines within boxes represent median values. Bars represent the $2.5^{th}$ and $97.5^{th}$ percentiles. ANC, absolute neutrophil count; CAD, coronary artery disease; PMN, polymorphonuclear leukocyte.
Figure 9B:
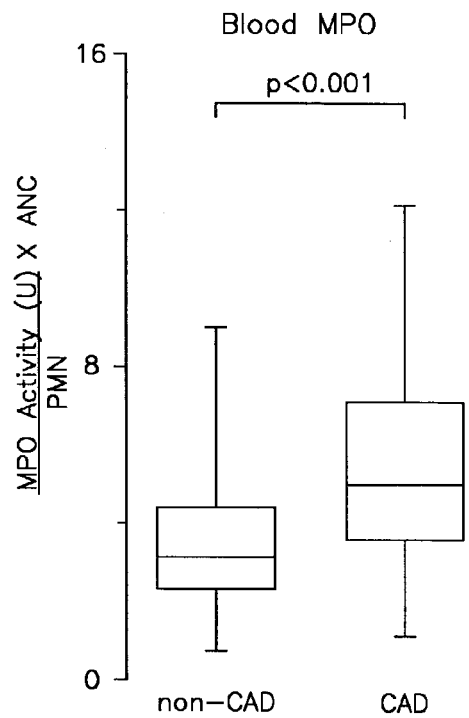

The total content of MPO in blood is dependent on both MPO levels per leukocyte as well as the total number of leukocytes. Since neutrophils possess >95% of the MPO content in blood, we estimated the level of MPO per ml of blood (Blood-MPO) by multiplying the content of MPO per neutrophil times the absolute neutrophil count. Rates of CAD were positively correlated with Blood-MPO quartiles (p<0.001 for trend; FIG. 9, Table 2).

Leukocyte-MPO is not Significantly Correlated with Traditional Coronary Artery Risk Factors Possible correlations between traditional CAD risk factors and Leukocyte-MPO were next assessed. Leukocyte-MPO levels were independent of age, gender, diabetes, hypertension, smoking (ever or current), WBC, triglycerides LDLc and Framingham Global Risk. Weak negative correlations between Leukocyte-MPO and both total cholesterol (r=−0.15, p=0.005) and HDLc (r=−0.14, p–0.01) were observed. A positive association was seen between Leukocyte-MPO and absolute neutrophil count (r=0.20, p<0.001) and family history of CAD (median leukocyte-MPO with family history=15.9 v. 14.1 without, p=0.05). Similar correlations were noted for Blood-MPO.

Leukocyte-MPO and Blood-MPO are Strongly Correlated with Coronary Artery Disease Status Following Adjustments for Single and Multiple Risk Factors To evaluate whether Leukocyte-MPO and Blood-MPO independently associate with CAD status, odds ratios for Leukocyte-MPO and Blood-MPO quartiles were adjusted for individual traditional CAD risk factors. Odds ratios for both the middle ($2^{nd}$ plus $3^{rd}$) and highest ($4^{th}$), relative to the lowest ($1^{st}$), quartiles of both Leukocyte-MPO and Blood-MPO remained highly correlated with CAD status following adjustments for individual traditional CAD risk factors, WBC and Framingham Global Risk Score (data not shown), with odds ratios ranged from 8.4 (CI=4.2-16.9, p<0.001) after adjustment for HDLc to 13.5 (CI=6.3-29.1, p<0.001) after adjustment for smoking. Diabetes, hypertension, smoking, and to a lesser degree age, HDLc, Framingham Global Risk and WBC, also remained significant predictors for CAD status following single factor adjustments. Similar results were observed for Blood-MPO following single factor adjustments for individual traditional CAD risk factors (data not shown).

Figure 10:
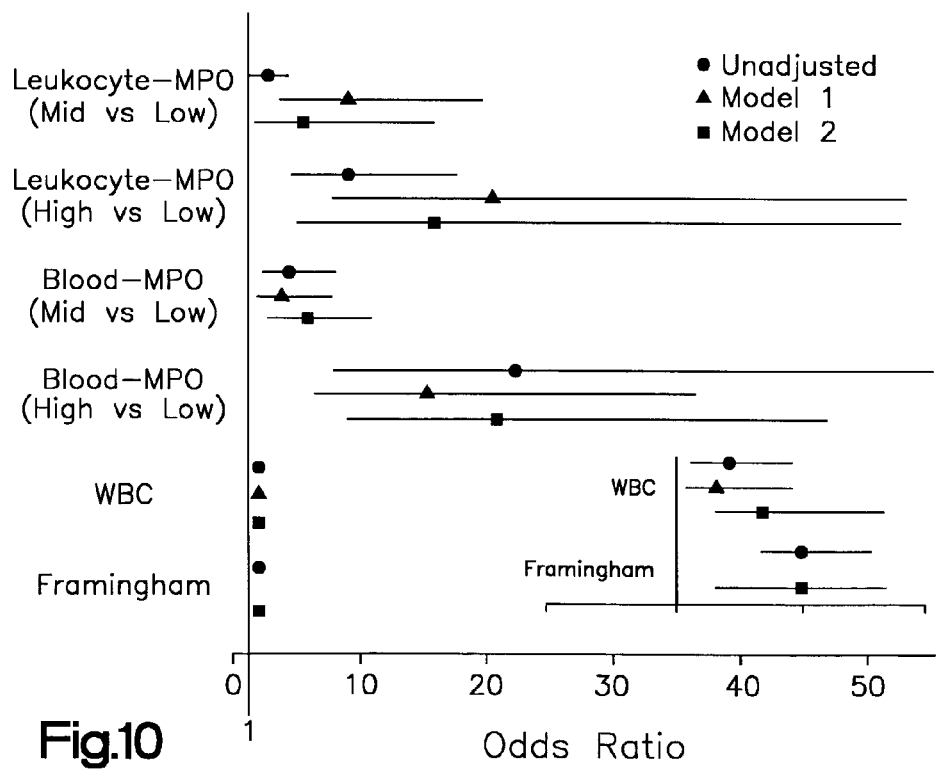
FIG. 10, Model 1, shows the odds ratios adjusted for risk factors significant following univariate adjustment: age, gender, hypertension, smoking history, HDLc, WBC quartile and MPO quartile. Model 2 shows the odds ratios adjusted for Framingham Global Risk assessment, WBC and MPO quartile. Closed circles, unadjusted odd ratios. Closed triangles, Model 1. Closed squares, Model 2.

Multivariable regression analyses were then performed using several models (Table 2, FIG. 10). Model 1 examined Leukocyte- and Blood-MPO following simultaneous adjustment for each of the single risk factors that were significantly correlated to CAD in the preceding step (i.e., univariate regression). Leukocyte-MPO remained the strongest predictor of CAD status with an adjusted OR of 8.5 (CI=3.7-19.7, mid v. low quartile) and 20.3 (CI=7.9-52.1, high v. low quartile). The adjusted odds ratio for WBC, a marker that predicts increased risk for CAD (2;3;23-25), was 1.1 (CI=1.02-1.21). A second regression model adjusting for Framingham Global Risk Score and WBC yielded ORs for Leukocyte-MPO that were consistent with the large OR observed in Model 1 (mid v. low OR=4.2; high v. low OR=11.9). The adjusted OR for Framingham Global Risk Score and WBC were also significant. Blood-MPO likewise remained a strong predictor of CAD status following multivariable adjustments compared to traditional CAD risk factors, Framingham Global Risk Score and WBC (Table 2).

Example 2

Flow Cytometric Analysis of Blood Samples from Subjects with and without CAD

Figure 11A:
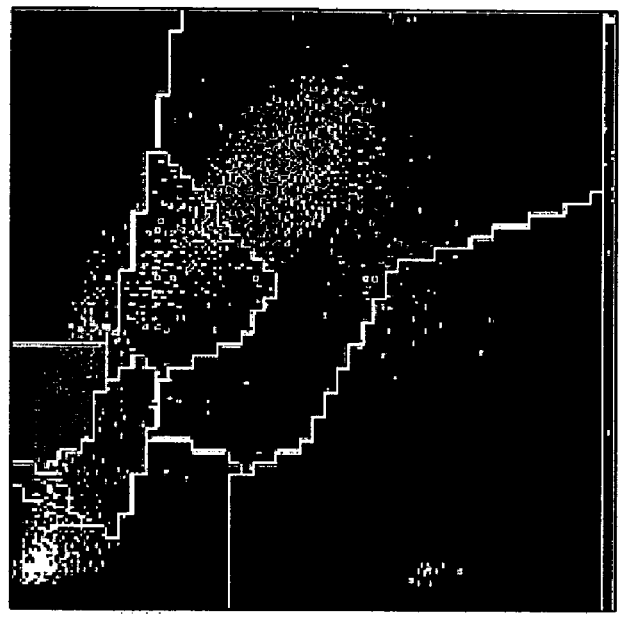
FIGS. 11 (A-B) depict a cytogram of WBC from an individual whose MPO level per neutrophil is below the average in a population (A), and an individual whose MPO level per neutrophil is above average in a population (B).
Figure 11B:
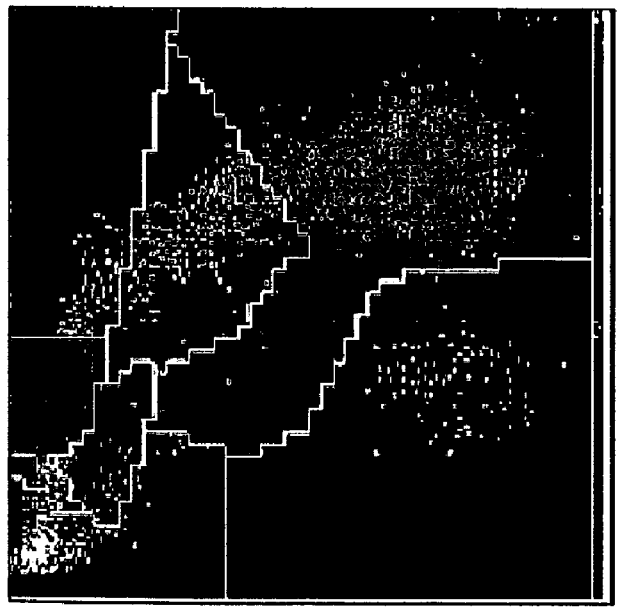

Blood samples from patients whose leukocytes have above normal or below normal levels of MPO were analyzed by flow cytometry. Whole blood from each patient was injected into a hematology analyzer that identifies leukocytes based upon in situ cytochemical peroxidase staining (the Advia 120 from Bayer). In the instrument, whole blood is first lysed and the intact WBCs heated/fixed with formaldehyde. Peroxidase substrates (hydrogen peroxide and a chromophore) are then incubated with the leukocytes, and the resultant stained cells examined by flow cytometry (20 sec overall time between injection of sample and cytogram obtained). The results are shown in FIGS. 11(A-B). The clusters of cells shown in different colors refer to: 1) Purple—neutrophils; 2) Green—monocytes; 3) Dark Blue—Lymphocytes; 4) Yellow—eosinophils; 5) Turquoise—large unstained cells; 6) White—RBC Ghosts/noise. Based upon these data, the total white blood cell count (WBC) and a differential (% distribution of neutrophils, monocytes, eosinophils and lymphocytes) are reported.

The location of a given cell cluster's position on the cytogram is related to its intensity of light absorption (Y axis—a property that is related to peroxidase activity, and hence, intensity of staining) and light scatter (X axis—a property that is related to both size and granularity/refractive index, properties linked to peroxidase activity and staining).

The left panel (i.e., panel A) illustrates the cytogram from an individual whose MPO level per neutrophil (aka leukocyte-MPO) is below the average in a population (e.g. bottom 25%). The right panel (i.e., panel B) illustrates the location of the cytogram from an individual whose MPO level per neutrophil (aka leukocyte-MPO) is above average in a population (e.g. $_{50-75}$th %). Note that the location of the neutrophil cluster on the X and Y axes differ, and in general, higher MPO is shifted to the right. Also, the tilt of the major axis of the ellipse that comprises the neutrophil cluster differs. These changes carry information related to the content of MPO within that cell type.

Through use of modeling and standards with known peroxidase content, we can develop standard curves to use this information to identify the relative level of peroxidase per leukocyte. The same kind of analysis is possible for monocytes, the other major cell type in blood with MPO. Peroxidase staining in eosinophils is due to eosinophil peroxidase, a related enzyme to MPO, but a different gene product.

Example 3

Dityrosine Levels in Blood from Human Subjects with and without CAD

The levels of protein-bound dityrosine were measured in blood samples from 112 individuals with CAD and from 128 apparently healthy control subjects. The levels were measured by HPLC with on-line fluorescence detection and were quantified using an external calibration curve generated with synthetic dityrosine. Results were normalized to the content of the precursor amino acid, tyrosine, which was simultaneously quantified by HPLC with on-line diode array detection. The results demonstrated that subjects with CAD had higher levels (50% increased, P<0.001 for comparison of CAD v. healthy subjects) of dityrosine in their serum than that observed in serum from healthy age and sex-matched subjects.

Example 4

Nitrotyrosine Levels in Blood from Human Subjects with and without CAD

The levels of protein-bound 3-nitrotyrosine were measured in blood samples from the same subjects as Example 3 where 112 individuals with CAD and 128 apparently healthy control subjects were examined. Nitrotyrosine levels were measured by HPLC with on-line electrospray ionization tandem mass spectrometry (LC/ESI/MS/MS) using stable isotope dilution techniques. Results were normalized to the content of the precursor amino acid, tyrosine, which was simultaneously quantified by stable isotope dilution LC/ESI/MS/MS. The results demonstrated that subjects with CAD had higher levels (2.8-fold increased, P<0.001 for comparison of CAD v. healthy subjects) of nitrotyrosine in their serum than healthy age and sex-matched subjects.

Example 5

Blood Levels of HETEs, HODEs, and F2Isoprostanes in Human Subjects with and without CAD The levels of HETEs, HODEs and F2Isoprostanes were measured in blood samples from the same subjects as Example 3 where 112 individuals with CAD and 128 apparently healthy control subjects were examined. Lipids were measured by HPLC with on-line electrospray ionization tandem mass spectrometry (LC/ESI/MS/MS). Results were normalized to the content of the precursor lipid (arachidonic acid for HETEs and F2Isoprostanes, and linoleic acid for HODEs), which were simultaneously quantified by LC/ESI/MS/MS. The results demonstrated that subjects with CAD had higher levels of each of the oxidation products in their plasma than healthy age and sex-matched subjects. F2Isoprostane levels were 80% greater in plasma obtained from CAD v. non-CAD subjects, P<0.001; levels of HETEs and HODEs were 60% greater in CAD v. non-CAD subjects, P<0.001).

Example 6

Blood Levels of MPO-Generated Lipid Oxidation Products in Human Subjects with and without CAD The levels of phospholipid oxidation products shown to be generated by MPO (G-PC and ND-PC, the glutaric and nonanedioic monoesters of 2-lysoPC; HDdiA-PC and HOdiA-PC, the 9-hydroxy-10-dodecenedioic acid and 5-hydroxy-8-oxo-6-octenedioic acid esters of 2-lysoPC; HODA-PC and HOOA-PC, the 9-hydroxy-12-oxo-10-dodecenoic acid and 5-hydroxy-8-oxo-6-octenoic acid esters of 2-lysoPC; KODA-PC and KOOA-PC, the 9-keto-12-oxo-10-dodecenoic acid and 5-keto-8-oxo-6-octenoic acid esters of 2-lysoPC; KDdiA-PC and KOdiA-PC, the 9-keto-10-dodecendioic acid and 5-keto-6-octendioic acid esters of 2-lysoPC; OV-PC and ON-PC, the 5-oxovaleric acid and 9-oxononanoic acid esters of 2-lysoPC; were measured in blood samples from 25 subjects with CAD and 12 apparently healthy control subjects. In addition the levels of cholesterol α-epoxide, 5-cholesten-5α,6α-epoxy-3β-ol; cholesterol β-epoxide, 5-cholesten-5β,6β-epoxy-3-ol; 7-OH-cholsterol, 5-cholesten-3,7β-diol; 25-OH cholesterol, 5-cholesten-3β, 25-diol; 7-OOH cholesterol, 5-cholesten-3β-ol-7β-hydroperoxide; triol, cholestan-3β,5α,6β-triol.) were measured in blood samples from 25 subjects with CAD and 12 apparently healthy control subjects. Lipids were measured by HPLC with on-line electrospray ionization tandem mass spectrometry (LC/ESI/MS/MS) using established methods. Results were normalized to the content of the precursor lipid (PAPC, 1-hexadecanoyl-2-eicosatetra-5',8',11',14'-enoyl-sn-glycero-3-phosphocholine; PLPC, 1-hexadecanoyl-2-octadecadi-9', 12'-enoyl-sn-glycero-3-phosphocholine; or cholesterol), which were simultaneously quantified by LC/ESI/MS/MS. The results demonstrated that subjects with CAD had higher levels (50% to 4-fold, depending upon the lipid) of each of the phospholipid oxidation products in their plasma than healthy age and sex-matched subjects.

Example 7

Levels of Nitrotyrosine Modulated by Statin Therapy

Case-Control Study

The population consisted of a consecutive sample of patients evaluated in the section of Cardiology at Bostom Medical Center. Case patients were those with a history of coronary artery disease (CAD) defined as a history of myocardial infarction, coronary artery bypass graft surgery, percutaneous coronary intervention, or a stenosis of 50% or greater in one or more major coronary vessels demonstrated by coronary angiography. Control patients were recruited by advertisement and had no clinical history of CAD or symptoms suggestive of angina pectoris or congestive heart failure.

Prospective Intervention Study

The population consisted of a consecutive sample of patients recruited from the Preventive Cardiology Clinic at the Cleveland Clinic Foundation from June 2001 until January 2002 who were eligible and consented to participate in the study. Patients 21 years of age and older without clinical evidence of CAD and with low-density lipoprotein cholesterol (LDL-C) levels $\geq$130 mg/dL, despite at least 6-8 weeks of therapeutic lifestyle interventions, were eligible to participate in the study. Briefly at initial screening, a detailed medical history was obtained, a thorough physical examination was performed, and a fasting lipoprotein profile was obtained. Patients potentially eligible for the study received counseling on nutritional and exercise interventions. If after 6-8 weeks LDL-C remained $\geq$130 mg/dL, patients were eligible for enrollment in the study. Fasting morning plasma samples were collected prior to initiation of therapy (baseline), and following 12 weeks of atorvastatin therapy (10 milligrams orally per day). Patient with active liver disease or renal insufficiency defined as serum creatine levels of 1.8 mg per deciliter or greater were excluded. Patients included in the study received treatment with atorvastatin at a dose of 10 milligrams orally per day. All patients gave written informed consent, and the Institutional Review Board at the Cleveland Clinic Foundation approved the study protocol.

Laboratory Analysis

Blood samples were collected into serum separator tubes (Case-control study) or EDTA tubes (Intervention study) from overnight fasted patients. Samples were centrifuged at 3500 rpm for 10 minutes, plasma/serum recovered, and aliquots stored at −80° C. until analysis. Personnel blinded to clinical data performed all laboratory measurements. Lipoprotein/lipid profiles and high sensitivity C-reactive protein (CRP) measurements were performed using CDC standardized assays.

Nitrotyrosine

Protein-bound nitrotyrosine levels were determined by stable isotope dilution liquid chromatography-electrospray ionization tandem mass spectrometry based methods using an ion trap mass spectrometer (LCQ Deca, ThermoFinigann, San Jose, Calif.). Synthetic 3-nitro-[$^{13}C_6$]tyrosine (2 pmol) and [$^{13}C_9{}^{15}N_1$]tyrosine (2 nmol) were added to protein pellets both as internal standards and to simultaneously monitor nitrotyrosine, tyrosine and potential artifactual formation of nitrotyrosine during analyses. Nitrotyrosine content in samples is expressed as the mole ratio between nitrotyrosine and the precursor amino acid tyrosine.

Statistical Analysis

Case-Control Study

Nitrotyrosine and C-reactive protein were not normally distributed (Shapiro-Wilk test). Consequently, quartile-based methods were used for analyses and summary measures were presented as median and interquartile range. Comparisons between cases and controls were made with chi-square tests for categorical measures and Wilcoxon rank-sum tests for continuous measures. Trends were assessed with Cochran-Armitage tests.

Logistic regression models (SAS System, SAS Institute, Cary N.C.) were employed to estimate the relative risk of CAD for patient in the highest quartile of nitrotyrosine versus the lowest quartile without and with adjustment for single and multiple risk factors. Likelihood ratio Chi-square tests were used to compare models that included age, gender, LDL-C, HDL-C, triglycerides, history of diabetes, history of hypertension, and current smoking; the above cardiac risk factors plus either nitrotyrosine or CRP; and the above cardiac risk factors plus both CRP and nitrotyrosine. To further estimate the potential clinical utility of nitrotyrosine determinations, receiver-operator characteristics (ROC) curves were derived from logistic regression procedures for laboratory measures used for CAD risk assessment including LDL-C+HDL-C alone, the combination of LDL-C+HDL-C+CRP, and the combination of LDL-C+HDL-C+CRP+nitrotyrosine.

Intervention Study

Wilcoxon rank-sum test was used to analyze the differences between measurements at baseline and 12 weeks. Spearman-rank correlations were used to assess associations between both baseline and atorvastatin-induced changes in nitrotyrosine levels, lipoprotein profile measures and CRP levels. Approximate 95% confidence intervals were found using Fisher's r-to-z transform. Multiple regression analyses were performed to determine factors associated with changes in nitrotyrosine levels.

Results

Case-Control Study

Patient Demographics

The clinical and laboratory characteristics of the study participants are shown in Table 3. Patients with CAD were older, more likely to be male, and more likely to have hypertension, diabetes mellitus, or family history of CAD. Patients with CAD also had increased fasting triglycerides, lower HDL levels, higher levels of CRP, and were more likely to use lipid lowering drugs and other cardiovascular medications.

Nitrotyrosine Levels and CAD

Figure 12:
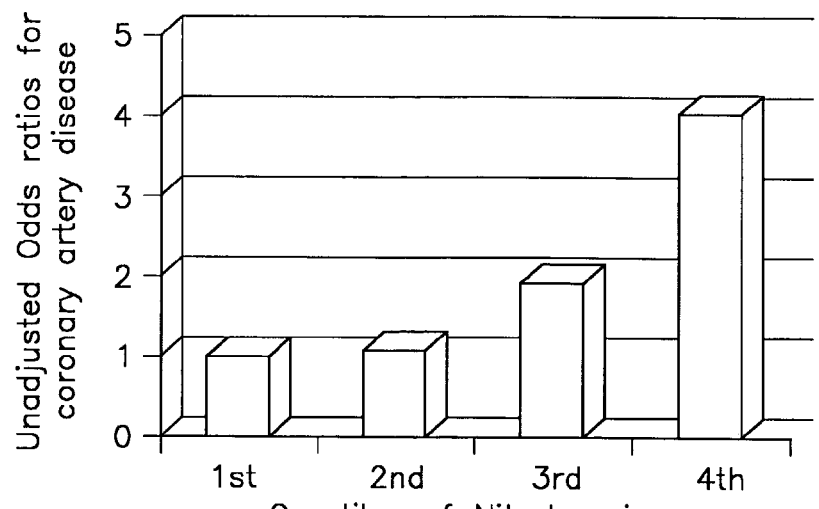
FIG. 12 is a graph showing the unadjusted odds ratios of CAD risk to quartiles of nitrotyrosine.

Nitrotyrosine levels were significantly greater for patients with CAD compared to controls (median values, 9.1 μmol/mol tyrosine v. 5.7 μmol/mol tyrosine, respectively; P<0.001) (FIG. 12). Further, rates of CAD increased with nitrotyrosine quartiles (26% v. 58%, lowest v. highest quartiles; P<0.001 for trend). Patients in the highest quartile of nitrotyrosine levels had increased risk of CAD compared to patients in the lowest quartile (odds ratio, 4.1; 95% confidence interval, 1.9-8.5; P<0.001 for trend). CAD rates also increased across the CRP distribution (25% v. 50%, lowest v. highest quartiles; P<0.001 for trend). Patients in the highest quartile of CRP levels had increases risk of CAD compared to the lowest quartile (odds ratio, 3.0; 95% confidence interval, 1.4-6.3; P<0.001 for trend). The rate of CAD amongst patients by nitrotyrosine quartiles v. quartiles of other known predictors of cardiovascular risk revealed that the proportion of patients with CAD was highest amongst patients with both upper quartile of nitrotyrosine and lower quartile of high density lipoprotein cholesterol (HDL-C), as compared to patients with both lower quartile of nitrotyrosine and upper quartile of HDL-C levels (81% v. 14%; P<0.001). The proportions of patients with CAD was also higher among patients in the upper quartile of both nitrotyrosine and CRP compared to patients in the lower quartile of both nitrotyrosine and CRP compared to patients in the lower quartiles of both inflammatory markers (67% v. 19%; P=0.002)

Nitrotyrosine Levels and CAD Risk Factors

Nitrotyrosine levels correlated with age (r=0.14, p=0.03), fasting triglycerides (r=0.14, p=0.03), and CRP (r=0.15, p=0.02); however, these associations were small in magnitude and accounted for less than 5% of the observed variance in nitrotyrosine. There was no significant correlation between nitrotyrosine and LDL-C, HDL-C, or total cholesterol. Interestingly, diabetics had higher nitrotyrosine levels than nondiabetics (median values, 9.26 μmol/mol tyrosine v. 6.0 μmol/mol tyrosine, respectively; P<0.001). Except for CAD, none of the factors presented in Table 3 showed a significant association with nitrotyrosine.

Adjusted Models for Nitrotyrosine and CAD

The results of univariate and multivariate analysis are shown in FIG. 12. Nitrotyrosine levels remained significant predictors of CAD status following single-factor adjustments for individual traditional CAD risk factors (age, gender, history of diabetes, current smoking, history of hypertension, HDL-C, LDL-C, triglycerides) and CRP, with 4th quartile odds ratios ranging from 3.4 (95% confidence interval 1.7-7.3; P=0.002) after adjustment for diabetes, to 4.2 (95% confidence interval, 2.0-8.8; P<0.001) after adjustment for HDL-C. In multivariable analyses with simultaneous adjustment for each single CAD risk factor, nitrotyrosine independently predicted CAD risk (4th quartile odds ratio, 3.16; 95% confidence interval, 1.35 to 7.37; P<0.001). Further, nitrotyrosine remained a strong and independent predictor of CAD risk following addition of CRP to the multivariable model (4th quartile odds ratio, 3.0; 95% confidence interval=1.3 to 7.1; P=0.001).

(To evaluate whether nitrotyrosine levels independently associate with CAD, odds ratios for nitrotyrosine quartiles were adjusted for traditional CAD risk factors individually, and then collectively as a Framingham Global Risk Score. Nitrotyrosine levels remained highly correlated with CAD following individual adjustments for age, gender, history of diabetes, current smoking, history of hypertension, HDL-C, LDL-C, triglycerides and CRP, with minimal changes observed in adjusted odds ratios and confidence intervals (not shown). After adjustment for the Framingham Global Risk Score, nitrotyrosine remained a robust predictor of CAD risk (Table 4, Model 1; adjusted nitrotyrosine $4^{th}$ quartile OR (95% CI)=5.6(2.2-14.5), P<0.001). Addition of CRP to the model had little effect on the odds ratio for nitrotyrosine as a predictor of CAD status (Table 4, Model 2; adjusted nitrotyrosine $4^{th}$ quartile OR (95% CI)=5.4(2.0-14.3), P<0.001). Likelihood ratio tests confirmed that introducing nitrotyrosine to multivariable prediction models that included established markers of cardiovascular risk (e.g., Model 3, Table 4) significantly added to risk-prediction for CAD (Chi-square=10.42, P<0.001).

The association between nitrotyrosine and CAD was apparent despite increased use of lipid-lowering drugs, and other cardiovascular agent in the CAD group. Separate analyses confirmed that nitrotyrosine levels remained a significant protector of CAD status for subjects off each medication class including statins. For example, in subjects off statins (N=201), median protein bound nitrotyrosine levels (μmol/mol tyrosine) in CAD subjects were significantly greater than in controls (9.3 μmol/mol; interquartile range, 4.7-14.0 v. 5.6 μmol/mol; interquartile range, 2.6-8.4; P<0.001). Moreover, amongst subjects off statins, nitrotyrosine remained a strong and independent predictor of CAD risk factors and CRP (4th quartile odds ratio, 3.6; 95% confidence interval, 1.2 to 10.4; P=0.02). Interestingly, amongst subjects taking statins (N=61), protein-bound nitrotyrosine levels no longer were significantly increased in CAD v. nonCAD subjects (P=0.52), suggesting that statins may influence nitrotyrosine levels.

Clinical Utility of Nitrotyrosine Measures

To confirm that nitrotyrosine levels added to the predictive value of established markers of cardiovascular risk, we performed likelihood ratio tests on multivariable logistic regression models with and without nitrotyrosine. Introducing nitrotyrosine to a multivariable prediction model that includes age, gender, levels of LDL-C, HDL-C, triglycerides, and a history of diabetes mellitus, hypertension and current smoking status significantly added to risk prediction for CAD (Chi-square=10.42, P<0.001). Further, significant increases in risk-prediction for CAD were also noted upon addition of nitrotyrosine levels to a multivariable prediction model that included the above CAD risk factors plus CRP (Chi-square=10.06, P=0.0002).

To further gauge the potential clinical utility of nitrotyrosine levels relative to alternative laboratory measures commonly monitored for CAD risk assessment, we performed receiver-operating-characteristic analyses (Table 6). Comparisons were performed on the area under the receiver-operating-characteristic curves for risk-prediction models based on LDL-C+HDL-C alone, the combination of LDL-C+HDL-C and CRP, or the combination of LDL-C+HDL-C+CRP and nitrotyrosine. The addition of CRP to LDL-C+HDL-C increased the area under the ROC curve from 0.60 to 0.66 (P<0.001). Addition of nitrotyrosine levels to the model containing LDL-C+HDL-C+CRP resulted in a further significant increase in the area under the receiver-operating-characteristic curve (0.66 to 0.714, P<0.001)(Table 6). Comparable results (i.e., significant increases upon addition of nitrotyrosine) were obtained when lipid parameters were instead modeled as LDL-C:HDL-C ratio or TC:HDL-C ration (data not shown), Intervention Study Statin-Induced Changes in Nitrotyrosine Levels v. other CAD Risk Factors and Inflammatory Markers To directly assess the impact of statin therapy on systemic levels of protein-bound nitrotyrosine v. other CAD risk factors and inflammatory markers, a prospective interventional study was performed. Patients who were healthy and without clinical evidence of CAD or diabetes and were eligible for primary prevention therapy (LDL-C>130 at baseline) were eligible for enrollment. Subjects (N=35; 49% male) had a meant age of 54+10 years old. Table 5 shows the levels of total cholesterol, LDL-C, HDL-C, triglycerides, apolipoprotein B-100, CRP and protein-bound nitrotyrosine at baseline and following 12 weeks of atorvastatin therapy (10 mg PO QHS). Treatment with atorvastatin led to significant reductions in mean levels of total cholesterol, LDL-C, and apolipoprotein B-100 levels (25%, 39%, and 29%, respectively). Remarkably, statin-induced reductions in plasma nitrotyrosine levels (25%; P=0.017) were similar in magnitude to decreases in total cholesterol and LDL particle number (i.e., apolipoprotein B100, Table 5). A non-significant trend toward statin-induced reductions in CRP levels was also observed (11% reduction; P=0.096).

No significant correlations were noted between baseline levels of nitrotyrosine, lipid parameters, and CRP. Further, no significant correlations were noted between statin-induced changes in nitrotyrosine v. changes in lipoprotein and inflammatory markers including total cholesterol (95% confidence intervals, −0.23=ρ=0.43), LDL-C (95% confidence interval, −0.2=ρ=0.45), HDL-C (95% confidence interval, −0.18=ρ=0.47), or CRP (95% confidence interval, −0.22=ρ=0.44). Finally, in multivariable regression analysis there was no significant association between change in nitrotyrosine levels and changes in levels of total cholesterol, LDL-C, HDL-C, and CRP (F-ratio=0.71; P=0.6).

The results of the present studies suggest that nitrotyrosine, a marker specific for protein modification by nitric oxide-derived oxidants, may serve as a novel inflammatory marker for CAD. Systemic levels of protein-bound nitrotyrosine were associated with risk of CAD even following multivariable adjustments for traditional CAD risk factors and CRP. Importantly, statin therapy promoted significant reductions in nitrotyrosine levels that were similar in magnitude to reductions in total cholesterol and LDL particle number. Moreover, reductions in nitrotyrosine promoted by statin therapy were independent of reductions in lipid parameters and CRP. Taken together, the present results suggest that nitrotyrosine measurements may prove useful both in assessing CAD risk and for monitoring the anti-inflammatory effects of statins.

One of the more remarkable findings of the present studies was the significant reduction in nitrotyrosine promoted by systemic therapy with low dose atorvastatin. It has become increasingly clear that statins promote systemic effects that extend beyond simply lowering cholesterol levels. Statin-induced inhibition in superoxide formation has been shown in cultured vascular smooth muscle cells. The mechanism for decreased superoxide formation appears to involve inhibition of isoprenylation of the protein rac, a key NAD(P)H Oxidase component that normally requires isoprenylation for appropriate translocation to the plasma membrane surface during cell stimulation. Thus, in contrast to the modest alterations in CRP typically noted relative to those observed for lipoprotein and cholesterol levels, the present results demonstrated that nitrotyrosine reductions were comparable in magnitude to those noted for total cholesterol or LDL particle number with administration of low dose statin (Table 5). The growing appreciation of the pleiotropic actions of statins has underscored the requirement for new measures that quantify the anti-inflammatory properties of this widely used class of drugs. The present studies suggest that systemic nitrotyrosine levels may serve as an independent measure of the anti-inflammatory actions of statins.

A corollary to these findings is that low dose atorvastatin therapy promotes potent systemic antioxidant effects by suppressing formation of nitric oxide-derived oxidants. Recent randomized trials with antioxidant vitamins, particularly alpha tocopherol, have failed to demonstrate benefit against cardiovascular disease, and it is notable that alpha tocopherol is relatively ineffective at blocking the effects of nitric oxide derived oxidants.

Elevated nitrotyrosine levels in patients with diabetes were recently reported, a finding also observed in our cohort. Postprandial elevations in nitrotyrosine levels following consumption of a high fat or high glucose meal that were attenuated following simvastatin therapy were also recently reported. While nitrotyrosine enrichment in human atherosclerotic lesions is well known from both immunohistochemical and mass spectrometry-based studies, the present study is the first to directly correlate systemic levels of nitrotyrosine with CAD risk and response to therapy. The ability of nitrotyrosine levels to provide additive predictive value for determining CAD risk suggests that nitrotyrosine may be useful in identifying individuals who might otherwise not be identified by currently employed screening methods.

TABLE 3

Baseline Characteristics by Coronary Artery Disease Status*

| Characteristic | Control n = 163 | CAD n = 99 | P-value |
|---|---|---|---|
| Age (yrs) | 51 (41–61) | 58 (53–67) | <0.001 |
| Women, n % | 70 (43%) | 24 (24%) | 0.002 |
| Hypertension, % | 74 (45%) | 61 (62%) | 0.01 |
| Family history of CAD, n % | 31 (19%) | 47 (47%) | <0.001 |
| Diabetes mellitus, n % | 23 (14%) | 34 (34%) | <0.001 |
| Current smoker, n % | 48 (29%) | 22 (22%) | 0.20 |
| Statins, n % | 22 (13%) | 39 (39%) | <0.001 |
| Angiotensin converting enzyme inhibitors, n % | 29 (18%) | 39 (39%) | <0.001 |
| B-Blockers, n % | 37 (23%) | 71 (72%) | <0.001 |
| Calcium channel blockers, n % | 14 (9%) | 18 (18%) | 0.02 |
| Angiotensin II receptor blockers, % | 2 (1%) | 3 (3%) | 0.37 |
| Total cholesterol level (mg/dL) | 196 (172–221) | 196 (167–221) | 0.35 |
| High-density lipoprotein cholesterol (mg/dL) | 66 (51–97) | 53 (39–67) | 0.005 |
| Low-density lipoprotein cholesterol (mg/dL) | 99 (57–132) | 99 (44–128) | 0.44 |
| Triglycerides (mg/dL) | 116 (79–154) | 148 (125–195) | <0.001 |
| C-reactive protein (mg/dL) | 0.31 (0.14–0.79) | 0.50 (0.33–1.50) | <0.001 |
| Nitrotyrosine (μmol/mol tyrosine) | 5.66 (2.73–8.57) | 9.13 (4.81–13.79) | <0.001 |

*Continuous measures are shown as median (interquartile range), while categorical measures are shown as percentage with risk factor.

TABLE 4

Additive predictive value of nitrotyrosine to commonly measured laboratory markers for CAD risk: receiver operating characteristics curve analyses

| | LDL-C, HDL-C alone (Model 1) | LDL-C, HDL-C + CRP (Model 2) | LDL-C, HDL-C + CRP + Nitrotyrosine (Model 3) |
|---|---|---|---|
| C | 0.599 | 0.661 | 0.714 |
| $R^2$ | 5.2% | 10.8% | 17.7% |
| P-value | — | <0.001* | <0.001** |

*P-value for comparison between model 1 and model 2.
**P-value for comparison between model 2 and model 3. Receiver operating characteristics curve analyses of case-control cohort were calculated using LDL-C + HDL-C alone (Model 1); LDL-C + HDL-C and CRP (Model 2); and LDL-C + HDL-C + CRP and nitrotyrosine (Model 3). C, calculated area under the receiver operating characteristics curve. $R^2$, percentage of variance in CAD explained by model.

TABLE 5

Lipid levels, high sensitivity C-Reactive Protein, and Nitrotyrosine at Baseline and after 12 Weeks of Treatment with Atorvastatin*

| Characteristics | Baseline (n = 35) | 12 Weeks (n = 35) | Absolute and % Change | P-Value |
|---|---|---|---|---|
| Nitrotyrosine (μmol/mol tyrosine) | 15 ± 7 | 11 ± 5 | −4 (25) | 0.017 |
| C-reactive protein (mg/dL) | 0.26 ± 0.32 | 0.23 ± 0.33 | −0.2 (11) | 0.096 |
| Total cholesterol level (mg/dL) | 253 ± 27 | 190 ± 28 | −63 (25) | <0.001 |
| High-density lipoprotein cholesterol (mg/dL) | 56 ± 12 | 58 ± 12 | 2 (4) | 0.21 |
| Low-density lipoprotein cholesterol (mg/dL) | 169 ± 22 | 103 ± 29 | −66 (39) | <0.001 |
| Triglycerides (mg/dL) | 146 ± 90 | 132 ± 81 | −14 (10) | 0.22 |
| Apolipoprotein B-100 (mg/dL) | 135 ± 17 | 96 ± 21 | −39 (29) | <0.001 |

*Data presented as mean ± SD

Example 8

Statin Antioxidant Effects

Methods

Study Protocol

We performed a prospective, open-label study. The study cohort consisted of a consecutive sample of patients (n=35) recruited from the Preventive Cardiology Clinic at the Cleveland Clinic Foundation. Patients 21 years of age and older without clinical evidence of coronary artery disease and with LDL cholesterol (LDL-C) levels 130 mg per deciliter or greater, despite at least 6-8 weeks of therapeutic lifestyle interventions, were eligible to participate in the study. Briefly, at initial screening, a detailed medical history was obtained, a thorough physical examination was performed, and a fasting lipoprotein profile was obtained. Patients potentially eligible for the study received counseling on nutritional and exercise interventions. If after 6-8 weeks LDL-C remained above 130 mg/dL, patients were eligible for enrollment in the study. Patients included in the study received treatment with atorvastatin at a dose of 10 milligrams orally per day. Fasting morning plasma samples were collected prior to initiation of therapy (baseline), and following 12 weeks of therapy.

Patients with active liver disease or renal insufficiency defined as a serum creatinine level of 1.8 mg per deciliter or greater were excluded. To evaluate compliance and side effects of atorvastatin therapy, patients were followed through clinic visits at weeks 2, 4, 6, 8, and 12. All patients gave written informed consent, and the Institutional Review Board at the Cleveland Clinic Foundation approved the study protocol.

Blood Samples

Blood samples were collected into EDTA tubes from fasting patients. Samples were centrifuged at 3500 rpm for 10 minutes at 4° C., and stored under conditions to minimize artificial oxidation (i.e., with antioxidant cocktail, under inert atmosphere). Briefly, plasma was removed and allocated into tubes containing butylated hydroxytoluene (100 μM final) and diethylenetriaminepentaacetic acid (100 μM final) overlaid with argon and stored at −80° C. until analysis. Standard methods were used to measure lipid levels and high-sensitivity CRP.

Nitrotyrosine, Dityrosine, Chlorotyrosine, and Ortho-Tyrosine Analyses

Protein-bound nitrotyrosine was determined by stable isotope dilution liquid chromatography—tandem mass spectrometry on an ion trap mass spectrometer (LCQ Deca, ThermoFinigann, San Jose, Calif.), as previously described. Protein-bound chlorotyrosine, dityrosine and o-tyrosine analyses were performed by gas chromatography/mass spectrometry following derivatization of amino acids to their n-propyl per heptafluorylbutyryl derivatives using a Finnigan Voyager GC/MS in the negative ion chemical ionization mode. Briefly, proteins within plasma were delipidated and desalted using a single phase mixture of organic/aqueous solvents. Synthetic $[^{13}C_6]$-labeled standards (in cases of nitrotyrosine, chlorotyrosine, o-tyrosine) or $[^{13}C_{12}]$-labeled standards (in case of dityrosine) were added to plasma protein pellets and used as internal standards for quantification of natural abundance analytes. Simultaneously, universal labeled precursor amino acids $[^{13}C_9,^{15}N_1]$tyrosine (for nitrotyrosine, chlorotyrosine and dityrosine) or $[^{13}C_9,^{15}N_1]$phenylalanine (for o-tyrosine) were added to plasma protein pellets to simultaneously monitor for potential artifactual formation of each oxidation product, as previously described. Proteins were hydrolyzed under inert argon atmosphere in methane sulfonic acid, and then samples passed over mini solid-phase C18 extraction columns (Supelclean LC-C 18-SPE minicolumn; 3 ml; Supelco, Inc., Bellefone, Pa.) prior to mass spectrometry analysis.

For all analyses, results were normalized to the content of the precursor amino acid L-tyrosine (for nitrotyrosine, chlorotyrosine or dityrosine) or phenylalanine (for o-tyrosine), which were monitored within the same injection of each oxidized amino acid. All amino acid oxidation products were routinely detected at 10 fmol on-column with a signal to noise ratio of >10:1. When presented normalized to the level of the precursor amino acid, all oxidation products were detectable at <1 μmol/mol precursor, under the conditions employed. Intrapreparative formation of nitro$[^{13}C_9,^{15}N]$tyrosine, chloro$[^{13}C_9,^{15}N]$tyrosine, di$[^{13}C_{18},^{15}N_2]$tyrosine and ortho$[^{13}C_9,^{15}N]$tyrosine were routinely monitored for all analyses and was usually negligible under the sample preparation conditions employed (i.e. <<5% of the level of the natural abundance product observed). On the rare occasion where intrapreparative oxidation exceeded 5% of the level of the natural abundance analyte monitored, repeat sample preparation and mass spectrometric analyses were performed.

Statistical Analysis

Data are presented as mean±SD, and significance level was set at p<0.05. Wilcoxon rank-sum test was used to analyze the differences between $NO_2Tyr$, diTyr, and CRP at baseline and 12 weeks, as they were not normally distributed. The differences between baseline and 12 weeks for lipid parameters, ClTyr, and o-Tyr levels were performed using paired student T-Test. Spearman-rank correlation was used to assess the association between baseline $NO_2Tyr$, diTyr, ClTyr, o-Tyr, CRP, and lipid parameters. Multiple regression analyses were performed to determine factors associated with changes in $NO_2Tyr$, diTyr, and ClTyr. All statistical analyses were performed using SPSS version 11.0 (Chicago, Ill.).

Results

Baseline characteristics of the patients are shown in Table 6. Follow-up data was available for all 35 patients at 12 weeks. In general, other than hypercholesterolemia, the patients were a healthy cohort without any known coronary artery disease or diabetes. Absolute and percentage change of baseline and 12 week measurements of total cholesterol (TC), LDL cholesterol (LDL-C), HDL cholesterol (HDL-C), triglycerides, CRP, ClTyr, diTyr, $NO_2Tyr$ and o-Tyr are shown in Table 7. As expected, treatment with atorvastatin led to a significant reduction in TC, LDL-C, and apoB-100 levels (25%, 39%, and 29%, respectively). Atorvastatin caused comparable significant reductions in the levels of oxidation products produced by myeloperoxidase and nitric oxide-derived oxidants (reductions in ClTyr, diTyr, and $NO_2Tyr$ of 30%, 32%, and 25%, respectively; Table 7). In contrast, the reduction in o-Tyr and CRP were modest (9% and 11%, respectively) and failed to reach statistical significance (Table 7).

Further analyses were performed to determine if either baseline levels or observed changes in oxidation markers ($NO_2Tyr$, diTyr, ClTyr, and o-Tyr) were associated with baseline levels or observed changes in either lipid parameters or CRP. Baseline $NO_2Tyr$ levels, a specific molecular fingerprint for protein modification by nitric oxide-derived oxidants, were correlated with fasting triglyceride levels (r=−0.36, P=0.033; Table 8). No other significant correlations were found between baseline levels of oxidation markers and either lipid parameters or CRP (Table 8). Significant correlations were noted between statin-induced changes in ClTyr, a specific molecular fingerprint of myeloperoxidase-catalyzed oxidation, and changes in both $NO_2Tyr$ and HDL-C levels (r=0.37, P=0.028 and r=0.36, P=0.036, respectively; Table 9). Changes in o-Tyr, a product of protein oxidation by metal catalyzed hydroxyl radical like species, was associated with changes in fasting triglycerides (r=−0.38, P=0.026; Table 9). In multiple regression analyses that included changes in lipid parameters and oxidation markers, changes in ClTyr were the only parameter that predicted changes in $NO_2Tyr$ levels (P=0.002).

The present studies demonstrate significant reductions in levels of specific molecular footprints of distinct oxidative pathways following 12 weeks of atorvastatin therapy. Marked reductions in systemic markers specific for protein oxidative damage by myeloperoxidase- and nitric oxide-derived oxidants were observed that were largely independent of statin-induced changes in lipid parameters and CRP. Further, the magnitude of reductions in oxidation markers on statin therapy were comparable in size to the reductions observed in fasting TC and apo B100. The mechanisms underlying the overall systemic antioxidant effects are likely class effects for these agents (i.e., inhibition in isoprenylation).

The oxidation markers chosen for the present study provide mechanistic information with regards to the pathways responsible for their formation. Further, unlike lipid oxidation products, which are readily generated during sample storage and archiving, many of the molecular markers monitored are both stable and not readily formed during storage. These characteristics make them potentially useful and practical tools for both defining oxidative pathways operative in cardiovascular syndromes, as well as for assessing the efficacy of antioxidant and anti-inflammatory interventions. They also are required for the meaningful analysis of archival specimens for correlation with clinical outcomes unless significant measures were taken during sample collection and storage to prevent or minimize lipid oxidation. The sophisticated and labor-intensive methods required for accurate determination of oxidative markers, which typically involve mass spectrometry, have delayed their widespread use in clinical studies. However, these very same methods illustrate the necessity of using such techniques, since simultaneous monitoring of assay methods to ensure no significant artifactual formation of the oxidation markers during sample handling and processing for analyses, has proven to be critical in method development and accurate quantitative assessment of these markers.

Figure 13:
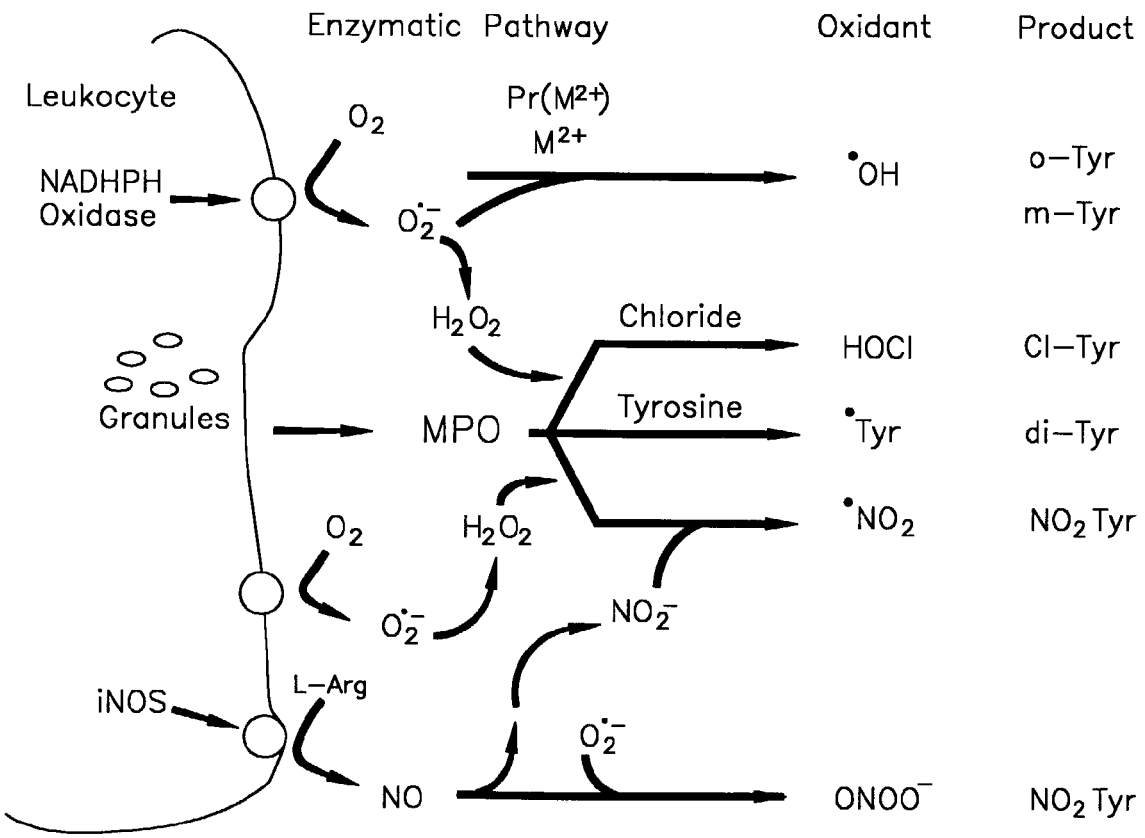
FIG. 13 is a scheme that illustrates enzymatic pathways employed by leukocytes for generating reactive oxidants and diffusible radical species, interactions between these pathways, oxidants generated, and stable end-products that serve as markers for distinct pathways. Each of the oxidation pathways and reactive oxidant species noted has the potential to initiate lipid peroxidation, based on studies with in vitro model systems. Abbreviations: $H_2O_2$, hydrogen peroxide; HOCl, hypochlorous acid; eNOS, endothelial nitric oxide synthase; iNOS, inducible nitric oxide synthase; L-Arg, L-arginine, $M^{2+}$, redox-active metal ion; MPO, myeloperoxidase; NO, nitrogen monoxide (nitric oxide); $NO_2$, nitrogen dioxide; $NO_2^-$, nitrite; NOX, NADH oxidase of vascular endothelial cells; $O_2$, molecular oxygen; $O_2^{\cdot-}$, superoxide anion; .OH, hydroxyl radical; $ONOO^-$, peroxynitrite; $Pr(M^{2+})$, protein-bound redox-active metal ion; Tyr, tyrosyl radical; Tyrosine analogs: Cl-Tyr, 3-chlorotyrosine; di-Tyr, dityrosine; m-Tyr, meta-tyrosine; o-Tyr, orthotyrosine; $NO_2$-Tyr, 3-nitrotyrosine.

Oxidative consumption of nitric oxide, such as through interaction with superoxide, both suppresses nitric oxide bio-availability and produces a potent nitrating oxidant, peroxynitrite ($ONOO^-$; FIG. 13). The present studies show that multiple alternative oxidation pathways, particularly those catalyzed by myeloperoxidase, demonstrate comparable reductions.

Another intriguing finding of the present studies was the statistically significant association between statin-elicited reductions in levels of protein-bound nitrotyrosine and chlorotyrosine in plasma (r=0.37, P=0.028; Table 6). Such a finding is consistent with myeloperoxidase playing a significant role in formation of nitric oxide-derived oxidants in humans (FIG. 13). Organ chamber studies using preconstricted vascular and tracheal rings, as well as myeloperoxidase knock out mice, support a role for myeloperoxidase in regulating nitric oxide bio-availability and function. The present results provide further support for the many links between myeloperoxidase and nitric oxide-derived oxidants, and suggest that this hemoprotein may play a role in endothelial dysfunction in vivo.

In summary, by using molecular footprints of specific oxidative pathways, we have shown that statins promote potent systemic antioxidant effects independent of changes seen in lipid, lipoprotein and CRP levels. Furthermore, the amino acid oxidation products monitored, ClTyr, dityr, o-Tyr and $NO_2Tyr$, demonstrate reductions even when presented as a product/precursor ratio, indicating a true decrease in oxidant stress following atorvastatin therapy. These data show that statins induce potent systemic antiinflammatory and antioxidant effects, and have important implications for the monitoring of non-lipid related, or so-called pleiotropic actions, of this important class of drug.

TABLE 6

Baseline Characteristics

| Characteristics | Primary Prevention (n = 35) |
|---|---|
| Age (years) | 54 ± 10 |
| Female sex | 18 (51) |
| Body mass index ($kg/m^2$) | 29 ± 6 |
| Systolic blood pressure (mm Hg) | 119 ± 14 |
| Diastolic blood pressure (mm Hg) | 71 ± 8 |
| Aspirin treatment | 10 (29) |
| Multivitamin use | 22 (63) |
| Current smoker | 2 (6) |

TABLE 7

Lipid levels, C-reactive protein, and Oxidation Products at Baseline and after 12 Weeks of treatment with Atorvastatin

| Characteristics | Baseline (n = 35) | 12 Weeks (n = 35) | Absolute (%) change | P-Value |
|---|---|---|---|---|
| Dityrosine (μmol/mol tyrosine) | 34 ± 11 | 23 ± 8 | −11 (32) | <0.001 |
| Chlorotyrosine (μmol/mol tyrosine) | 19 ± 10 | 13 ± 4 | −6 (30) | 0.01 |
| Nitrotyrosine (μmol/mol tyrosine) | 15 ± 7 | 11 ± 5 | −4 (25) | 0.02 |
| ortho-tyrosine (μmol/mol tyrosine) | 89 ± 54 | 81 ± 40 | −8 (9) | 0.49 |
| C-reactive protein (mg/dL) | 0.26 ± 0.32 | 0.23 ± 0.33 | −0.2 (11) | 0.10 |
| Total cholesterol (mg/dL) | 253 ± 27 | 190 ± 28 | −63 (25) | <0.001 |
| HDL cholesterol (mg/dL) | 56 ± 12 | 58 ± 12 | 2 (4) | 0.21 |
| LDL cholesterol (mg/dL) | 169 ± 22 | 103 ± 29 | −66 (39) | <0.001 |
| Triglycerides (mg/dL) | 146 ± 90 | 132 ± 81 | −14 (10) | 0.22 |
| Apolipoprotein B-100 (mg/dL) | 135 ± 17 | 96 ± 21 | −39 (29) | <0.001 |

TABLE 8

Baseline Spearman Correlations*

| | TG | HDL-C | LDL-C | CRP | diTyr | $NO_2Tyr$ | ClTyr | o-Tyr |
|---|---|---|---|---|---|---|---|---|
| TC | $0.41^1$ | 0.18 | $0.76^4$ | −0.16 | 0.02 | −0.16 | −0.22 | −0.02 |
| TG | | $-0.40^2$ | 0.07 | −0.11 | 0.1 | $-0.36^3$ | −0.20 | 0.20 |
| HDL-C | | | −0.01 | 0.12 | 0.08 | 0.27 | 0.06 | −0.21 |
| LDL-C | | | | −0.20 | −0.01 | −0.07 | −0.33 | −0.16 |
| CRP | | | | | 0.07 | 0.15 | −0.07 | 0.12 |
| diTyr | | | | | | 0.06 | 0.03 | −0.05 |

TABLE 8-continued

Baseline Spearman Correlations*

| | TG | HDL-C | LDL-C | CRP | diTyr | NO$_2$Tyr | ClTyr | o-Tyr |
|---|---|---|---|---|---|---|---|---|
| NO$_2$Tyr | | | | | | | 0.29 | −0.05 |
| ClTyr | | | | | | | | −0.03 |

*P-values shown only for significant correlations (p < 0.05)
Abbreviations: TC, total cholesterol; TG, triglycerides; HDL-C, HDL cholesterol; LDL-C, LDL cholesterol; CRP, C-reactive protein; diTyr, dityrosine; NO$_2$Tyr, nitrotyrosine; ClTyr, chlorotyrosine; o-Tyr, ortho-tyrosine.
[1] P = 0.014
[2] P = 0.017
[3] P = 0.033
[4] P = 0.001

TABLE 9

Spearman Correlations for Changes in Oxidative Markers and Lipid Parameters

| | TG | HDL-C | LDL-C | CRP | diTyr | NO$_2$Tyr | ClTyr | o-Tyr |
|---|---|---|---|---|---|---|---|---|
| TC | 0.23 | 0.34[5] | 0.64[4] | 0.11 | 0.03 | 0.10 | −0.01 | −0.02 |
| TG | | 0.04 | −0.12 | −0.02 | −0.03 | 0.04 | 0.18 | 0.38[2] |
| HDL-C | | | −0.02 | 0.16 | −0.23 | 0.16 | 0.36[3] | −0.05 |
| LDL-C | | | | −0.01 | −0.04 | 0.19 | 0.09 | −0.21 |
| CRP | | | | | 0.10 | 0.15 | −0.18 | 0.23 |
| diTyr | | | | | | −0.18 | 0.02 | −0.11 |
| NO$_2$Tyr | | | | | | | 0.37[1] | 0.05 |
| ClTyr | | | | | | | | 0.01 |

*P-values shown only for significant correlations (p < 0.05)
Abbreviations: TC, total cholesterol; TG, triglycerides; HDL-C, HDL cholesterol; LDL-C, LDL cholesterol; CRP, C-reactive protein; diTyr, dityrosine; NO$_2$Tyr, nitrotyrosine; ClTyr, chlorotyrosine; o-Tyr, ortho-tyrosine.
[1] P = 0.028
[2] P = 0.026
[3] P = 0.036
[4] P = 0.00004
[5] P = 0.04

Example 10

MPO-Generated Oxidation Products are Dramatically Reduced by Statin Therapy

Figure 14A:
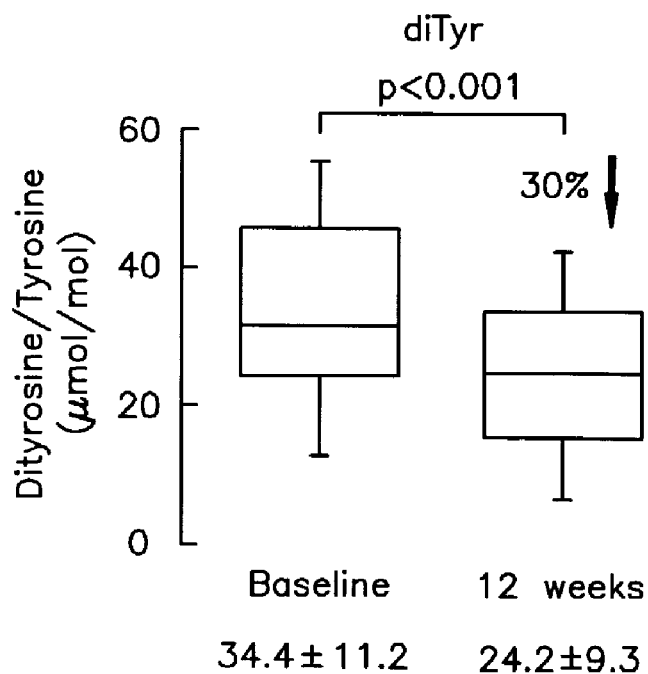
FIGS. 14(A-B) are graphs showing the median and interquartile range of dityrosine (A) and nitrotyrosine (B) levels at baseline and after 12 weeks of treatment with atorvastatin. Subjects had fasting plasma levels of dityrosine (diTyr) nitrotyrosine ($NO_2$Tyr) determined at baseline and following 12 weeks of atorvastatin therapy (10 mg PO QHS). Data is plotted as a box-whisker plots. Boxes encompass $25^{th}$ to $75^{th}$ percentiles. Lines within boxes represent median values. Bars represent $2.5^{th}$ and 97.5th percentiles.
Figure 14B:
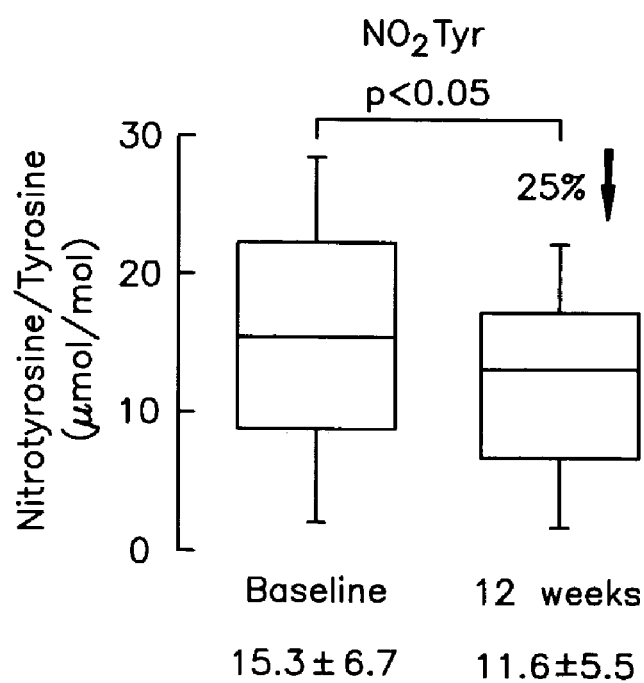
Figure 15:
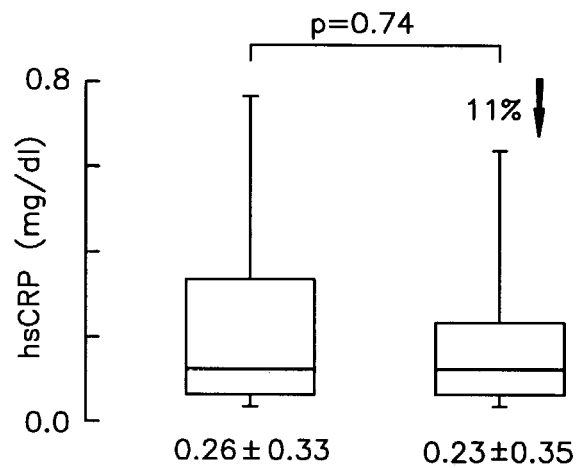
FIG. 15 is a graph showing the median and interquartile range of C-reactive Protein levels at baseline and after 12 weeks of treatment with atorvastatin. Subjects had fasting plasma levels of C-reactive protein (hsCRP) determined at baseline and following 12 weeks of atorvastatin therapy (10 mg PO QHS). Data is plotted as a box-whisker plots. Boxes encompass $25^{th}$ to $75^{th}$ percentiles. Lines within boxes represent median values. Bars represent $2.5^{th}$ and $97.5^{th}$ percentiles.

We used HPLC with on-line electrospray ionization tandem mass spectrometry to examine the effects of statin therapy (atorvastatin, 10 mg PO QHS) on MPO-generated markers of protein and lipid oxidation in vivo. Subjects (n=35) with LDL cholesterol ≧130 mg/dL were enrolled and monitored at baseline and following 12 weeks of treatment. FIGS. 14(A-B) show significant reductions in dityrosine (30%), nitrotyrosine (24%) were observed while hs-CRP only decreased by 11%. In an alternative study, levels of lipid oxidation products were monitored at baseline in subjects currently on statin therapy, following a 4 week washout period where statin therapy was stopped, and then following resumption of statin therapy (12 weeks of atorvastatin, 10 mg PO QHS). FIG. 15 shows the modest decrease in CRP (11%) noted with 12 weeks of statin therapy was consistent with published studies, but failed to reach significance.

Example 11

Use of Specific Lipid Oxidation Products to Monitor Systemic Antioxidant Effects of Simvastatin (Zocor)

Figure 16:
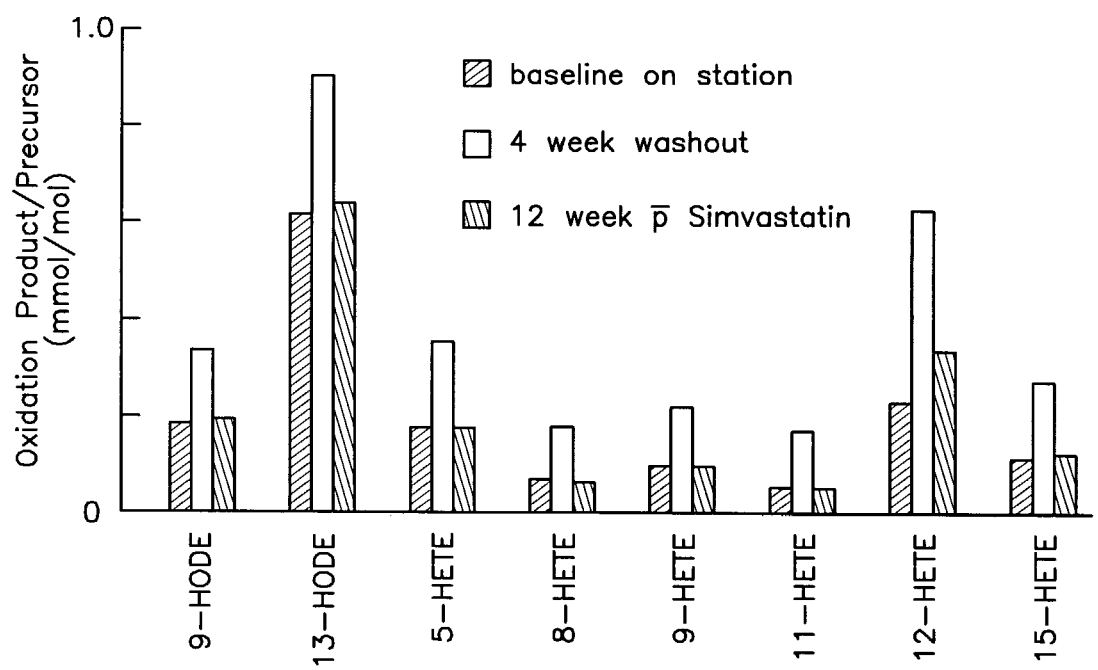
FIG. 16 is a graph showing the plasma level of lipid oxidation products following administration of simvastatin. Subjects currently on statin therapy were enrolled to monitor plasma levels of specific lipid oxidation products formed by MPO. Baseline levels of markers were determined while on therapy (solid bar). Patients were then instructed to stop statin therapy for a 4 week washout period, and plasma levels were determined (open bar). Patients were then initiated on simvastatin, 10 mg PO QHS and plasma levels of products determined 12 weeks later (hatched bar).

Plasma levels of multiple specific oxidation products that can be formed by MPO were monitored at baseline, following a 4 week washout period, and 12 weeks following simvastatin therapy in subjects (n=15) currently on statin therapy (at baseline: atorvastatin, n=9; simvastatin, n=5, pravastatin, n=1). FIG. 16 shows the plasma level of lipid oxidation products following administration of atorvastatin. Note that each of the indicated HETEs and HODEs monitored went up in plasma following removal of statin therapy, and then were again reduced when subjects are placed back on simvastatin therapy.

Example 12

COX II Inhibitor Therapy Promotes Systemic Antioxidant/Anti-Inflammatory Effect as Monitored with MPO and Multiple Distinct Oxidation Products Formed by MPO COX II is implicated as a major pathway for promoting inflammation through generation eicosanoids. It follows that use of a COX II inhibitor should suppress inflammation, leading to decreased levels of MPO and products MPO can generate. To test this we are examining subjects with rheumatoid arthritis (n=10). Plasma was drawn at baseline, and then 16 weeks following therapy with refocoxib (i.e. VIOXX; 25 mg PO QD). Plasma levels of MPO, protein-bound nitrotyrosine, chlorotyrosine, dityrosine, and 9-H(P)ETE and F2Isoprostantes were monitored. Marked reductions in each marker were noted (Table 10), along with clinical improvement in each subject. These results suggest that MPO and its oxidation products may serve as objective quantifiable indices for monitoring the anti-inflammatory and antioxidant actions of this (or any other) class of agents.

TABLE 10

| Marker | Baseline | 16 weeks | P value |
| --- | --- | --- | --- |
| $F_2$Isoprostane (mmol/mol) | 1.02 | 0.76 | 0.01 |
| 9-H(P)ETE (mmol/mol) | 0.45 | 0.20 | <0.001 |
| Nitrotyrosine (μmol/mol) | 17.0 | 11.2 | <0.001 |
| Chlorotyrosine (μmol/mol) | 18.3 | 15.8 | 0.025 |
| Dityrosine (μmol/mol) | 42.1 | 35.4 | 0.05 |
| MPO (ng/ml) | 28.9 | 10.8 | <0.001 |

Example 13

ACEI Therapy Promotes Systemic Antioxidant/Anti-Inflammatory Effect as Monitored with MPO and Multiple Distinct Oxidation Products Formed by MPO Angiotensin converting enzyme (ACE) is intimately linked to superoxide production by vascular cells. Moreover, multiple studies have argued that ACE inhibitors (ACEI) function to not only lower blood pressure, but also to decrease superoxide production, and hence oxidant stress, within the artery wall. The methods used to monitor this effect are limited to examination of tissues, typically in animal model systems or cell culture experiments. No one has examined systemic markers of oxidant stress or inflammation as a way of monitoring these non-blood pressure related beneficial effects of this class of agents.

Subjects (n=9) had plasma drawn at baseline, and then 16 weeks following therapy with lisinopril (Zestril, 20 mg PO QD). Plasma levels of MPO, protein-bound nitrotyrosine, chlorotyrosine, dityrosine, and 9-H(P)ETE and $F_2$Isoprostantes were monitored. Marked reductions in each marker were noted in subjects (Table 11).

ACEI therapy has been shown to decrease cardiovascular event rates, and risk for development of complications associated with diabetes. Many of these clinical benefits are thought to be linked to a generalized anti-inflammatory/antioxidant effect in the vasculature. We propose that monitoring systemic levels of MPO and its oxidation products will serve as a way of monitoring the anti-inflammatory and antioxidant actions of this, or any, class of drug.

TABLE 11

| Marker | Baseline | 16 weeks | P value |
| --- | --- | --- | --- |
| $F_2$Isoprostane (mmol/mol) | 0.82 | 0.72 | 0.08 |
| 9-H(P)ETE (mmol/mol) | 0.39 | 0.21 | <0.01 |
| Nitrotyrosine (μmol/mol) | 14.2 | 10.3 | <0.01 |
| Chlorotyrosine (μmol/mol) | 16.1 | 15.0 | 0.08 |
| Dityrosine (μmol/mol) | 36.5 | 24.1 | 0.02 |
| MPO (ng/ml) | 20.2 | 8.8 | <0.001 |

Example 14

ARB Therapy Promotes Systemic Antioxidant/Anti-Inflammatory Effect as Monitored with MPO and Multiple Distinct Oxidation Products Formed by MPO Angiotensin receptor blocking agents are a new therapy used for treatment of hypertension. They act upon the same biochemical axis as ACEI. Accordingly, they promote clinical benefits beyond those linked to blood pressure reduction—those related to presumed anti-inflammatory and antioxidant actions. However, no means for objectively monitoring these effects have been available. We hypothesized that monitoring levels of MPO and its oxidation products might serve as a way of quantifying the anti-inflammatory and antioxidant effects of ARBs. Subjects (n=16) had plasma drawn at baseline, and then 16 weeks following therapy with losartan (Cozaar, 25 mg PO QD). Plasma levels of MPO, protein-bound nitrotyrosine, chlorotyrosine, dityrosine, and 9-H(P)ETE and $F_2$Isoprostantes were monitored. Marked reductions in each marker were noted in subjects (Table 12). These studies underscore the potential utility of MPO and its oxidation products for monitoring systemic antioxidant and anti-inflammatory effects of therapeutic interventions.

TABLE 12

| Marker | Baseline | 16 weeks | P value |
| --- | --- | --- | --- |
| $F_2$Isoprostane (mmol/mol) | 0.93 | 0.68 | 0.01 |
| 9-H(P)ETE (mmol/mol) | 0.42 | 0.27 | <0.001 |
| Nitrotyrosine (umol/mol) | 14.5 | 8.1 | <0.001 |
| Chlorotyrosine (umol/mol) | 17.0 | 14.3 | 0.05 |
| Dityrosine (umol/mol) | 35.8 | 28.5 | 0.06 |
| MPO (ng/ml) | 24.7 | 9.9 | <0.001 |

Example 15

Statin Therapy Decreases Plasma Levels of MPO

Subjects (n=27) had plasma drawn at baseline, and then 16 weeks following therapy with Atorvastatin (Lipitor, 10 mg PO QD). Plasma levels of MPO were monitored. Significant reductions in MPO levels were noted in subjects following therapy (Table 13). These studies underscore the potential utility of MPO for monitoring systemic antioxidant and anti-inflammatory effects of therapeutic interventions like statins.

TABLE 13

| Marker | Baseline | 16 weeks | % change | P value |
| --- | --- | --- | --- | --- |
| MPO (ng/ml) | 19.7 +/− 5.2 | 17.3 +/− 4.8 | 12.2% | <0.017 |

From the above description of the invention, those skilled in the art will perceive improvements, changes and modifications. Such improvements, changes and modifications within the skill of the art are intended to be covered by the appended claims.

I claim:

1. A method of monitoring anti-inflammatory or antioxidant actions or both of a therapeutic agent, said method comprising:

determining a level of at least one systemic marker indicative of inflammation or oxidation in a bodily sample taken from a subject during or following administration of the therapeutic agent, the systemic marker including at least one of MPO activity, MPO mass, an MPO-generated oxidation product selected from the group consisting of nitrotyrosine, methionine sulphoxide, homocitrulline, and combinations thereof, the bodily sample including at least one of serum, plasma, urine, neutrophils, subpopulation of neutrophils, monocytes or subpopulations monocytes, wherein the level of the systemic marker is determined per unit of the bodily sample when the systemic marker is MPO activity or MPO mass or both, and comparing the level of the systemic marker in the bodily sample with a predetermined value to monitor the anti-inflammatory or antioxidant actions or both of the therapeutic agent, wherein a decrease in the level of the systemic marker in the bodily sample as compared to the predetermined value indicates that the therapeutic agent provides anti-inflammatory or antioxidant actions or both in the subject.

2. The method of claim 1, wherein the predetermined value is determined from a level of the systemic marker in a comparable bodily sample that was taken from the subject prior to administration of the therapeutic agent.

3. The method of claim 1, wherein the predetermined value is a single normalized value or a range of normalized values.

4. The method of claim 1, wherein the systemic marker is MPO activity or MPO mass, and the bodily sample comprises at least one of serum, plasma, neutrophils, and monocytes.

5. The method of claim 1, wherein the therapeutic agent comprises a pharmacodynamic agent that exhibits an anti-inflammation or antioxidant action or both in vivo through suppression of oxidation pathways used in the formation of myeloperoxidase and nitric oxide derived oxidants.

6. The method of claim 1, wherein the therapeutic agent comprises at least one of HMG CoA reductase inhibitors, COX-2 inhibitors, angiotensin system inhibitor, angiotensin II receptor blocking agents, cytokine inhibitors, tumor necrosis factor-$\alpha$, (TNF-$\alpha$) inhibitors, antihyperlioproteinemics, inhibitors of cholesterol biosynthesis, insulin sensitizing agents, antihypertensive agents, anti-thrombotic agents, anti-platelet agents, fibrinolytic agents, direct thrombin inhibitors, ACAT inhibitors, CETP inhibitors, V-CAM inhibitors, immunomodulating agents, thiazolidinediones, and glycoprotein receptor inhibitors.

7. The method of claim 1, wherein the therapeutic agent comprises a HMG CoA reductase inhibitor, and wherein the HMG CoA reductase inhibitor is administered to treat cardiovascular disease.

8. The method of claim 1, wherein the systemic marker is homocitrulline.

9. The method of claim 1, wherein the systemic marker is MPO activity or MPO mass.

10. The method of claim 1, wherein the systemic marker is MPO mass, wherein the bodily sample is serum or plasma, and wherein the level of MPO mass per unit of the bodily sample is determined by contacting the bodily sample with a polyclonal antibody that reacts with MPO to form a complex between MPO and the polyclonal antibody and determining the level of said complex in the bodily sample.

11. The method of claim 1, wherein the systemic marker is MPO activity and the level of MPO activity per unit of the bodily sample is determined using a colorometric assay.

12. The method of claim 1, wherein the systemic marker is MPO activity and the level of MPO activity per unit of the bodily sample is determined using a flow cytometer.

13. A method of monitoring anti-inflammatory or antioxidant actions or both of therapeutic agents, said method comprising:

determining a level of at least one systemic marker indicative of inflammation or oxidation or both in a bodily sample taken from a subject following administration of the therapeutic agent, the systemic marker including at least one of MPO activity, MPO mass, an MPO-generated oxidation product selected from the group consisting of nitrotyrosine, methionine sulphoxide, homocitrulline, and combinations thereof;

the bodily sample including at least one of serum, plasma, urine, monocytes or neutrophils in-blood, wherein the level of the systemic marker is determined per unit of the bodily sample when the systemic marker is MPO activity or MPO mass or both, and comparing the level of the systemic marker in the bodily sample with a predetermined value to monitor the anti-inflammatory or antioxidant actions or both of the therapeutic agent, wherein the therapeutic agent is administered to treat disorders where inflammation or oxidative damage or both is linked to pathogenesis of the disorder.

14. The method of claim 13, wherein the predetermined value comprises the level of the systemic marker in a comparable bodily sample obtained from the subject prior to or during administration of the therapeutic agent.

15. The method of claim 13, wherein the therapeutic agent comprises a pharmacodynamic agent that exhibits an anti-inflammation or antioxidant action or both in vivo through suppression of oxidation pathways used in the formation of myeloperoxidase and nitric oxide derived oxidants.

16. The method of claim 15, wherein the therapeutic agent comprises at least one of HMG CoA reductase inhibitors, COX-2 inhibitors, angiotensin system inhibitor, angiotensin II receptor blocking agents, cytokine inhibitors, tumor necrosis factor-$\alpha$, (TNF-$\alpha$) inhibitors, antihyperlioproteinemics, inhibitors of cholesterol biosynthesis, insulin sensitizing agents, antihypertensive agents, anti-thrombotic agents, anti-platelet agents, fibrinolytic agents, direct thrombin inhibitors, ACAT inhibitors, CETP inhibitors, V-CAM inhibitors, immunomodulating agents, thiazolidinediones, and glycoprotein receptor inhibitors.

17. The method of claim 13, wherein the disorder is an inflammatory or autoimmune disorder.

18. The method of claim 13, further comprising monitoring the level of the systemic marker during or following administration of the therapeutic agent to determine a dosage of the therapeutic agent effective to provide a medically desirable result.

19. The method of claim 13, wherein the systemic marker is homocitrulline.

20. A method of monitoring anti-inflammatory or antioxidant actions or both of a HMG CoA reductase inhibitor, said method comprising:

determining the level of at least one systemic marker indicative of inflammation or oxidation in a bodily sample taken from a subject following administration of the HMG CoA reductase inhibitor, the systemic marker including at least one of MPO activity, MPO mass, an MPO-generated oxidation product selected from the group consisting of nitrotyrosine, methionine sulphoxide, homocitrulline, and combinations thereof, the bodily sample including at least one of serum, plasma, urine, monocytes or neutrophils, wherein the level of the systemic marker is determined per unit of the bodily sample when the systemic marker is MPO activity or MPO mass or both, and comparing the level of the systemic marker in the bodily sample with a predetermined value to monitor the anti-inflammatory or antioxidant actions or both of the HMG CoA reductase inhibitor, wherein a decrease in the level of the systemic marker in the bodily sample as compared to the predetermined value indicates that the HMG CoA reductase inhibitor provides anti-inflammatory or antioxidant actions or both in the subject.

21. The method of claim 20, wherein the predetermined value is determined from the level of the systemic marker in a comparable bodily sample that was taken from the subject prior to administration of the HMG CoA reductase inhibitor.

22. The method of claim 20 wherein the HMG CoA reductase inhibitor is administered to the subject to treat a disorder where inflammation or oxidative damage or both is linked to pathogenesis of the disorder.

23. The method of claim 20, further comprising monitoring the level the systemic marker during or following administration of the HMG CoA reductase inhibitor to determine a dosage of the HMG CoA reductase inhibitor effective to provide a medically desirable result.

24. The method of claim 20, wherein the systemic marker is homocitrulline.

25. A method of monitoring whether a therapeutic agent provides an anti-inflammatory or antioxidant effect or both, said method comprising:

i. determining the level of at least one systemic marker indicative of inflammation or oxidation in a bodily sample of blood, plasma, serum, or urine taken from a subject during or following administration of the therapeutic agent, the systemic marker being nitrotyrosine, homocitrulline, or both, ii. comparing the level of the systemic marker in the bodily sample with a predetermined value to monitor the anti-inflammatory or antioxidant actions or both of the therapeutic agent, and iii. determining that the therapeutic agent provides the anti-inflammatory or antioxidant effect or both if the level of the systemic marker in the bodily sample is less than the predetermined value.

26. The method of claim 25, wherein the systemic marker is homocitrulline, and the bodily sample comprises at least one of blood, serum, or plasma.

27. The method of claim 25, wherein the systemic marker is nitrotyrosine and the bodily sample comprises at least one of blood, serum, or plasma.

28. The method of claim 25 wherein the systemic marker is homocitrulline and the level of homocitrulline is determined using an immunoassay.

29. The method of claim 25 wherein the systemic marker is nitrotyrosine and the level of nitrotyrosine is determined using an immunoassay.

30. The method of claim 25, wherein the systemic marker is homocitrulline and the level of homocitrulline is determined using a mass spectrometer.

31. The method of claim 25, wherein the systemic marker is nitrotyrosine and the level of nitrotyrosine is determined using a mass spectrometer.

32. The method of claim 25, wherein the systemic marker is nitrotyrosine or homocitrulline and wherein the level of the systemic marker is normalized to the protein content.

33. A method of monitoring anti-inflammatory or antioxidant actions or both of therapeutic agents in a subject having a disease associated with inflammation or oxidation, said method comprising:

determining the number or percentage of the subject's neutrophils or monocytes that contain elevated levels of MPO activity or MPO mass before administration of the therapeutic agent to the subject;

determining the number or percentage of the subject's neutrophils or monocytes that contain elevated levels of MPO activity or MPO mass during or following administration of the therapeutic agent to the subject, wherein a decrease in the number or percentage of the subject's neutrophils or monocytes that contain elevated levels of WO mass or MPO activity during or following administration of the therapeutic agent to the subject as compared to before administration of the therapeutic agent indicates that the therapeutic agent provides an anti-inflammatory or antioxidant actions or both in the subject.

34. The method of claim 33, wherein the disease is atherosclerotic cardiovascular disease.

\* \* \* \* \*